United States Patent [19]
Ballinger et al.

[11] Patent Number: 5,837,516
[45] Date of Patent: Nov. 17, 1998

[54] SUBTILISIN VARIANTS CAPABLE OF CLEAVING SUBSTRATES CONTAINING BASIC RESIDUES

[75] Inventors: Marcus D. Ballinger; James A. Wells, both of Burningame, Calif.

[73] Assignee: Genentech, Inc., South San Francisco, Calif.

[21] Appl. No.: 504,265

[22] Filed: Jul. 19, 1995

Related U.S. Application Data

[63] Continuation-in-part of Ser. No. 398,028, Mar. 3, 1995.

[51] Int. Cl.$^6$ .............................. C12P 21/06; C12N 9/54; C12N 15/57; C12N 15/75

[52] U.S. Cl. ........................ 435/221; 435/68.1; 435/69.1; 435/172.3; 435/221; 435/252.3; 435/252.31; 435/320.1; 536/23.2

[58] Field of Search ................................ 435/68.1, 69.1, 435/172.3, 221, 223, 252.3, 252.31, 320.1; 536/23.2

[56] References Cited

U.S. PATENT DOCUMENTS

| | | | |
|---|---|---|---|
| 4,760,025 | 7/1988 | Estell et al. ............................. | 435/222 |
| 5,371,008 | 12/1994 | Carter et al. ............................ | 435/222 |

FOREIGN PATENT DOCUMENTS

| | | |
|---|---|---|
| 316748 | 5/1989 | European Pat. Off. . |
| 405901 | 1/1991 | European Pat. Off. . |
| 0130756 | 6/1991 | European Pat. Off. . |
| WO 91/11454 | 8/1991 | WIPO . |
| WO 92/02615 | 2/1992 | WIPO . |
| WO 95/30010 | 11/1995 | WIPO . |

OTHER PUBLICATIONS

Bresnahan, P. A. et al., "Human fur gene encodes a yeast kex2–like endoprotease that cleaves pro–Checkthis–NGF in vivo" *Journal of Cell Biology* 111(6,Pt 2):2851–2859 (1990).

Carter et al., "Engineering Subtilisin BPN' for Site–Specific Proteolysis" *Proteins: Struct. Funct., Genet.* 6:240–248 (1989).

Creemers et al., "Modulation of Furin–Mediated Proprotein Processing Activity by Site–directed Mutagenesis" *The Journal of Biological Chemistry* 268(29):21826–21834 (1993).

Eder et al., "Hydrolysis of Small Peptide Substrates Parallels Binding of Chymotrypsin Inhibitor 2 for Mutants of Subtilisn BPN'" *Federation of European Biochemical Societies* 335(3):349–352 (1993).

Forsberg et al., "An Evaluation of Different Enzymatic Cleavage Methods of Recombination Fusion Proteins, Applied on Des (1–3) Insulin–Like Growth Factor I" *Journal of Protein Chemistry* 11(2):201–211 (1992).

(List continued on next page.)

*Primary Examiner*—Eric Grimes
*Assistant Examiner*—William W. Moore
*Attorney, Agent, or Firm*—Jeffrey S. Kubinec

[57] ABSTRACT

The bacterial serine protease, subtilisin BPN', has been mutated so that it will efficiently and selectively cleave substrates containing basic residues. Combination mutants, where Asn 62 was changed to Asp, Gly 166 was changed to Asp (N62D/G166D), and optionally Tyr 104 was changed to Asp had a larger than additive shift in specificity toward substrates containing basic residues. Suitable substrates of the variant subtilisin were revealed by sorting a library of phage particles (substrate phage) containing five contiguous randomized residues. This method identified a particularly good substrate, Asn-Leu-Met-Arg-Lys- (SEQ ID NO: 35), that was selectively cleaved in the context of a fusion protein by the N62D/G166D subtilisin variant. A particularly good substrate for N62D/G166D/Y104D would be Asn-Arg-Met-Arg-Lys- (SEQ ID NO: 76). Accordingly, these variant subtilisin are useful for cleaving fusion proteins with basic substrate linkers and processing hormones or other proteins (in vitro or in vivo) that contain basic cleavage sites.

11 Claims, 17 Drawing Sheets

OTHER PUBLICATIONS

Graf et al., "Electrostatic Complementarity Within the Substrate–Binding Pocket of Trypsin" *Proc. Natl. Acad. Sci.* 85:4961–4965 (1988).

Hosaka et al., "Arg–X–Lys/Arg–Arg Motif as a Signal for Precursor Cleavage Catalyzed by Furin within the Constitutive Secretory Pathway" *Journal of Biological Chemistry* 266(19):12127–12130 (1991).

Hwang et al., "Why ION Pair Reversal by Protein Engineering is Unlikely to Succeed" *Nature* 334:270–272 (1988).

Knauf et al., "Relationship of Effective Molecular Size to Systemic Clearance in Rats of Reconbinant Interleukin–2 Chemically Modified with Water Soluble Polymers" *The Journal of Biological Chemistry* 29(Oct. 15):15064–15070 (1988).

Kraut, Joseph, "Serine Protease: Structure and Mechanism of Catalysis" *Ann. Rev. Biochem.* 46:331–358 (1977).

Lipkind et al., "Molecular Modeling of the Substrate Specificity of Prohormone Convertases SPC2 and SPC3" *The Journal of Biological Chemistry* 270(22):13277–13284 (1995).

Matthews et al., "A Survey of Furin Substrate Specificity Using Substrate Phage Display" *Protein Science* 3:1197–1205 (1994).

Matthews et al., "X–ray Crystallographic Study of Boronic Acid Adducts with Subtilisin BPN'(Novo)" *Journal of Biological Chemistry* 250(18):7120–7126 (1975).

McPhalen et al., "Structural Comparison of Two Serine Proteinase–Protein Inhibitor Complexes: Eglin–C–Subtilisin Carlsberg and CI–2–Subtilisin Novo" *Biochemistry* 27:6582–6598 (1988).

Philip et al., "Kinetics of Subtilisin and Thiolsubtilisin" *Molecular and Cellular Biochemistry* 51(5):5–32 (1983).

Poulos et al., "Polypeptide Halomethyl Ketones Bind to Serine Proteases as Analogs of the Tetrahedral Intermediate" *The Journal of Biological Chemistry* pp. 1097–1103 (1975).

Rheinnecker et al., "Engineering a Novel Specificity in Subtilisin BPN'" *Biochemistry* 32(5):1199–1203 (1993).

Robertus et al., "Subtilisin; a Stereochemical Mechanism Involving Transition–State Stabilization" *Biochemistry* 11:4293–4303 (1972).

Robertus et al., "An X–Ray Crystallographic Study of the Binder of Peptide Choloromethyl Ketone Inhibitiors to Subtilisin BPN'" *Biochemistry* 11(13):2439–2449 (1972).

Russell et al., "Rational modification of enzyme catalysis by engineering surface charge" *Nature* 328:496–500 (1987).

Siezen et al., "Homology Modelling and Protein Engineering Strategy of Subtilases, the Family of Subtilisn–Like Serine Proteinases" *Protein Engineering* 4(7):719–737 (1991).

Siezen et al., "Homology Modelling of the Catalytic Domain of Human Furin, a Model for the Eukaryotic Subtilisin–Like Proprotein Convertases" *EJB* pp. 255–266 (1993).

Stauffer et al., "The Effect on Subtilisin Activity of Oxidizing a Methionine Residue" *The Journal of Biological Chemistry* 244(19):5333–5338 (1969).

Svendsen, I., "Chemical Modifications of The Subtilisins With Specific Reference to the Binding of Large Substrates. A Review." *Carlsberg Rs. Commun.* 41(5):237–291 (1976).

Wells et al., "Cloning, sequencing, and secretion of *Bacillus amyloliquefaciens* subtilisin in *Bacillus subtilis*" *Nucleic Acids Research* 11(22):7911–7929 (1983).

Wells et al., "Designing substrate specificity by protein engineering of electrostatic interactions" *Proc. Natl. Acad. Sci USA* 84:1219–1223 (1987).

Wise et al., "Expression of a human proprotein processing enzyme: correct cleavage of the von Willebrand factor precursor at a paired basic amino acid site" *Proc. Natl. Acad. Sci. USA* 87:9378–9382 (1990).

Wright et al., "Structure of Subtilisin BPN' at 2–5 A Resolution" *Nature* 221:235–242, 1969.

Bode et al., "Refined 1.2 A crystal structure of the complex formed between subtilisin Carlsberg and the inhibitor eglin c. Molecular structure of eglin and its detailed interaction with subtilisin" *EMBO Journal* 5(4):813–818 (1986).

Brenner et al., "Structural and enzymatic characterization of a puried prohormone–processing enzyme: Secreted, soluble Kex2 protease" *Proc. Natl. Acad. Sci. USA* 89:922–926 (1992).

Drenth et al., "Subtilisin Novo; The Three–Dimensional Structure and Its Comparison with Subtilisin BPN'" *Europoean Journal of Biochemistry* 26:177–181 (1972).

Hedstrom et al., "Converting Trypsin to Chymotrypsin: The Role of Surface Loops" *Science*, 255(5049):1249–1253 (1992).

Rheinnecker et al., "Variants of Subtilisin BPN' with Altered Specificity Profiles" *Biochemistry* 33:221–225 (1994).

Smeekens, Steven P., "Processing of Protein Precursors by a Novel Family of Substilisin–Related Mammalian Endoproteases" *Bio/Technology* 11:182–186 (1993).

Steiner et al., "The New Enzymology of Precursor Processing Endoproteases" *Journal of Biological Chemistry* 267(33):23435–23438 (1992).

Stennicke et al., "Effects of introduced aspartic and glutamic acid residues on the P'1 substrate specificity, pH dependence and stability of carboxypeptidase Y" *Protein Engineering* 7(7):911–916 (1994).

Ballinger et al., "Designing Subtilisin BPN' to Cleave Substrates Containing Dibasic Residues" *J. Biochem.* 34:13312–13319 (1995).

Estell et al., "Probing Steric and Hydrophobic Effects on Enzyme–Substrate Interactions by Protein Engineering" *Science* 233:659–663 (1986).

Graycar et al., "Altering the Proteolytic Activity of Subtilisin through Protein Engineering" *Annals of the New York Academy of Sciences* 672:71–79 (1992).

Nakayama et al., "Consensus Sequence for Precursor Processing at Mono–arginyl Sites" *Journal of Biological Chemistry* 267:16335–16340 (1992).

Wells et al., "Recruitment of Substrate–specificity Properties from One Enzyme Into a Related One by Protein Engineering" *Proc. Natl. Acad. Sci. USA* 84:5167–5171 (1987).

```
                                              mroI
                                              bspMII
                                              bspEI[dam-]
                                              bsaWI                            haeI
                             scfI             accIII[dam-]
1921 ACCACCACAC CGCCGCGCT TAATGCGCCG CTACAGGGCG CGTCCGGATC XGATCCGACG CGAGGCTGGA TGGCCCTTCCC CATTATGATT CTTCTCGCTT
     TGGTGGTGTG GCGGCGCGA ATTACGCGGC GATGTCCCGC GCAGGCCTAG ?CTAGGCTGC GCTCCGACCT ACCGGAAGGG GTAATACTAA GAAGAGCGAA haeI                  bspMI
2021 CCGGCGGCAT CGGGATGCCC GCGTTGCAGG CCATGCTGTC CAGGCAGGTA GATGACGACC ATCAGGGACA GCTTCAAGGA TCGCTCGCGG CTCTTACCAG
     GGCCGCCGTA GCCCTACGGG CGCAACGTCC GGTACGACAG GTCCGTCCAT CTACTGCTGG TAGTCCCTGT CGAAGTTCCT AGCGAGCGCC GAGAATGGTC narI
                                                                                                     kasI
                                                                 hgiAI/aspHI                         hinlI/acyI
                                                                 bsp1286                             hgiCI
                                                                 bsiHKAI                             haeII
                                        nspBII            bglI   bmyI                                banI
                                                                                                     ahaII/bsaHI
2121 CCTAACTTCG ATCACTGGAC CGCTGATCGT CACGGCGATT TATGCCGCCT CGGCGAGCAC ATGGAACGGG TTGGCATGGA TTGTAGGGCG CGCCCTATAC
     GGATTGAAGC TAGTGACCTG GCGACTAGCA GTGCCGCTAA ATACGGCGGA GCCGCTCGTG TACCTTGCCC AACCGTACCT AACATCCGCG GCGGGATATG hgiCI                                 pflMI
                                                                        naeI banI
                                                                        cfr10I
2221 CTTGTCTGCC TCCCCGCGTT GGGTCGCGGT GCATGGAGCC GGGCCACCTC GAAGCCGGCG GCACCTCGCT AACGGATTCA CCACTCCAAG
     GAACAGACGG AGGGGCGCAA CGCAGCGCCA CGTACCTCGG CCCGGTGGAG CTTGGACTAC CGTGGAGCGA TTGCCTAAGT GGTGAGGTTC mstI
                  aviII/fspI  pflMI                                                           gsuI/bpmI
             bsmI
2321 AATTGGAGCC AATCAATTCT TGCGGAGAAC TGTGAATGCC CAAACCAACC CTTGGCAGAA CATATCCATC GCGTCCGCCA TCTCCAGCAG CCGCACGCGG
     TTAACCTCGG TTAGTTAAGA ACGCCTCTTG ACACTTACGC GTTTGGTTGG GAACCGTCTT GTATAGGTAG CGCAGGCGGT AGAGGTCGTC GGCGTGCGCC avaI                                              drdI
2421 CGCATCTCGG GCCGCGTTGC TGGCGTTTTT CCATAGGCTC CGCCCCCCTG ACGAGCATCA CGCTCAAGTC AGAGGTGGCG AAACCCGACA
     GCGTAGAGCC CGGCGCAACG ACCGCAAAAA GGTATCCGAG GCGGGGGGAC TGCTCGTAGT GCGAGTTCAG TCTCCACCGC TTTGGGCTGT bsaWI
2521 GGACTATAAA GATACCAGGC GTTTCCCCCT GGAAGCTCCC TCGTGTTCCG ACCCTGCCGC TTACCGGATA CCTGTCCGCC TTTCTCCCTT
     CCTGATATTT CTATGGTCCG CAAAGGGGGA CCTTCGAGGG AGCACAAGGC TGGGACGGCG AATGGCCTAT GGACAGGCGG AAAGAGGGAA
```

FIG. 6D

```
                                                                          hgiAI/aspHI
                                                                          bsp1286
                                                                          bsiHKAI
                                                                          bmyI
                                                                          apaLI/snoI
                                                                          alw44I/snoI
             haeII                      scfI                                              
2621 CGGGAAGCGT GGCGCTTTCT CAATGCTCAC GCTGTAGGTA TCTCAGTTCG TTCGCTCCAA GCTGGGCTGT GTGCACGAAC CCCCCGTTCA
     GCCCTTCGCA CCGCGAAAGA GTTACGAGTG CGACATCCAT AGAGTCAAGC AAGCGAGGTT CGACCCGACA CACGTGCTTG GGGGGCAAGT
        nspBII
       mcrI               bsaWI                                                alwNI
2721 GCCCGACCGC TGCGCCTTAT TCGGTAACTA TCGTCTTGAG TCCAACCCGG TAAGACACGA CTTATCGCCA CTGGCAGCAG CCACTGGTAA CAGGATTAGC
     CGGGCTGGCG ACGCGGAATA AGCCATTGAT AGCAGAACTC AGTTGGGCC ATTCTGTGCT GAATAGCGGT GACCGTCGTC GGTGACCATT GTCCTAATCG
                              haeI                                                                        eco57I
2821 AGAGCGAGGT ATGTAGGCGG TGCTACAGAG TTCTTGAAGT GGTGGCCTAA CTACGGCTAC ACTAGAAGGA CAGTATTTGG TATCTGCGCT CTGCTGAAGC
     TCTCGCTCCA TACATCCGCC ACGATGTCTC AAGAACTTCA CCACCGGATT GATGCCGATG TGATCTTCCT GTCATAAACC ATAGACGCGA GACGACTTCG
                                                          nspBII
2921 CAGTTACCTT CGGAAAAAGA GTTGGTAGCT CTTGATCCGG CAAACAAACC ACCGGCTGTA GCGGTGGTTT TTTTGTTTGC AAGCAGCAGA TTACGCGCAG
     GTCAATGGAA GCCTTTTTCT CAACCATCGA GAACTAGGCC GTTTGTTTGG TGGCCGACCAT CGCCACCAAA AAAACAAACG TTCGTCGTCT AATGCGCGTC
                                                                                                       rcaI
          bstYI/xhoII bstYI/xhoII                                                                     bspHI
3021 AAAAAAGGA TCTCAAGAAG ATCCTTTGAT CTTTTCTACG GGGTCTGACG CTCAGTGGAA CGAAAACTCA CGTTAAGGGA TTTTGGTCAT GAGATTATCA
     TTTTTTTCCT AGAGTTCTTC TAGGAAACTA GAAAAGATGC CCCAGACTGC GAGTCACCTT GCTTTTGAGT GCAATTCCCT AAAACCAGTA CTCTAATAGT
          bstYI/xhoII bstYI/xhoII            ahaIII/draI                                    eaml105I
3121 AAAAGGATCT TCACCTAGAT CCTTTTAAAT GTTTTAAATC AATCTAAAGT ATATATGAGT AAACTTGGTC TGACAGTTAC CAATGCTTAA
     TTTTCCTAGA AGTGGATCTA GGAAAATTTA CAAAATTTAG TTAGATTTCA TATATACTCA TTTGAACCAG ACTGTCAATG GTTACGAATT
        hgiCI
        banI                                                                    eaml105I
3221 TCAGTGAGGC ACCTATCTCA GCGATCTGTT TATTCGTTC ATCCATAGTT GCCTGACTCC CCGTCGTGTA GATAACTACG GCTTACCATC
     AGTCACTCCG TGGATAGAGT CGCTAGACAA ATAAGCAAG TAGGTATCAA CGGACTGAGG GGCAGCACAT CTATTGATGC CGAATGGTAG
                                    gsuI/bpmI
              bsaI           cfr10I                                                      bglI
3321 TGGCCCCAGT GCTGCAATGA TACCGGAGA CCCACGCTCA CCGGCTCCAG ATTATCAGC AATAAACCAG CCGGCCGGAA GGGCCGAGCG CAGAAGTGGT
     ACCGGGGTCA CGACGTTACT ATGGCGCTCT GGGTGCGAGT GGCCGAGGTC TAATAGTCG TTATTTGGTC GGTCGGCCTT CCCGGCTCGC GTCTTCACCA
```

FIG. 6E

```
                                                                              mstI psp1406I
                                                                                avaIII/fspI
                  aseI/asnI/vspI
3421 CCTGCAACTT TATCCGCCTC CATCCAGTCT ATTAATTGTT GCCGGGAAGC TAGAGTAAGT AGTTCGCCAG TTAATAGTTT GCGCAACGTT GTTGCCATTG
     GGACGTTGAA ATAGGCGGAG GTAGGTCAGA TAATTAACAA CGGCCCTTCG ATCTCATTCA TCAAGCGGTC AATTATCAAA CGCGTTGCAA CAACGGTAAC
     scfI
     pstI
     bsgI
                                                              bsaWI
3521 CTGCAGGCAT CGTGGTGTCA CGCTCGTCGT TTGGTATGGC TTCATTCAGC TCCGGTTCCC AACGATCAAG GCGAGTTACA TGATCCCCCA TGTTGTGCAA
     GACGTCCGTA GCACCACAGT GCGAGCAGCA AACCATACCG AAGTAAGTCG AGGCCAAGGG TTGCTAGTTC CGCTCAATGT ACTAGGGGGT ACAACACGTT
              pvuI/bspCI  eaeI
              mcrI        cfrI
3621 AAAAGCGGTT AGCTCCTTCG GTCCTCCGAT CGTTGTCAGA AGTAAGTTGG CCGCAGTGTT ATCACTCATG GTTATGGCAG CACTGCATAA TTCTCTTACT
     TTTTCGCCAA TCGAGGAAGC CAGGAGGCTA GCAACAGTCT TCATTCAACC GGCGTCACAA TAGTGAGTAC CAATACCGTC GTGACGTATT AAGAGAATGA
                                                                                                          hincII/hindII
                                                                                                  mcrI    hinlI/acyI
                                                                                                  bcgI    ahaII/bsaHI
3721 GTCATGCCAT CCGTAAGATG CTTTTCTGTG ACTGGTGAGT ACTCAACCAA GTCATTCTGA GAATAGTGTA TGCGGCGACC GAGTTGCTCT TGCCCGGCGT
     CAGTACGGTA GGCATTCTAC GAAAAGACAC TGACCACTCA TGAGTTGGTT CAGTAAGACT CTTATCACAT ACGCCGCTGG CTCAACGAGA ACGGGCCGCA
                                        scaI
                              hgiAI/aspHI
                              bsp1286        psp1406I
                              bsiHKAI   xmnI
                              bmyI      asp700                                                         bstYI/xhoI  nspBII
                              ahaIII/draI                                                                          
3821 CAACACGGGA TAATACCGCG CCACATAGCA GAACTTTAAA AGTGCTCATC ATTGGAAAAC GTTCTTCGGG GCGAAAACTC TCAAGGATCT TACCGCTGTT
     GTTGTGCCCT ATTATGGCGC GGTGTATCGT CTTGAAATTT TCACGAGTAG TAACCTTTTG CAAGAAGCCC CGCTTTTGAG AGTTCCTAGA ATGGCGACAA
                   hgiAI/aspHI
                   bsp1286
                   bsiHKAI
                   bmyI
                   apaLI/snoI
                   alw44I/snoI        eco57I
     bstYI/xhoII
3921 GAGATCCAGT TCGATGTAAC CCACTCGTGC ACCCAACTGA TCTTCAGCAT CTTTTACTTT CACCAGCGTT TCTGGGTGAG CAAAAACAGG AAGGCAAAAT
     CTCTAGGTCA AGCTACATTG GGTGAGCACG TGGGTTGACT AGAAGTCGTA GAAATGAAA GTGGTCGCAA AGACCCACTC GTTTTTGTCC TTCCGTTTTA
                                                         earI/ksp632I  sspI                                        bsrBI
                                                                                                                   rcaI
                                                                                                                   bspHI
4021 GCCGCAAAAA AGGGAATAAG GGCGACACGG AAATGTTGAA TACTCATACT CTTCCTTTTT CAATATTATT GAAGCATTTA TCAGGGTTAT TGTCTCATGA
     CGGCGTTTTT TCCCTTATTC CCGCTGTGCC TTTACAACTT ATGAGTATGA GAAGGAAAAA GTTATAATAA CTTCGTAAAT AGTCCCAATA ACAGAGTACT
                                                                                                  hinlI/acyI
                                                                                                  ahaII/bsaHI    rcaI
                                                                                                  aatII          bspHI
```

FIG. 6F

```
                                                                                                                 psp1406I
                                                                                                                 ahaIII/draI
4121  GCGGATACAT ATTTGAATGT ATTTAGAAAA ATAAACAAAT AGGGGTTCCG CGCACATTTC CCCGAAAAGT GCCACCTGAC GTCTAAGAAA CCATTATTAT
      CGCCTATGTA TAAACTTACA TAAATCTTTT TATTTGTTTA TCCCCAAGGC GCGTGTAAAG GGGCTTTTCA CGGTGGACTG CAGATTCTTT GGTAATAATA
                                                      bpuAI          aseI/asnI/vspI
                                                      bbsI           xmnI
                                                      ecoO109I/draI  asp700    aflII/bfrI
4221  CATGACACATTA ACCTATAAAA ATAGGCGTAT CACGAGGCCC TTTCGTCTTC AAGAATTAAT TCCTTAAGGA ACGTACAGAC GGCTTAAAAG CCTTTAAAAA
      GTACTGTAAT TGGATATTTT TATCCGCATA GTGCTCCGGG AAAGCAGAAG TTCTTAATTA AGGAATTCCT TGCATGTCTG CCGAATTTTC GGAAATTTTT
                    accI                                                                              apoI
4321  CGTTTTTAAG GGGTTGTAG ACAAGGTAAA GCACAATTCC AAGAAAAACA CGATTAGAA CCTAAAAAGA ACGAATTGA ACTAACTCAT
      GCAAAAATTC CCCAAACATC TGTTCCATTT CGTGTTAAGG TTCTTTTTGT GCTAAATCTT GGATTTTCT TGCTTAAACT TGATTGAGTA
                                                                                          xmnI
                                                                                          asp700
4421  AACCCAGAGG TAAAAAAAGA ACGAAGTCGA GATCAGGGAA TGAGTTTATA AAATAAAAAA AGCACCTGAA AAGGTGTCTT TTTTGAACTT
      TTGGCTCTCC ATTTTTTTCT TGCTTCAGCT CTAGTCCCTT ACTCAAATAT TTTATTTTTT TCGTGGACTT TTCCACAGAA AAAACTTGAA
                                                                                              ahaIII/draI
4521  GTTCTTTTCTT ATCTTGATAC ATATAGAAAT TTATTTTAGT AATAAAATCA TGCTGAAAGG TGCGTTGAAG TGTTGGTATG TATGTGTTTT AAAGTATTGA
      CAAGAAAGAA TAGAACTATG TATATCTTTA AATAAAATCA TTGCAGTAAA ATTATTTAGT ACGACTTTCC ACGCAACTTC ACAACCATAC ATACACAAAA TTTCATAACT
                                                                                                                    sspI
4621  AAACCCTTAA AATTGGTTGC ACAGAAAAAC GTGACTAAAA AAATAACTAA ATAGATGGGG GTTTCTTTTA ATATTATGTG
      TTTGGGAATT TTAACCAACG TGTCTTTTTG CACTGATTTG TTTATTGATT TATCTACCCC CAAAGAAAAT TATAATACAC
                                                                   styI
                                                                   ncoI
                                                                   bsaI dsaI
4721  TCCTAATAGT AGCATTATT CAGATGAAAA ATCAAGGGT TTAGTGGACA AGACAAAAAG TGGAAAAGTG AGACCATGGA GAGAAAAGAA AATCGCTAAT
      AGGATTATCA TCGTAAATAA GTCTACTTTT TAGTTCCCAA AATCACCTGT TCTGTTTTTC ACCTTTTCAC TCTGGTACCT CTCTTTTCTT TTAGCGATTA
                                        ahaIII/draI                                   sspI
                                        apoI
4821  GTTGATTACT TTGAACTTCT GCATATTCTT GAATTTAAAA AGGCTGAAAG AGTAAAAGAT TGTGCTGAAA TATTAGAGTA TAAACAAAAT CGTGAAACAG
      CAACTAATGA AACTTGAAGA CGTATAAGAA CTTAAATTTT TCCGACTTTC TCATTTTCTA ACACGACTTT ATAATCTCAT ATTTGTTTTA GCACTTTGTC
                                                  xcmI                  gsuI/bpmI                         bsmI
4921  GCGAAAGAAA GTTGGTGGTT GTTGTATCGA GCTTTGTCCA ATGTGCAACT GGAGGAGAGC CCTCCCTCG TTACTTTGTA GGCATTCAGT CACAAAAGGT
      CGCTTTCTTT CAACTGGCAA CAACATAGCT CGAAACAGGT TACACGTTGA CCTCCTCTCG TTACTTTGTA AATGAAACAT CCGTAAGTCA GTGTTTTCCA
      eco57I          xcmI
5021  TGTTGCTGAA GTTATTAAAC AAAAGCCAAC AGTTCGTTGG TTGTTTCTCA CATTAACAGT TAAAAATGTT TATGATGGCG AAGAATTAAA TAAGAGTTTG
      ACAACGACTT CAATAATTTG TTTTCGGTTG TCAAGCAACC AACAAAGAGT GTAATTGTCA ATTTTACAA ATACTACCGC TTCTTAATTT ATTCTCAAAC
```

FIG. 6G

```
                                                             aseI/asnI/vspI
5121 TCAGATATGG CTCAAGGATT TCGCCGAATG ATGCAATATA AAAAAATTAA TAAAAATCTT GTTGGTTTTA TGCGTGCAAC GGAAGTGACA ATAAATAATA
     AGTCTATACC GAGTTCCTAA AGCGGCTTAC TACGTTATAT TTTTTTAATT ATTTTTAGAA CAACCAAAAT ACGCACGTTG CCTTCACTGT TATTTATTAT
                           nspI                                                          bsaAI
                           nspHI
                           ppu10I
                           nsiI/avaIII
                           nspI
                           nspHI
5221 AAGATAATTC TTATAATCAG CACATGCATG TATTGGTATG TGTGGAACCA ACTTATTTTA AGAATACAGA AAACTACGTG AATCAAAAAC AATGGATTCA
     TTCTATTAAG AATATTAGTC GTGTACGTAC ATAACCATAC ACACCTTGGT TGAATAAAAT TCTTATGTCT TTTGATGCAC TTAGTTTTTG TTACCTAAGT
                                                        mcrI                                                muI
5321 ATTTTGGAAA AAGGCAATGA AATTAGACTA TGATCCAAAT GTAAAAGTTC AAATGATTCG ACCGAAAAAT AAATATAAAT CGGATATACA ATCGGCAATT
     TAAAACCTTT TTCCGTTACT TTAATCTGAT ACTAGGTTTA CATTTTCAAG TTTACTAAGC TGGCTTTTTA TTTATATTTA GCCTATATGT TAGCCGTTAA
                                                               apoI        psp1406I
5421 GACGAAACTG TGTAAAGGAT ACGGATTTTA TGAACCGATGA TGAAGAAAAG GTTGTCTGA CAAACAGACT TTTGGAGGAA GGTTTACACC
     CTGCTTTGAC ACATTTCCTA TGCCTAAAAT ACTGGCTACT ACTTCTTTTC TTAAACTTTG CAAACAGACT AAACCTCCTT CCAAATGTGG
5521 GTAAAAGGTT AATCTCCTAT GGTGGTTTGT TAAAAGAAAT ACATAAAAAA TTAAACCTTG ATGACACAGA AGAAGGCGAT TTGATTCATA CAGATGATGA
     CATTTTCCAA TTAGAGGATA CCACCAAACA ATTTTCTTTA TGTATTTTTT AATTTGGAAC TACTGTGTCT TCTTCCGCTA AACTAAGTAT GTCTACTACT
5621 CGAAAAAGCC GATGAAGATG GATTTTCTAT TATTGCAATG AACGGAAAAA TTATTTTATT AAAGAGTAGT TCAACAAACG GGCCAGTTTG
     GCTTTTTCGG CTACTTCTAC CTAAAAGATA ATAACGTTAC ACCTTAACCC TTGCCTTTTT AATAAAATAA TTTCTCATCA AGTTGTTTGC CCGGTCAAAC
                                                                                            hgiAI/aspHI
                                                                                            bsp1286
                                                             bpuAI                          bsiHKAI
                                                             bbsI    aseI/asnI/vspI         bmyI           sspI
5721 TTGAAGATTA GATGCTATAA TTGTTATTAA AAGGATTGAA TTCCTAACTT GAAGACGAGT TATTAATAGC TGAATAAGAA CGGTGCTCTC CAAATATTCT
     AACTTCTAAT CTACGATATT AACAATAATT TTCCTAACTT CTTCTGCTCA ATAATTATCG ACTTATTCTT GCCACGAGAG GTTTATAAGA
                                                                                                      rcaI
                                                                                                      bspHI
5821 TATTTAGAAA AGCAAATCTA AAATTATCTG AAAAGGGAAT GAGAATAGTG AATGGACCAA TAATAATGAC TAGAGAAGAA AGAATGAAGA TTGTTCATGA
     ATAAATCTTT TCGTTTAGAT TTTAATAGAC TTTTCCCTTA CTCTTATCAC TTACCTGGTT ATTATTACTG ATCTCTTCTT TCTTACTTCT AACAAGTACT
```

FIG. 6H

```
                                                                    hgiJII
                                                                    eco0109I/draII
                                                                    bsp1286
                                                                    bsp120I
                                                                    bmyI
                                                                    banII
                                                                    apaI
                                                                                        xmnI
                                                                                        earI/ksp632I
                                               cfr10I                                   asp700
                                               bsaWI                       apoI
                                               ageI
                       hincII/hindII
     sspI
5921 AATTAAGGAA CGAATATTGG ATAAATATGG GGATGATGTT AAGGCTATTG GTGTTTATGG CTCTCTTGGT CGTCAGACTG ATGGGCCCTA TTCGGATATT
     TTAATTCCTT GCTTATACCT TATTTATACC CCTACTACAA TTCCGATAAC CACAAATACC GAGAGAACCA GCAGTCTGAC TACCCGGGAT AAGCCTATAA 6021 GAGATGATGT GTGTCATGTC AACAGAGGAA GCCATGAATG GACAACCGGT GAGTGGAAGG TGGAAGTGAA TTTTGATAGC GAAGAGATTC
     CTCTACTACA CACAGTACAG TTGTCTCCTT CGGTACTTAC CTGTTGGCCA CTCACCTTCC ACCTTCACTT AAAACTATCG CTTCTCTAAG
     ppu10I                       eaeI
     nsiI/avaIII                  cfrI
6121 TACTAGATTA TGCATCCTCAG GTGGAATCAG ATTGGCCGCT TACACATGGT CAATTTTTCT CTATTTTGCC GATTTATGAT TCAGGTGGAT ACTTAGAGAA
     ATGATCTAAT ACGTAGAGTC CACCTTAGTC TAACCGGCGA ATGTGTACCA GTTAAAAAGA GATAAAACGG CTAAATACTA AGTCCACCTA TGAATCTCTT
                                              bsp1286                       sapI
                                              bmyI                          earI/ksp632I
                                   psp1406I                                                 hgiCI
6221 AGTGTATCAA ACTGCTAAAT CGGTAGAAGC CACGATGCGA TTTGTGCCCT TATCGTAGAA GAGCTGTTTG AATATGCAGG CAAATGGCGT
     TCACATAGTT TGACGATTTA GCCATCTTCG GTGCTACGCT AAACACGGGA ATAGCATCTT CTCGACAAAC TTATACGTCC GTTTACCGCA
                                                                                            banI
     sspI                                         bsp1407I                                  bspMI
6321 AATATTCGTG TGCAAGGACC GACAACATTT CTACCATCCT TGACTGTACA GGTAGCAATG GCAGGTGCCA TGTTGATTGG TCTGCATCAT CGCATCTGTT
     TTATAAGCAC ACGTTCCTGG CTGTTGTAAA GATGGTAGGA ACTGACATGT CCATCGTTAC CGTCCACGGT ACAACTAACC AGACGTAGTA GCGTAGACAA
                                              bstYI/xhoII
                bstYI/xhoII                                                                           hincII/hindII
     haeII       bglII          eco57I
     eco47III                                                                                         hincII/hindII
6421 ATACGACGAG CGCTTCGGTC TTAACTGAAG CAGTTAAGCA ATCAGATCTT CCTTCAGGTT GTGCCAGTTC ATGACCATCT GTAATGTCTG GTCAACTTTC
     TATGCTGCTC GCGAAGCCAG AATTGACTTC GTCAATTCGT TAGTCTAGAA GGAAGTCCAA CACGGTCAAG TACTGGTAGA CATTACAGAC CAGTTGAAAG
                                   apoI
6521 CGACTCTGAG AAACTTCTGG AATCGCTAGA GAATTTCTGG AATGGGATTC AGGAGTGGAC AGAACGACAC GGATATATAG TGGATGTGTC AAAACGCATA
     GCTGAGACTC TTTGAAGACC TTAGCGATCT CTTAAAGACC TTACCCTAAG TCCTCACCTG TCTTGCTGTG CCTATATATC ACCTACACAG TTTTGCGTAT
                                              snaBI
                                              bsaAI
6621 CCATTTGAA CGATGACCTC TAATAATTGT GGTTACGTAT TTATTAACTT CTCCTAGTAT TAGTAATTAT CATGGCTGTC ATGGCGCATT
     GGTAAACTT GCTACTGGAG ATTATTAACA CCAATGCATA AATAATTGAA GAGGATCATA ATCATTAATA GTACCGACAG TACCGCGTAA
```

FIG. 6I

```
                                                                     aseI/asnI/vspI                aseI/asnI/vspI
6721  AACGGAATAA AGGGTGTGCT TAAATCGGGC CATTTTGCGT AATAAGAAAA AGATTAATT ATGAGCGAAT TGAATTAATA ATAAGGTAAT AGATTTACAT
      TTGCCTTATT TCCCACACGA ATTAGCCCG  GTAAAACGCA TTATTCTTTT TCCTAATTAA TACTCGCTTA ACTTAATTAT TATTCCATTA TCTAAATGTA 6821  TAGAAAATGA AAGGGATTT  TATGCGTGAG TCTATCCCCG CAATAGTTAC CCTTATATTC AAGATAAGAA AGAAAAGGAT TTTTCGCTAC
      ATCTTTTACT TTCCCCTAAA ATACGCACTC AGATAGGGCC GTTATCAATG GGAATAATAG TTCTATTCTT TCTTTTCCTA AAAAGCGATG
      ahaIII/draI
6921  GCTCAAATCC TTTAAAAAAA CACAAAAGAC AATGTGGTCT TTATTCTTCA ACTAAAGCAC CCATTAGTTC AACAAACGAA AATTGGATAA
      CGAGTTTAGG AAATTTTTTT GTGTTTTCTG TTACACCAGA AATAAGAAGT TGATTTCGTG GGTAATCAAG TTGTTTGCTT TTAACCTATT
            ahaIII/draI      sspI                                                                 apoI
7021  AGTGGGATAT TTTTAAAATA TATATTTATG TTACAGTAAT ATTGACTTTT AAAAAAGGAT TGATTCTAAT GAAGAAAGCA GACAAGTAAG CCTCCTAAAT
      TCACCCTATA AAAATTTTAT ATATAAATAC AATGTCATTA TAACTGAAAA TTTTTTCCTA ACTAAGATTA CTTCTTTCGT CTGTTCATTC GGAGGATTTA
      apoI                                              munI   earI/ksp632I            apoI
7121  TCACTTTTAGA TAAAAATTTA GGAGGCATAT CAAATGAACT TTAATAAAAT TGATTTAGAC AATTGGAAGA GAAAAGAGAT ATTTAATCAT TATTTGAACC
      AGTGAAATCT ATTTTTAAAT CCTCCGTATA GTTTACTTGA AATTATTTTA ACTAAATCTG TTAACCTTCT CTTTTCTCTA TAAATTAGTA ATAAACTTGG 7221  AACAAACGAC TTTTAGTATA ACCACAGAAA TTGATATTAG TGTTTTATAC CGAAACATAA AACAAGAAGG ATATAAATTT TACCCTGCAT TTATTTTCTT
      TTGTTTGCTG AAAATCATAT TGGTGTCTTT AACTATAATC ACAAAAATATG GCTTTGTATT TTGTTCTTCC TATATTTAAA ATGGGACGTA AATAAAAGAA 7321  AGTGACAAGG GTGATAAACT CAAATACAGC TTTTAGAACT GGTTACAATA GCGACGGAGA GTTAGGTTAT TGGGATAAGT TAGAGCCACT TTATACAATT
      TCACTGTTCC CACTATTTGA GTTTATGTCG AAAATCTTGA CCAATGTTAT CGCTGCCTCT CAATCCAATA ACCCTATTCA ATCTCGGTGA AATATGTTAA
                                                  xmnI
                                                  asp700
7421  TTTGATGGTG TATCTAAAAC ATTCTCTGGT ATTTGGACTC TGACTTCAAA GAGTTTATG ATTTATACCT TTCTGATGTA GAGAAATATA
      AAACTACCAC ATAGATTTTG TAAGAGACCA TAAACCTGAG ACTGAAGTTT CTCAAATAC TAAATATGGA AAGACTACAT CTCTTTATAT
                                                                  styI
                                                                  ncoI
                                                                  dsaI
7521  ATGGTTCGGG GAAATTGTTT CCCAAAACAC CTATACCTGA AAATGCTTTT TCTCTTTCTA TTATTCCATG GACTTCATTT ACTGGGTTTA ACTTAAATAT
      TACCAAGCCC CTTTAACAAA GGGTTTTGTG GATATGGACT TTTACGAAAA AGAGAAAGAT AATAAGGTAC CTGAAGTAAA TGACCCAAAT TGAATTTATA
                                                               apoI aseI/asnI/vspI
7621  CAATAATAAT AGTAATTACC TTCTACCCAT TATTACAGCA GGAAAATTCA TTAATAAAGG TAATTCAATA TATTTACCGC TATCTTTACA GGTACACATCAT
      GTTATTATTA TCATTAATGG AAGATGGGTA ATAATGTCGT CCTTTTAAGT AATTATTTCC ATTAAGTTAT ATAAATGGCG ATAGAAATGT CCATGTAGTA
```

FIG. 6J

```
           mamI                                           stuI
           bsaBI                                          haeI
7721 TCTGTTTGTG ATGGTTATCA TGCAGGATTG TTTTATGAACT CTATTCAGGA ATTGTCAGAT AGGCCTAATG ACTGGCTTTT ATAATATGAG ATAATGCCGA
     AGACAAACAC TACCAATAGT ACGTCCTAAC AAATACTTGA GATAAGTCCT TAACAGTCTA TCCGGATTAC TGACCGAAAA TATTATACTC TATTACGGCT mamI[dam-]
                                                                                             bsaBI[dam-]
                                bspMI                                                        bstYI/xhoII
                                                                                             gsuI/bpmI
7821 CTGTACTTTT TACAGTCGGT TTTCTAATGT CACTAACCTG CCCCGTTAGT TGAAGAAGGT TTTTATATTA CAGCTCCAGA TCCATATCCT TCTTTTTCTG
     GACATGAAAA ATGTCAGCCA AAAGATTACA GTGATTGGAC GGGGCAATCA ACTTCTTCCA AAAATATAAT GTCGAGGTCT AGGTATAGGA AGAAAAAGAC munI
7921 AACCGACTTC TCCTTTTTCG CTTCTTTATT CCAATTGCTT TATTGACGTT GAGCCTCGGA ACCXTATAG TGTGTTATAC TTTACTTGGA AGTGGTTGCC
     TTGGCTGAAG AGGAAAAAGC GAAGAAATAA GGTTAACGAA ATAACTGCAA CTCGGAGCCT TGGG?ATATC ACACAATATG AAATGAACCT TCACCAACGG ndeI                          bsmI
8021 GGAAAGAGCG AAAATGCCTC ACATTGTGC CACCTAAAAA GGAGCGATTT ACATATGAGT TATGCAGTTT GTAGAATGCA AAAAGTGAAA TCAGGATCX
     CCTTTCTCGC TTTTACGGAG TGTAAACACG GTGGATTTTT CCTCGCTAAA TGTATACTCA ATACGTCAAA CATCTTACGT TTTTCACTTT AGTCCTAG?
```

FIG.6K

```
Val Arg Gly Lys Lys Val Trp Ile Ser Leu Leu Phe Ala Leu Ala
-107     -105                -100                     -95
Leu Ile Phe Thr Met Ala Phe Gly Ser Thr Ser Ser Ala Gln Ala
            -90             -85                 -80
Ala Gly Lys Ser Asn Gly Glu Lys Lys Tyr Ile Val Gly Phe Lys
        -75             -70                     -65
Gln Thr Met Ser Thr Met Ser Ala Ala Lys Lys Lys Asp Val Ile
        -60             -55                     -50
Ser Glu Lys Gly Gly Lys Val Gln Lys Gln Phe Lys Tyr Val Asp
        -45             -40                     -35
Ala Ala Ser Ala Thr Leu Asn Glu Lys Ala Val Lys Glu Leu Lys
        -30             -25                     -20
Lys Asp Pro Ser Val Ala Tyr Val Glu Glu Asp His Val Arg His
        -15             -10                     -5
Lys Arg Ala Gln Ser Val Pro Tyr Gly Val Ser Gln Ile Lys Ala
         1               5                      10
Pro Ala Leu His Ser Gln Gly Tyr Thr Gly Ser Asn Val Lys Val
         15              20                     25
Ala Val Ile Asp Ser Gly Ile Asp Ser Ser His Pro Asp Leu Lys
         30              35                     40
Val Ala Gly Gly Ala Ser Met Val Pro Ser Glu Thr Asn Pro Phe
         45              50                     55
Gln Asp Asn Asp Ser His Gly Thr His Val Ala Gly Thr Val Ala
         60              65                     70
Ala Leu Asn Asn Ser Ile Gly Val Leu Gly Val Ala Pro Ser Ala
         75              80                     85
Ser Leu Tyr Ala Val Lys Val Leu Gly Ala Asp Gly Ser Gly Gln
         90              95                     100
Asp Ser Trp Ile Ile Asn Gly Ile Glu Trp Ala Ile Ala Asn Asn
         105             110                    115
Met Asp Val Ile Asn Met Ser Leu Gly Gly Pro Ser Gly Ser Ala
         120             125                    130
Ala Leu Lys Ala Ala Val Asp Lys Ala Val Ala Ser Gly Val Val
         135             140                    145
Val Val Ala Ala Ala Gly Asn Glu Gly Thr Ser Gly Ser Ser Ser
         150             155                    160
Thr Val Asp Tyr Pro Gly Lys Tyr Pro Ser Val Ile Ala Val Gly
         165             170                    175
Ala Val Asp Ser Ser Asn Gln Arg Ala Ser Phe Ser Ser Val Gly
         180             185                    190
Pro Glu Leu Asp Val Met Ala Pro Gly Val Ser Ile Gln Ser Thr
         195             200                    205
Leu Pro Gly Asn Lys Tyr Gly Ala Tyr Asn Gly Thr Ser Met Ala
         210             215                    220
Ser Pro His Val Ala Gly Ala Ala Leu Ile Leu Ser Lys His
         225             230                    235
Pro Asn Trp Thr Asn Thr Gln Val Arg Ser Ser Leu Glu Asn Thr
         240             245                    250
Thr Thr Lys Leu Gly Asp Ser Phe Tyr Tyr Gly Lys Gly Leu Ile
         255             260                    265
Asn Val Gln Ala Ala Ala Gln
         270             275
```

FIG. 8

SUBTILISIN VARIANTS CAPABLE OF CLEAVING SUBSTRATES CONTAINING BASIC RESIDUES

This application is a continuation-in-part of application Ser. No. 08/398,028 filed Mar. 3, 1995.

FIELD OF THE INVENTION

This invention relates to subtilisin variants having altered specificity from wild-type subtilisins. Specifically, the subtilisin variants are modified so that they efficiently and selectively cleave substrates containing basic residues. The invention further relates to the DNA encoding these novel polypeptides, as well as the recombinant materials and methods for producing these subtilisin variants. In a particular aspect, the present invention provides for processes for cleaving protein substrates containing basic residues.

BACKGROUND OF THE INVENTION

Site-specific proteolysis is one of the most common forms of post-translational modifications of proteins (for review see Neurath, H. (1989) Trends Biochem. Sci., 14:268). In addition, proteolysis of fusion proteins in vitro is an important research and commercial tool (for reviews see Uhlen, M. and Moks, T. (1990) Methods Enzymol., 185:129–143; Carter, P. (1990) in Protein Purification: From Molecular Mechanisms to Large-Scale Processes, M. R. Landisch, R. C. Wilson, C. D. Painton, S. E. Builder, Eds. (ACS Symposium Series 427, American Chemical Society, Washington, D.C.), Chap. 13, p.181–193; and Nilsson, B. et al. (1992) Current Opin. Struct. Biol., 2:569). Expressing a protein of interest as a fusion protein facilitates purification when the fusion contains an affinity domain such as glutathione-S-transferase, Protein A or a poly-histidine tail. The fusion domain can also facilitate high level expression and/or secretion. To liberate the protein product from the fusion domain requires selective and efficient cleavage of the fusion protein. Both chemical and enzymatic methods have been proposed (see references above). Enzymatic methods are generally preferred as they tend to be more specific and can be performed under mild conditions that avoid denaturation or unwanted chemical side-reactions. A number of natural and even designed enzymes have been applied for site-specific proteolysis. Although some are generally more useful than others (Forsberg, G., Baastrup, B., Rondahl, H., Holmgren, E., Pohl, G., Hartmanis, M. and Lake, M. (1992) J. Prot. Chem., 11:201–211), no one is applicable to every situation given the sequence requirements of the fusion protein junction and the possible existence of protease sequences within the desired protein product. Thus, an expanded array of sequence specific proteases, analogous to restriction endonucleases, would make site-specific proteolysis a more widely used method for processing fusion proteins or generating protein/peptide fragments either in vitro or in vivo.

The processing of prohormones by the KEX2-related family of serine endoproteases illustrates one of the most precise proteolytic events found in nature (for reviews see Steiner, D. F.,Smeekens, S. P., Ohagi, S. and Chan, S. J. (1992)J. Biol. Chem., 267, 23435–23438 and Smeekens, S. P. (1993) Bio/Technology 11, 182–186). This family of proteases, that includes the yeast KEX2 and the mammalian PC2, PC3 and furin enzymes, are homologous to the bacterial serine protease subtilisin (Kraut, J. (1977) Annu. Rev. Biochem.., 46:331–358). Subtilisin has a broad substrate specificity that reflects its role as a scavenger protease. In contrast, these eukaryotic enzymes are very specific for cleaving substrates containing two basic residues and thus well-suited for site-specific proteolysis.

All of these eucaryotic enzymes strongly require Arg at the P1 position, and either Arg, Lys or Pro at the P2 position of peptide substrates. The prohormone convertases from higher eukaryotes such as furin, PC2, and PC3 also have an absolute requirement for Arg at the P4 position (Bresnahan, P. A., Leduc, R., Thomas, L., Thorner, J., Gibson, H. L., Brake, A. J., Barr, P. J. and Thomas, G. (1990) J. Cell. Biol. 111, 2851; Wise, R. J., Baar, P. J., Wong, P. A., Kiefer, M. C., Brake, A. J., and Kaufman, R. J. (1990) Proc. Natl. Acad. Sci. USA 87, 9378–9382.; Hosaka, M., Nagahama, M., Kim, W.-S., Watanabe, T., Hatsuzakawa, K., Ikemizu, J., Murakami, K., and Nakayama, K. (1991) J. Biol. Chem. 266, 12127–12130.;Matthews, D. J., Goodman, L. J., Gorman, C. M., and Wells, J. A. (1994) Protein Science 3, 1197–1205).

Despite the very narrow specificity of the pro-hormone processing enzymes, in some cases they are capable of rapid cleavage of target sequences. For example, the $k_{cat}$/Km ratio for KEX2 to cleave a good substrate (e.g. acetyl-pMYRK-MCA) is $1.1 \times 10^7$ $M^{-1}s^{-1}$ (Brenner, C., and Fuller, R. S. (1992) Proc. Natl. Acad. Sci. USA, 89:922–926) compared to $3 \times 10^5$ for subtilisin cleaving a good substrate (e.g. suc-AAPF-pNA) (Estell, D. A., Graycar, T. P., Miller, J. V., Powers, D. B., Burnier, J. P., Ng, P. G. and Wells, J. A. (1986) Science, 233:659–663).

However, the eukaryotic proteases are expressed in small amounts (Bravo, D. B., Gleason, J. B., Sanchez, R. I., Roth, R. A., and Fuller, R. S. (1994) J. Biol. Chem., 269:25830–25837 and Matthews, D. J., Goodman, L. J., Gorman, C. M., and Wells, J. A. (1994) Protein Science, 3:1197–1205) making them impractical to apply presently to processing of fusion proteins in vitro. Subtilisin BPN' however, can be expressed in large amounts (Wells, J. A., Ferrari, E., Henner, D. J., Estell, D. A. and Chen, E. Y. (1983) Nucl. Acids Res., 11:7911–7929)

Extensive protein engineering studies of subtilisin, and especially subtilisin BPN', have identified several residues in the S1 and S2 active site of the enzyme where amino acid substitutions lead to large changes in substrate specificity (Wells, J. A., and Estell, D. A., (1988) Trends Biochem. Sci., 13:291–297; Carter, P., et al., (1989) PROTEINS:Structure, Function, and Genetics, 6:240–248). X-ray crystal structures of subtilisin containing bound transition state analogues (Wright, C. S., Alden, R. A. and Kraut, J. (1969) Nature, 221:235–242; McPhalen, C. A. and James, N. G. (1988) Biochemistry, 27:6582–6598; Bode, W., Papamokos, E., Musil, D., Seemueller, U. and Fritz, M. (1986) EMBO J., 5:813–818; and Bott, R., Ultsch, M., Kossiakoff, A., Graycar, T., Katz, B. and Power, S. (1988) J. Biol. Chem., 263:7895–7906) can be used to locate active site residues that are in close proximity to side chains at key positions in substrate peptides (Wells, J. A., (1987) Proc. Natl. Acad. Sci. USA 84:1219–1223). Consideration of electrostatic interactions between charged peptide substrates and subtilisin can be used to tailor the substrate binding cleft of the subtilisin BPN' to favor complementary charged substrates (Wells, J. A., et al., (1987) Proc. Natl. Acad. Sci., USA, 84:1219–1223). Previous work has shown that replacement of residues at position 156 and 166 in the S1 binding site of subtilisin BPN' with various charged residues leads to improved specificity for complementary charged substrates.

A substantial amount of protein engineering has been applied to the specificity determinants of the S4 subsite of subtilisin BPN' in efforts to alter specificity for P4 substrates (Eder, J., Rheinnecker, M., and Fersht, A. R. (1993) FEBS Lett 335, 349–352; Rheinnecker, M., Baker, G., Eder, J., and Fersht, A. R. (1993) Biochemistry 32, 1199–1203; Rheinnecker, M., Eder, J.,Pandey, P. S., and Fersht, A. R. (1994) Biochemistry 33, 221–225). However, the mutations introduced consisted entirely of hydrophobic substitutions, thus preserving the overall hydrophobic substrate preference in the site.

Previous attempts to introduce, remove or reverse charge specificity in enzyme active sites have been met with considerable difficulty. This has generally been attributed to a lack of stabilization of the introduced charge or enzyme-substrate ion pair complex by the wild-type enzyme environment (Hwang, J. K. and Warshel, A. (1988) Nature, 334:270–272). For example, Stennicke et. al (Stennicke, H. R.; Ujje, H. M.; Christensen, U.; Remington, S. J.; and Breddam (1994) Prot. Eng. 7:911–916) made acidic (D/E) mutations at five residues in the P1' binding of carboxypeptidase Y in an attempt to change the P1' preference from Phe to Lys/Arg. Only the L272D and L272E mutations were found to alter the specificity in the desired direction, up to 1.5-fold preference in Lys/Arg over Phe, and the others simply resulted in less active enzymes having substrate preferences similar to wild-type. In the case of trypsin, a protease that is highly specific for basic P1 residues, recruitment of chymotrypsin-like (hydrophobic P1) specificity required not only mutations of the ion pair-forming Asp 189 to Ser, but also transplantation of two more distant surface loops from chymotrypsin (Graf, L., Jancso, A., Szilagyi, L., Hegyi, G., Pinter, K., Naray-Szabo, G., Hepp, J., Medzihradszky, K., and Rutter, W. J., Proc. Natl. Acad. Sci. USA (1988) 85:4961–4965 and Hedstrom, L., Szilagyi, L., and Rutter, W. J., Science (1992) 255:1249–1253).

In the present work, we have also verified that relatively low specificity is gained by introducing single ion-pairs between enzyme and substrate. However, when two or more choice ionic interactions were simultaneously engineered into subtilisin BPN', the resulting variants had higher specificity for basic residues in each of the subsites due to a non additive effect.

Accordingly, it is an object to produce a subtilisin variant with basic specificity for use in processing pro-proteins made by recombinant techniques.

SUMMARY OF THE INVENTION

The present invention provides for subtilisin variants with altered substrate specificity. Preferred subtilisin variants are highly specific for the efficient cleavage of substrates containing basic residues. The subtilisin variants have a substrate specificity which is substantially different from the substrate specificity of the precursor subtilisin from which the amino acid sequence of the variant is derived. The amino acid sequence of the subtilisin variants are derived by the substitution of one or more amino acids of a precursor subtilisin amino acid sequence.

In a preferred aspect of the present invention, the subtilisin variants of the present invention are specific for the cleavage of protein substrates containing basic amino acid residues at substrate positions P1, P2 and P4. According to this aspect of the present invention subtilisin variants having amino acid substitutions at positions corresponding to amino acid positions 62, 104 and 166 of subtilisin BPN' produced by Bacillus amyloliquefaciens are preferred. Accordingly, subtilisin variants are provided wherein amino acids 62, 104 and 166 of subtilisin BPN' are substituted with an acidic amino acids. Preferably the acidic amino acid is Asp or Glu, and most preferably Asp.

Preferred substrates for the subtilisin variants according to this aspect of the present invention contain either Lys (K) or Arg (R) at substrate positions P2 and P1, practically any residue at P3, and preferably either Lys or Arg at P4, and again practically any residue at P5. Thus an exemplary good substrate would contain -Asn-Arg-Met-Arg-Lys- (SEQ ID NO: 76) at -P5-P4-P3-P2-P1- respectively. Additionally, good substrates would not have Pro at P1', P2', or P3' nor would Ile be present at P1'.

According to a second aspect of the present invention the subtilisin variants are capable of cleaving protein substrates having basic residues at positions P1 and P2. According to this aspect of the present invention subtilisin variants having amino acid substitutions at positions corresponding to amino acid positions 62, and 166 of subtilisin BPN' produced by Bacillus amyloliquefaciens are preferred. The preferred subtilisin variants having substrate specificity for dibasic substrates have an acidic amino acid residue at residue position 62 of subtilisin naturally produced by Bacillus amyloliquefaciens. In a preferred embodiment, the naturally occurring Asn at residue position 62 of subtilisin BPN' is preferably substituted with an acidic amino acid residue such as Glu or Asp, and most preferably Asp. The preferred subtilisin variants, having substrate specificity for substrates having dibasic amino acid residues, additionally have an acidic residue, Asp or Glu, at residue position 166 of subtilisin BPN'. Thus, the subtilisin BPN' variant containing substitution of amino acids 62 and 166 with acidic amino acids Glu or Asp are preferred. In particular, a subtilisin variant having amino acid Asp at positions 62 and 166 is preferred (subtilisin BPN' variant N62D/G166D). The subtilisin variants according to this aspect of the invention may be used to cleave substrates containing dibasic residues such as fusion proteins with dibasic substrate linkers and processing hormones or other proteins (in vitro or in vivo) that contain dibasic cleavage sites.

Preferred substrates for the subtilisin BPN' variant N62D/G166D contain either Lys (K) or Arg (R) at substrate positions P2 and P1, practically any residue at P3, a non-charged hydrophobic residue at P4, and again practically any residue at P5. Thus an exemplary good substrate would contain -Asn-Leu-Met-Arg-Lys- (SEQ ID NO: 35) at -P5-P4-P3-P2-P1- respectively. Additionally, good substrates would not have Pro at P1', P2', or P3' nor would Ile be present at P1'.

The invention also includes mutant DNA sequences encoding such subtilisin variants. These mutant DNA sequences are derived from a precursor DNA sequence which encodes a naturally occurring or recombinant precursor subtilisin. The mutant DNA sequence is derived by modifying the precursor DNA sequence to encode the substitution(s) of one or more amino acids encoded by the precursor DNA sequence. These recombinant DNA sequences encode mutants having an amino acid sequence which does not exist in nature and a substrate specificity which is substantially different from the substrate specificity of the precursor subtilisin encoded by the precursor DNA sequence.

Further the invention includes expression vectors containing such mutant DNA sequences as well as host cells transformed with such vectors which are capable of expressing the subtilisin variants.

The invention also provides for a process for cleaving a polypeptide such as a fusion protein containing a substrate linker represented by the formula:

P4-P3-P2-P1 wherein P4 is a basic amino acid or a large hydrophobic amino acid such as Leu or Met; P3 is an amino acid selected from the naturally occurring amino acids; P2 is a basic amino acid; and P1 is a basic amino acid. The process includes the step of subjecting the polypeptide to the subtilisin variants described herein under conditions such that the subtilisin variant cleaves the polypeptide.

BRIEF DESCRIPTION OF THE FIGURES

Figure 6A:
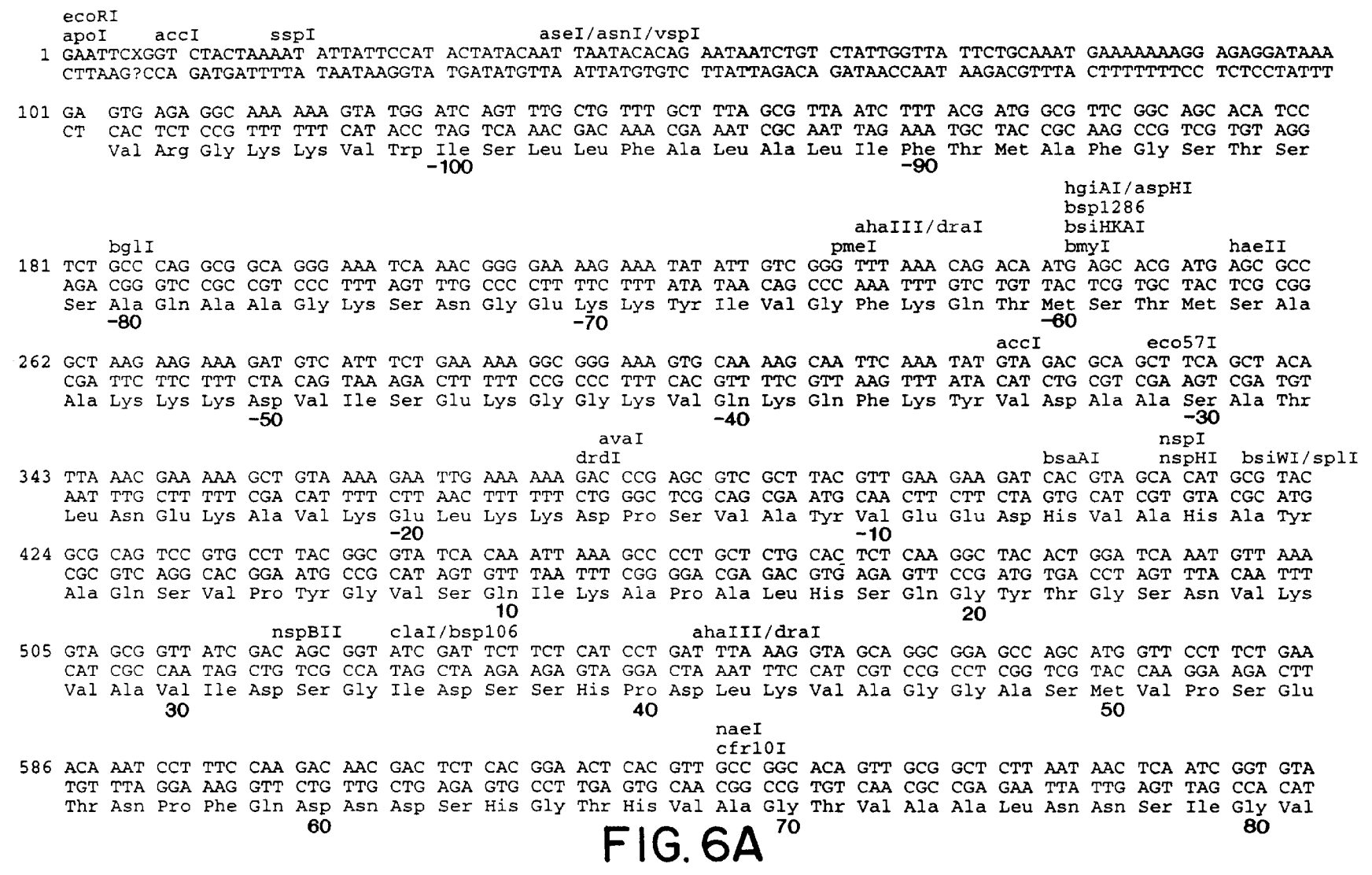
Figure 6B:
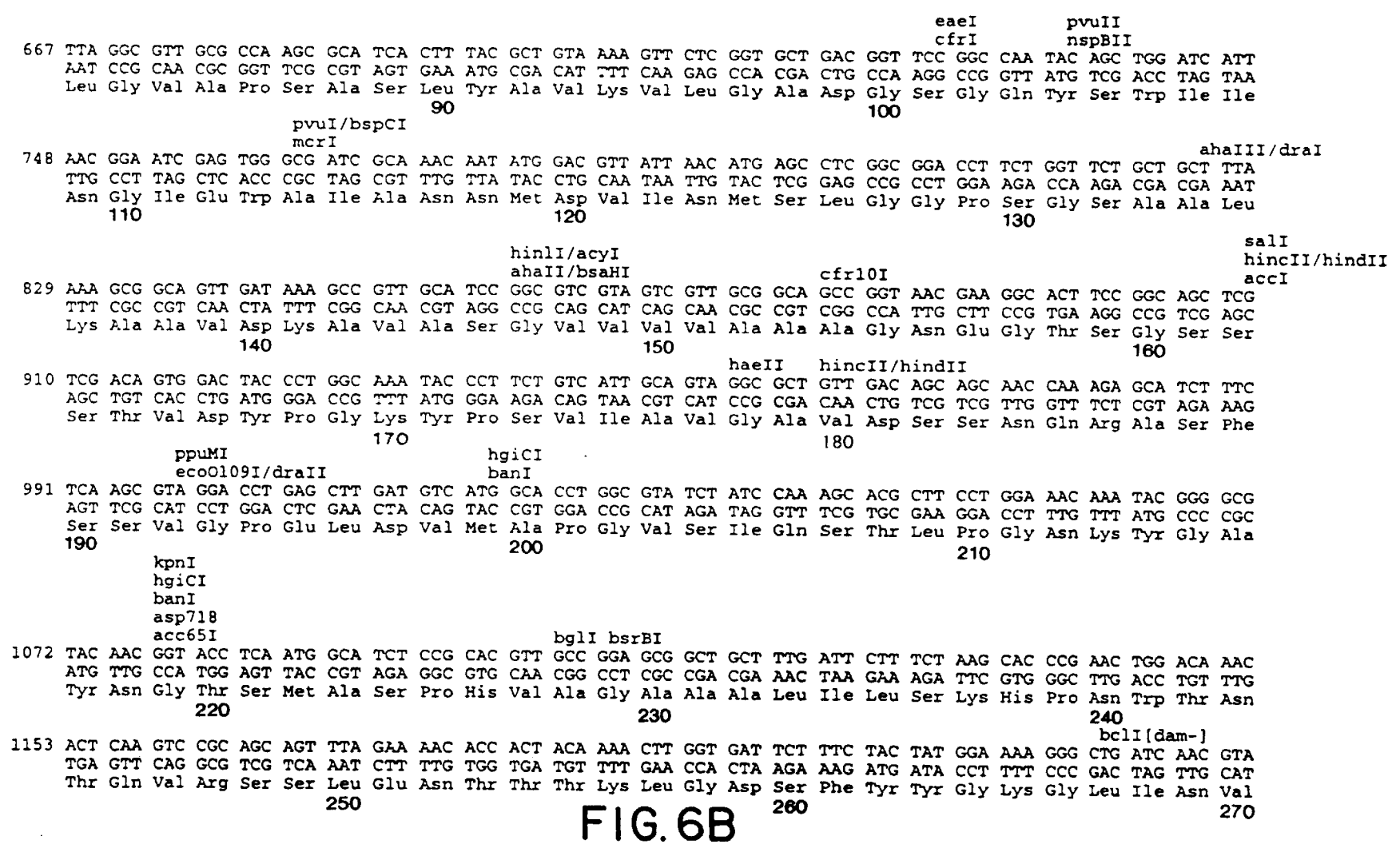
Figure 6C:
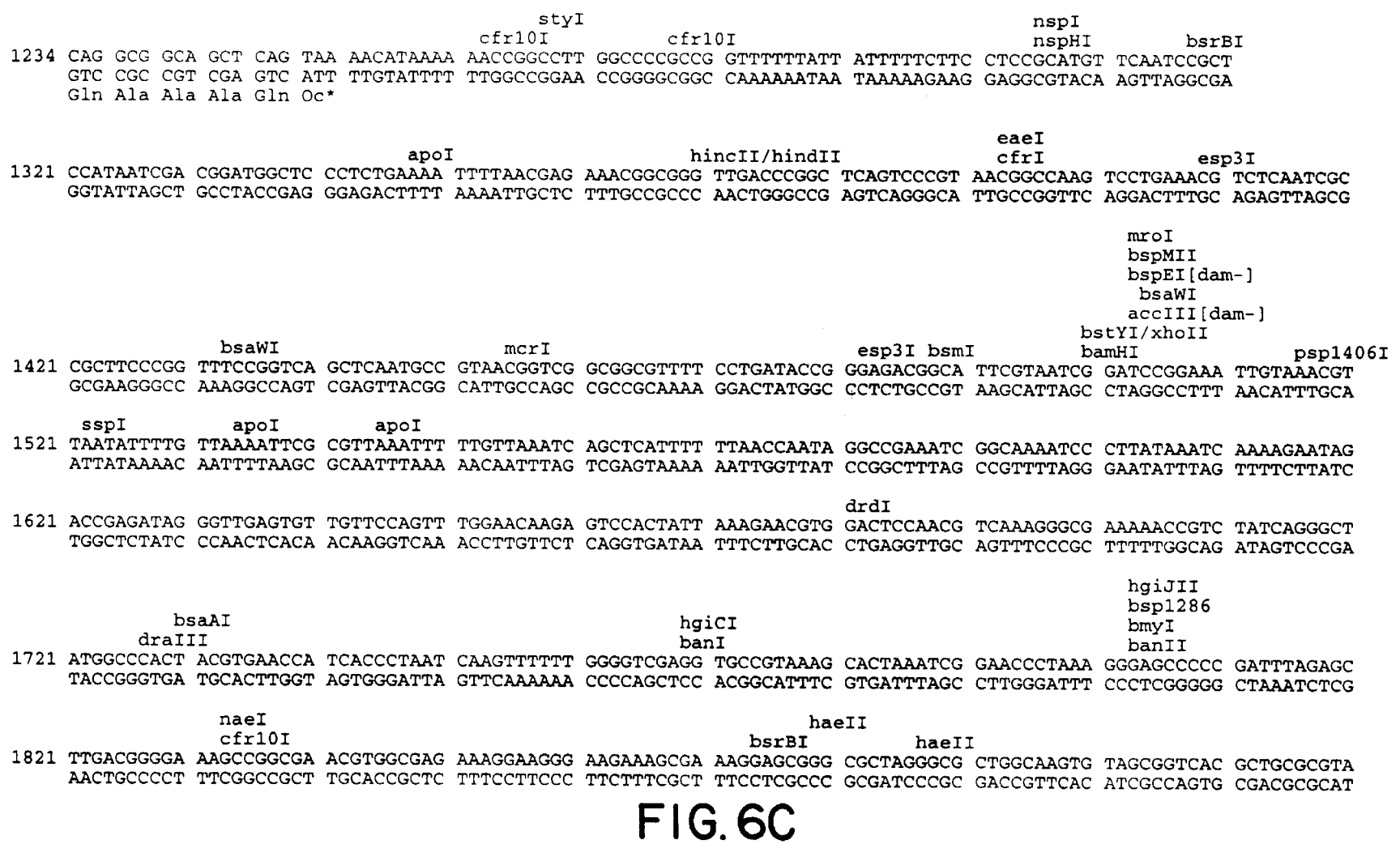

FIGS. 6A–6K. (Collectively referred to herein as FIG. 6). DNA sequence of the phagemid pSS5 containing the N62D/G166D double mutant subtilisin BPN' gene (SEQ ID NO: 1), and translated amino acid sequence for the mutant prepro-subtilisin (SEQ ID NO: 2). The pre region is comprised of residues −107 to −78, the pro of residues −77 to −1, and the mature enzyme of residues +1 to +275 (SEQ ID NO: 72). Also shown are restriction sites recognized by endonucleases that require 6 or more specific bases in succession.

FIG. 8. DNA sequence of the N62D/Y104D/G166D triple mutant (SEQ ID NO:74) as well as the translated amino acid sequence (SEQ ID NO:75). The preregion is comprised of residues −107 to −78, the pro residues −77 to −1 and the mature enzyme +1 to +275. The proregion reflects the changes, A(−4)R/A(−2)K/Y(−1)R made in the wild-type processing site to affect expression.

DETAILED DESCRIPTION OF THE INVENTION

DEFINITIONS

Figure 1:
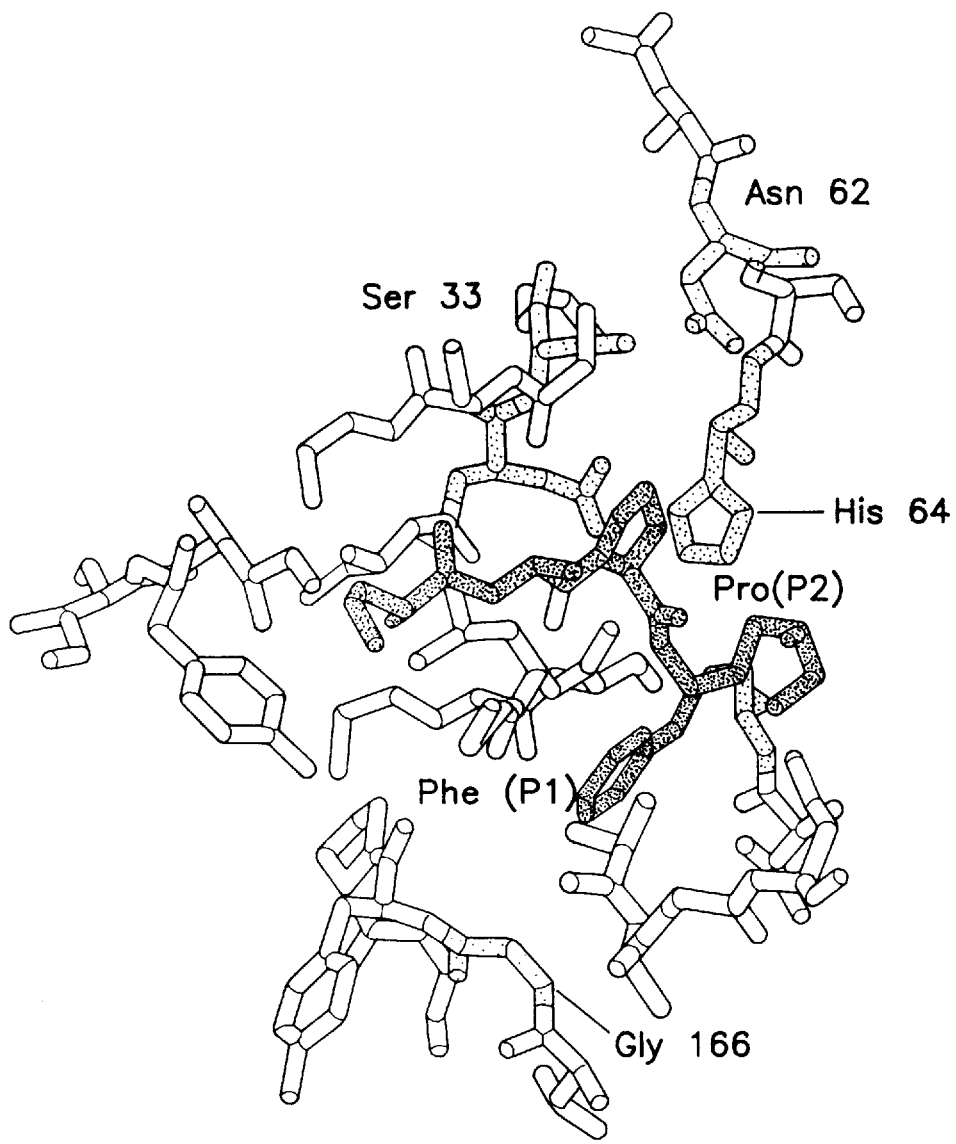
FIG. 1. Structure of a succinyl-Ala-Ala-Pro-BoroPhe (SEQ ID NO: 69) inhibitor bound to the active site of subtilisin BPN' showing the S2 and S1 binding pocket residues subjected to mutagenesis.

Terms used in the claims and specification are defined as set forth below unless otherwise specified.

The term amino acid or amino acid residue, as used herein, refers to naturally occurring L amino acids or residues, unless otherwise specifically indicated. The commonly used one- and three-letter abbreviations for amino acids are use herein (Lehninger, A. L., *Biochemistry*, 2d ed., pp. 71–92, Worth Publishers, N. Y. (1975)). Basic amino acids are Arg and Lys. Acidic amino acids are Asp and Glu.

Substrates are described in triplet or single letter code as Pn . . . P2-P1-P1'-P2' . . . Pn'. The "P1" residue refers to the position proceeding (i.e., N-terminal to) the scissile peptide bond (i.e. between the P1 and P1' residues) of the substrate as defined by Schechter and Berger (Schechter, I. and Berger, A., Biochem. Biophys. Res. Commun. 27: 157–162 (1967)). Similarly, the term P1' is used to refer to the position following (i.e., C-terminal to) the scissile peptide bond of the substrate. Increasing numbers refer to the next consecutive position preceding (e.g., P2 and P3) and following (e.g., P2' and P3') the scissile bond. According to the present invention the scissile peptide bond is that bond that is cleaved by the subtilisin variants of the instant invention.

"Subtilisins," "precursor subtilisin" and the like are bacterial carbonyl hydrolases which generally act to cleave peptide bonds of proteins or peptides. As used herein, "subtilisin" means a naturally occurring subtilisin or a recombinant subtilisin. A series of naturally occurring subtilisins are known to be produced and often secreted by various bacterial species (Siezen, R. J., et al., (1991) Protein Engineering 4:719–737). Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however is histidine-aspartate-serine. Thus, subtilisins as used herein refer to a serine protease having the catalytic triad of subtilisin related proteases.

Generally, subtilisins are serine endoproteases' having molecular weights of about 27,500 which are secreted in large amounts from a wide variety of Bacillus species. The protein sequence of subtilisins have been determined from at least four different species of Bacillus (Markland, F. S., et al. (1971) in *The Enzymes*, ed. Boyer P. D., Acad Press, New York, Vol. III, pp. 561–608; and Nedkov, P. et al. (1983) Hoppe-Seyler's Z. Physiol. Chem. 364:1537–1540). The three-dimensional crystallographic structure of four subtilisins have been reported (BPN' from *Bacillus*

*amyloliquefaciens,* (SEQ ID NO: 90) Hirono et al. (1984) J. Mol. Biol. 178:389–413; subtilisn Carlesberg from *Bacillus licheniformis,* Bode et al., (1986) EMBO J., 5:813–818; thermitase from *Thermoactinomyces vulgaris,* Gros et al., (1989) J. Mol. Biol. 210:347–367; and proteinase K from *Tritirachium album,* Betzel, et al., (1988) Acta Crystallogr., B, 44:163–172). The three dimensional structure of subtilisin BPN' (from *B. amyloliquefaciens*) to 2.5 Å resolution has also been reported by Wright, C. S. et al. (1969) *Nature* 221:235–242 and Drenth, J. et al. (1972) *Eur. J. Biochem.* 26:177–181. These studies indicate that although subtilisin is genetically unrelated to the mammalian serine proteases, it has a similar fold and active site structure. The x-ray crystal structures of subtilisin containing covalently bound peptide inhibitors (Robertus, J. D., et al. (1972) Biochemistry 11:2439–2449), product complexes (Robertus, J. D., et al. (1972) Biochemistry 11:4293–4303), and transition state analogs (Matthews, D. A., et al. (1975) *J. Biol. Chem.* 250:7120–7126 and Poulos, T. L., et al. (1976) *J. Biol. Chem.* 251:1097–1103), which have been reported have also provided information regarding the active site and putative substrate binding cleft of subtilisins. In addition, a large number of kinetic and chemical modification studies have been reported for subtilisins (Phillip, M., et al. (1983) *Mol. Cell. Biochem.* 51:5–32; Svendsen, I. B. (1976) *Carlsberg Res. Comm.* 41:237–291 and Markland, F. S. Id.) as well as at least one report wherein the side chain of methione at residue 222 of subtilisin was converted by hydrogen peroxide to methionine-sulfoxide (Stauffer, D. C., et al. (1965) *J. Biol. Chem.* 244 5333–5338).

"Subtilisin variant," "subtilisin mutant" and the like refer to a subtilisin-type serine protease having a sequence which is not found in nature that is derived from a precursor subtilisin according to the present invention. The subtilisin variant has a substrate specificity different from the precursor subtilisin by virtue of amino acid substitutions within the precursor subtilisin amino acid sequence. The term is meant to include subtilisin variants in which the DNA sequence encoding the precursor subtilisin is modified to produce a mutant DNA sequence which encodes the substitution of one or more amino acids in the naturally occurring subtilisin amino acid sequence. Suitable methods to produce such modification include those disclosed in U.S. Pat. Nos. 4,760,025 and 5,371,008 and in EPO Publication No. 0130756 and 0251446.

A change in substrate specificity is defined as a difference between the $K_{cat}/Km$ ratio of the precursor subtilisin and the subtilisin variant. The $K_{cat}/Km$ ratio is a measure of catalytic efficiency. Subtilisin variants with increased or decreased $K_{cat}/Km$ ratios compared to the precursor subtilisin from which they were derived are described herein. Generally, the objective is to secure a variant having a greater, i.e. numerically larger, $K_{cat}/Km$ ratio for a given substrate. A greater $K_{cat}/Km$ ratio for a particular substrate indicates that the variant may be used to more efficiently cleave the target substrate.

The specificity or discrimination between two or more competing substrates is determined by the ratios of $k_{cat}/Km$ (Fersht, A. R., (1985) in *Enzyme Structure and Mechanism,* W. F. Freeman and Co., N.Y. p. 112). An increase in $K_{cat}/Km$ ratio for one substrate may be accompanied by a reduction in $K_{cat}/Km$ ratio for another substrate. This shift in substrate specificity indicates that the variant subtilisin with the increased $K_{cat}/Km$ ratio for the substrate has utility in cleaving the particular substrate over the precursor subtilisin in, for example, preventing undesirable hydrolysis of a particular substrate in a mixture of substrates.

In general, for a subtilisin variant to have a useful catalytic efficiency for cleavage of a particular substrate the $K_{cat}/Km$ ratio will generally be between $1\times10^3$ $M^{-1}s^{-1}$ to about $1\times10^7$ $M^{-1}s^{-1}$. More often, the $K_{cat}/Km$ ratio will be between about $1\times10^4$ $M^{-1}s^{-1}$ and $1\times10^6$ $M^{-1}s^{-1}$.

When referring to mutants or variants, the wild type amino acid residue is followed by the residue number and the new or substituted amino acid residue. For example, substitution of D for wild type N in residue position 62 is denominated N62D.

"Subtilisin variants or mutants" are designated in the same manner by using the single letter amino acid code for the wild-type residue followed by its position and the single letter amino acid code of the replacement residue. Multiple mutants are indicated by component single mutants separated by slashes. Thus the subtilisin BPN' variant N62D/G166D is a di-substituted variant in which Asp replaces Asn and Gly at residue positions 62 and 166, respectively, in wild-type subtilisin BPN'.

An amino acid residue of a precursor carbonyl hydrolase is "equivalent" to a residue of *B. amyloliquefaciens* subtilisin if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

Figure 5:
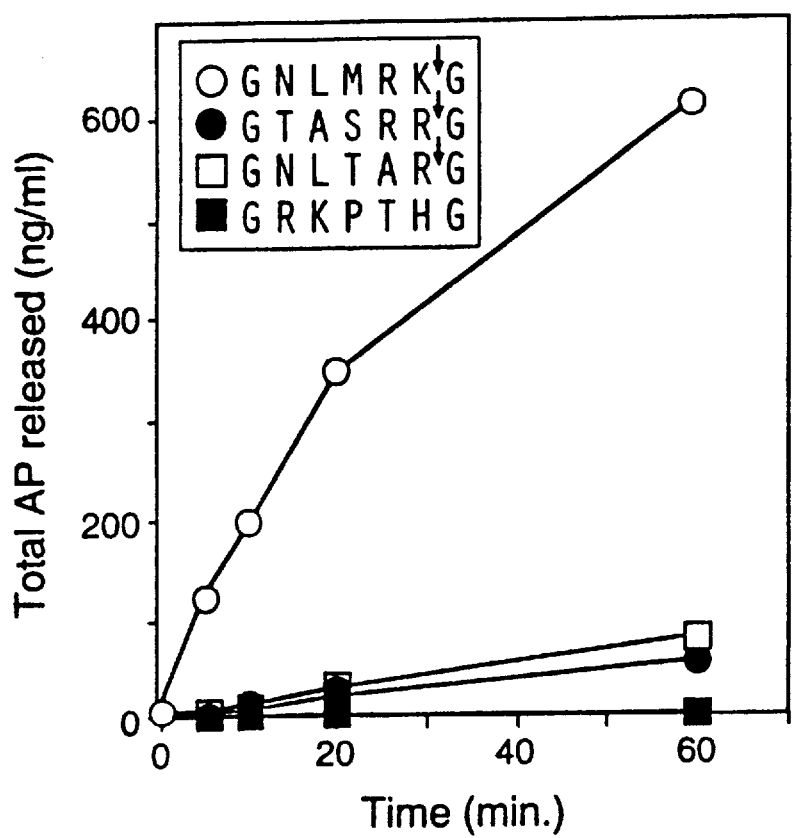
FIG. 5. Results of hGH-AP fusion protein assay. hGH-AP fusion proteins were constructed, bound to hGHbp-coupled resin, and treated with 0.5 nM N62D/G166D subtilisin in 20 mM Tris-Cl pH 8.2. Aliquots were withdrawn at various times and AP release was monitored by activity assay in comparison to a standard curve. Arrows indicate the cleavage site. The rate of cleavage of fusion proteins containing various substate linkers is shown. Substrates containing a Pro at position P1' are not cleaved.

In order to establish homology to primary structure, the amino acid sequence of a precursor carbonyl hydrolase is directly compared to the *B. amyloliquefaciens* subtilisin primary sequence and particularly to a set of residues known to be invariant in all subtilisins for which the sequences are known (see e.g. FIG. 5-C in EPO 0251446). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *B. amyloliquefaciens* subtilisin are defined. Alignment of conserved residues should conserve 100% of such residues. However, alignment of greater than 75% or as little as 50% of conserved residues is also adequate to define equivalent residues. Conservation of the catalytic triad, Asp32/His64/Ser221, is required.

Equivalent residues homologous at the level of tertiary structure for a precursor carbonyl hydrolase whose tertiary structure has been determined by x-ray crystallography, are defined as those for which the atomic coordinates of 2 or more of the main chain atoms of a particular amino acid residue of the precursor carbonyl hydrolase and *B. amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *B. amyloliquefaciens* subtilisin. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent amino acid residues of subtilisin BPN', subtilisin Carslberg, thermitase and proteinase K from tertiary structure analysis is provided in, for example, Siezen, et al., (1991) Prot. Eng. 4:719–737.

Equivalent residues which are functionally analogous to a specific residue of B. amyloliquefaciens subtilisin are defined as those amino acids of the precursor carbonyl hydrolases which may adopt a conformation such that they either alter, modify or contribute to protein structure, substrate binding or catalysis in a manner defined and attributed to a specific residue of the B. amyloliquefaciens subtilisin as described herein. Further, they are those residues of the precursor carbonyl hydrolase (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie within 0.13 nm of the corresponding side chain atoms of B. amyloliquefaciens subtilisin. The three dimensional structures would be aligned as outlined above.

Some of the residues identified for substitution are conserved residues whereas others are not. In the case of residues which are not conserved, the replacement of one or more amino acids is limited to substitutions which produce a mutant which has an amino acid sequence that does not correspond to one found in nature. In the case of conserved residues, such replacements should not result in a naturally occurring sequence. The subtilisin mutants of the present invention include the mature forms of subtilisin mutants as well as the pro- and prepro-forms of such subtilisin mutants. The prepro-forms are the preferred construction since this facilitates the expression, secretion and maturation of the subtilisin mutants.

"Prosequence" refers to a sequence of amino acids bound to the N-terminal portion of the mature form of a subtilisin which when removed results in the appearance of the "mature" form of the subtilisin. Many proteolytic enzymes are found in nature as translational proenzyme products and, in the absence of post-translational processing, are expressed in this fashion. The preferred prosequence for producing subtilisin mutants, specifically subtilisin BPN' mutants, is the putative prosequence of B. amyloliquefaciens subtilisin although other subtilisin prosequences may be used. For example, when the substrate specificity of the precursor subtilisin is altered according to the present invention, this alteration may affect the ability of the variant subtilisin to undergo autolytic cleavage of the naturally occurring prosequence. In order to affect the expression and proper folding of a mature variant subtilisin whose substrate specificity has been altered, it may be necessary to alter the prosequence to correspond to the new or variant substrate specificity.

As an example, the substrate specificity of a particular subtilisin variant N62D/Y104D/G166D is distinct from the precursor subtilisin from which it was derived. The subtilisin variant prefers substrates containing basic residues at substrate positions corresponding to P4, P2, and P1. According to this aspect of the present invention, the precursor prosequence which was efficiently autolysed by the precursor subtilisin is altered to correspond to the substrate specificity of the variant subtilisin. Therefore, for the subtilisin variant N62D/Y104/G166D the prosequence would be altered to contain basic residues at positions −4, −2, and −1.

A "signal sequence" or "presequence" refers to any sequence of amino acids bound to the N-terminal portion of a subtilisin or to the N-terminal portion of a prosubtilisin which may participate in the secretion of the mature or pro forms of the subtilisin. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention utilizes such sequences to effect the secretion of the subtilisin mutants as defined herein.

A "prepro" form of a subtilisin mutant consists of the mature form of the subtilisin having a prosequence operably linked to the amino-terminus of the subtilisin and a "pre" or "signal" sequence operably linked to the amino terminus of the prosequence.

"Expression vector" refers to a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0130756 or 0251446 or U.S. Pat. No. 5,371,008 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publication No. 0130756 and further described by Yang, M. Y., et al. (1984) J. Bacteriol. 160:15–21. Such host cells are distinguishable from those disclosed in PCT Publication No. 03949 wherein enzymatically inactive mutants of intracellular proteases in E. coli are disclosed. Other host cells for expressing subtilisin include Bacillus subtilis var. I168 (EPO Publication No. 0130756).

Host cells are transformed or transfected with vectors constructed using recombinant DNA techniques. Such transformed host cells are capable of either replicating vectors encoding the subtilisin mutants or expressing the desired subtilisin mutant. In the case of vectors which encode the pre or prepro form of the subtilisin mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor subtilisin may be obtained in accord with the general methods described in U.S. Pat. No. 4,760,025 or EPO Publication No. 0130756. As can be seen from the examples disclosed therein, the methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced.

The cloned subtilisin is then used to transform a host cell in order to express the subtilisin. The subtilisin gene is then ligated into a high copy number plasmid. This plasmid replicates in hosts in the sense that it contains the wellknown elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the subtilisin gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the subtilisin gene into host genome. This is facilitated by procaryotic and eucaryotic organisms which are particularly susceptible to homologous recombination.

Once the subtilisin gene has been cloned, a number of modifications are undertaken to enhance the use of the gene beyond synthesis of the naturally-occurring precursor subtilisin. Such modifications include the production of recombinant subtilisin as disclosed in U.S. Pat. No. 5,371,008 or EPO Publication No. 0130756 and the production of subtilisin mutants described herein.

MUTANT DESIGN AND PREPARATION

A. Subtilisin Variants Capable of Cleaving Substrates Having Dibasic Residues

For the preparation of subtilisin variants capable of cleaving substrates containing dibasic residues, the following analysis was undertaken.

A number of structures have been solved of subtilisin with a variety of inhibitors and transition state analogs bound (Wright, C. S., Alden, R. A. and Kraut, J. (1969) *Nature,* 221:235–242; McPhalen, C. A. and James, N. G. (1988) *Biochemistry,* 27:6582–6598; Bode, W., Papamokos, E., Musil, D., Seemueller, U. and Fritz, M. (1986) *EMBO J.,* 5:813–818; and Bott, R., Ultsch, M., Kossiakoff, A., Graycar, T., Katz, B. and Power, S. (1988) *J. Biol. Chem.,* 263:7895–7906). One of these structures, FIG. 1, was used to locate residues that are in close proximity to side chains at the P1 and P2 positions from the substrate. Previous work had shown that replacement residues at positions 156 and 166 in the S1 binding site with various charged residues lead to improved specificity for complementary charged substrates (Wells, J. A., Powers, D. B., Bott, R. R., Graycar, T. P. and Estell, D. A. (1987) Proc. Natl. Acad. Sci. USA, 84:1219–1223). Although longer range electrostatic effects of substrate specificity have been noted (Russell, A. J. and Fersht, A. R. (1987) *Nature,* 328:496–500) these were generally much smaller than local ones. Therefore, it seemed reasonable that local differences in charge between subtilisin BPN' and the eukaryotic enzymes may account for the differences in specificity.

A detailed sequence alignment of 35 different subtilisin-like enzymes (Siezen, R. J., de Vos, W. M., Leunissen, A. M., and Dijkstra, B. W. (1991) *Prot. Eng.,* 4:719–737) allowed us to identify differences between subtilisin BPN' and the eukaryotic processing enzymes, KEX2, furin and PC2. Within the S1 binding pocket there are a number of charged residues that appear in the pro-hormone processing enzymes and not in subtilisin BPN' (Table 1A).

TABLE 1A

| | S1 subsite | | |
|---|---|---|---|
| | 125–131[a] | 151–157 | 163–168 |
| Subtilisin BPN' | S L G G P S G | A A A G N E G | S T — V G Y P |
| | (SEQ ID NO: 3) | (SEQ ID NO: 4) | (SEQ ID NO: 5) |
| Kex2 | S W G P A D D | F A S G N G G | C N Y D G Y T |
| | (SEQ ID NO: 6) | (SEQ ID NO: 7) | (SEQ ID NO: 8) |
| Furin | S W G P E D D | W A S G N G G | C N C D G Y T |
| | (SEQ ID NO: 9) | (SEQ ID NO: 10) | (SEQ ID NO: 11) |
| PC2 | S W G P A D D | W A S G D G G | C N C D G Y A |
| | (SEQ ID NO: 6) | (SEQ ID NO: 12) | (SEQ ID NO: 13) |

[a]numbering according to subtilisin BPN' sequence

For example, the eukaryotic enzymes have two conserved Asp residues at 130 and 131 as well as an Asp at 165 that is preceded by insertion of a Tyr or Cys. However, in the region from 151–157, subtilisin BPN' contains a Glu and the eukaryotes a conserved Gly.

In the S2 binding site there were two notable differences in sequence (Table 1B).

TABLE 1B

| | S2 subsite | |
|---|---|---|
| | 30–35 | 60–64 |
| Subtilisin in BPN' | V I D S G I | D N N S H |
| | (SEQ ID NO: 14) | (SEQ ID NO: 15) |
| KEX2 | I V D D G L | S D D Y H |
| | (SEQ ID NO: 16) | (SEQ ID NO: 17) |
| Furin | I L D D G I | N D N R H |
| | (SEQ ID NO: 18) | (SEQ ID NO: 19) |
| PC2 | I M D D G I | W F N S H |
| | (SEQ ID NO: 20) | (SEQ ID NO: 21) |

Subtilisin BPB' contains a Ser at position 33 whereas the pro-hormone processing enzymes contain Asp. There is not as clear a consensus in the region of 60–64, but one notable difference is at position 62. This side chain which points directly at the P2 side chain (FIG. 1) is Asn in subtilisin BPN', furin and PC2 but Asp in KEX2. Thus, not all substitutions were clearly predictive of the specificity differences.

A variety of mutants were produced to probe and engineer the specificity of subtilisin BPN' using oligonucleotides described in Table 2.

TABLE 2

Oligonucleotides used for site-directed mutagenesis on subtilisin.

| Mutant | Oligonucleotide | Specificity Pocket | Activity Expressed |
|---|---|---|---|
| S33D | 5'-GCGGTTATCGACG*A*CGGTATCGATTCT -3' (SEQ ID NO: 22) | S2 | + |
| S33K | 5'-GCGGTTATCGACAA*A*G*GTATCGATTCT -3' (SEQ ID NO: 23) | S2 | + |
| S33E | 5'-GCGGTTATCGACG*A*A*GGTATCGATTCT -3' (SEQ ID NO: 24) | S2 | + |
| N62D | 5'-CCAAGACAACG*ACTCTCACGGAA -3' (SEQ ID NO: 25) | S2 | + |
| N62S | 5'-CCAAGACAACAG*CTCTCACGGAA -3' (SEQ ID NO: 26) | S2 | + |
| N62K | 5'-CCAAGACAACAAA*TCTCACGGAA -3' (SEQ ID NO: 27) | S2 | + |
| G166D | 5'-CACTTCCGGCAGCTCG*T*C*G*ACAGTGGA*C*T ACCCTGGC.AAATA- 3' (SEQ ID NO: 28) (Inserts Sal I site) | S1 | + |
| G166E | 5'-CACTTCCGGCAGCTCG*T*C*G*ACAGTGGA*GT ACCCTGGCAAATA-3' (SEQ ID NO: 29) (Inserts Sal I site) | S1 | + |
| G128P/P129A | 5'-TTAACATGAGCCTCGGCC*C*AG*CTA*G*C*GGT TCTGCTGCTTTA -3' (SEQ ID NO: 30) (Inserts Nhe I site) | S1 | – |
| G128P/P129A/ S130D/G131D | 5'-TTAACATGAGCCTCGGCC*C*C*G*CGG*A*TGA* TTCTGCTGCTTTAAA -3' (SEQ ID NO: 31) (Inserts Sac II site) | S1 | – |
| T164N/V165D | 5'-CGGCAGCTCAAGCA*A*C*G*A*T*GGCTAT*CCT GGCAAATACCCTTCTGTCA -3' (SEQ ID NO: 32) (Inserts BsaBI site) | S1 | – |
| T164Y/V165D | 5'-CGGCAGCTCAAGCA*A*C*G*A*T*GGCTAT*CCT GGCAAATACCCTTCTGTCA - 3' (SEQ ID NO: 33) (Inserts BstBI site) | S1 | – |
| T164N-Y(insert)-V165D | 5'-ACTTCCGGCAGCTCT*T*C*G*AA*C*T*A*C*G*A* C*GGGTACCCTGGCAAATA -3' (SEQ ID NO: 34) (Inserts BstBI site) | S1 | – |
| N62D/G166D | See individual mutations | S1/S2 | + |
| N62D/G166E | See individual mutations | S1/S2 | + |

*Asterisks indicate base changes from the pSS5 (wild-type) template.

After producing the mutant plasmids they were transformed into a protease deficient strain of *B. subtilis* (BG2036) that lacks an endogenous gene for secretion of subtilisin. These were then tested for protease activity on skim milk plates.

The first set of mutants tested were ones where segments of the S1 binding site were replaced with sequences from KEX2. None of these segment replacements produced detectable activity on skim milk plates even though variants of subtilisin whose catalytic efficiencies are reduced by as much as 1000-fold do produce detectable halos (Wells, J. A., Cunningham, B. C., Graycar, T. P. and Estell, D. A. (1986) *Philos. Trans. R. Soc. Lond. A* . 317:415–423). We went on to produce single residue substitutions that should have less impact on the stability. These mutants at positions 166 in the S1 site, and 33 and 62 in the S2 site, were chosen based on the modeling and sequence considerations described above. Fortunately all single mutants as well as combination mutants produced activity on skim milk plates and could be purified to homogeneity.

Kinetic Analysis of Variant Subtilisins

Figure 2:
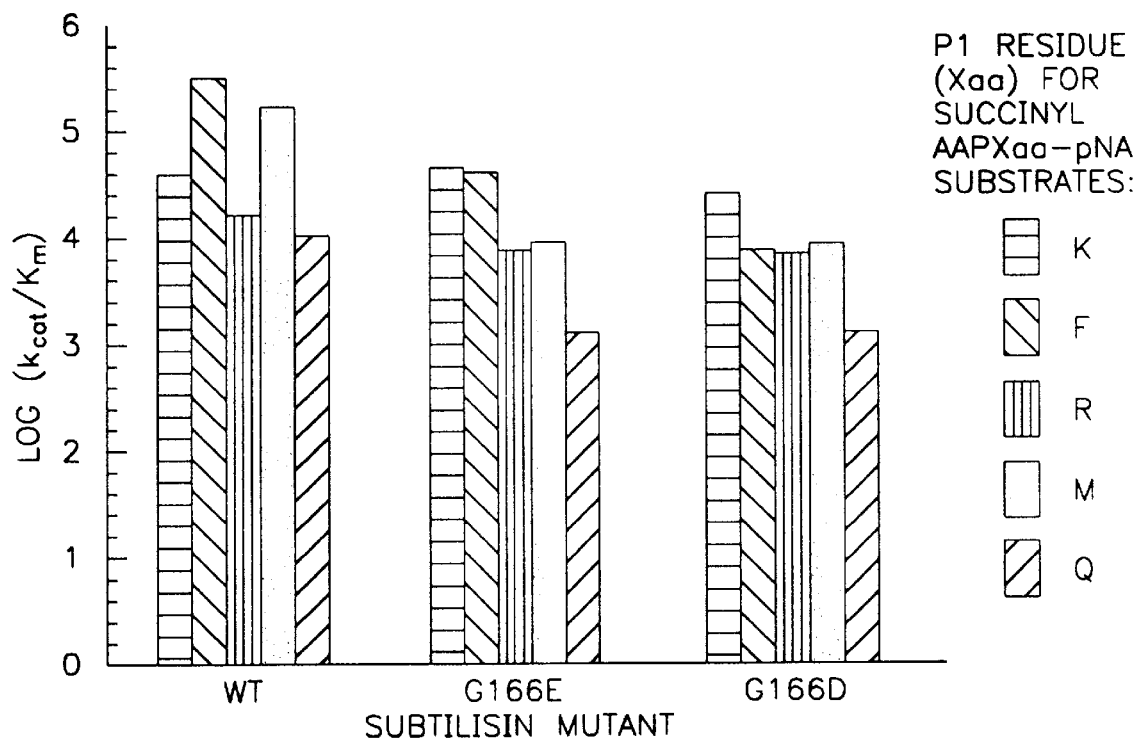
FIG. 2. Kinetic analysis of S1 binding site subtilisin mutants versus substrates having variable P1 residues. The kinetic constant $k_{cat}$/Km was determined from plots of initial rates versus substrate concentration for the tetrapeptide series succinyl-Ala-Ala-Pro-Xaa-pNa (SEQ ID NO: 69), were Xaa was Lys (SEQ ID NO: 58), Arg (SEQ ID NO: 59), Phe (SEQ ID NO: 56), Met (SEQ ID NO: 60) or Gln (SEQ ID NO: 61) (defined to the right of the plot).

To probe the effects of the G166E and G166D on specificity at the P1 position we used substrates having the form suc-AAPX-pna (SEQ ID NO: 69) where X was either Lys (SEQ ID NO. 58), Arg (SEQ ID NO. 59), Phe (SEQ ID NO. 56), Met (SEQ ID NO. 60) or Gln (SEQ ID NO. 61). The $k_{cat}/Km$ values were determined from initial rate measurements and results reported in FIG. 2. Whereas the wild-type enzyme preferred Phe>Met>Lys>Arg>Gln, the G166E preferred Lys~Phe>Arg~Met>Gln, and G166D preferred Lys>Phe~Arg~Met>Gln. Thus, both the acidic substitutions at position 166 caused a shift in preference for basic residues at the P1 site, as previously reported (Wells, J. A., Powers, D. B., Bott, R. R., Graycar, T. P.and Estell, D. A. (1987a), *Proc. Natl. Acad. Sci. USA* 84:1219–1223).

Figure 3:
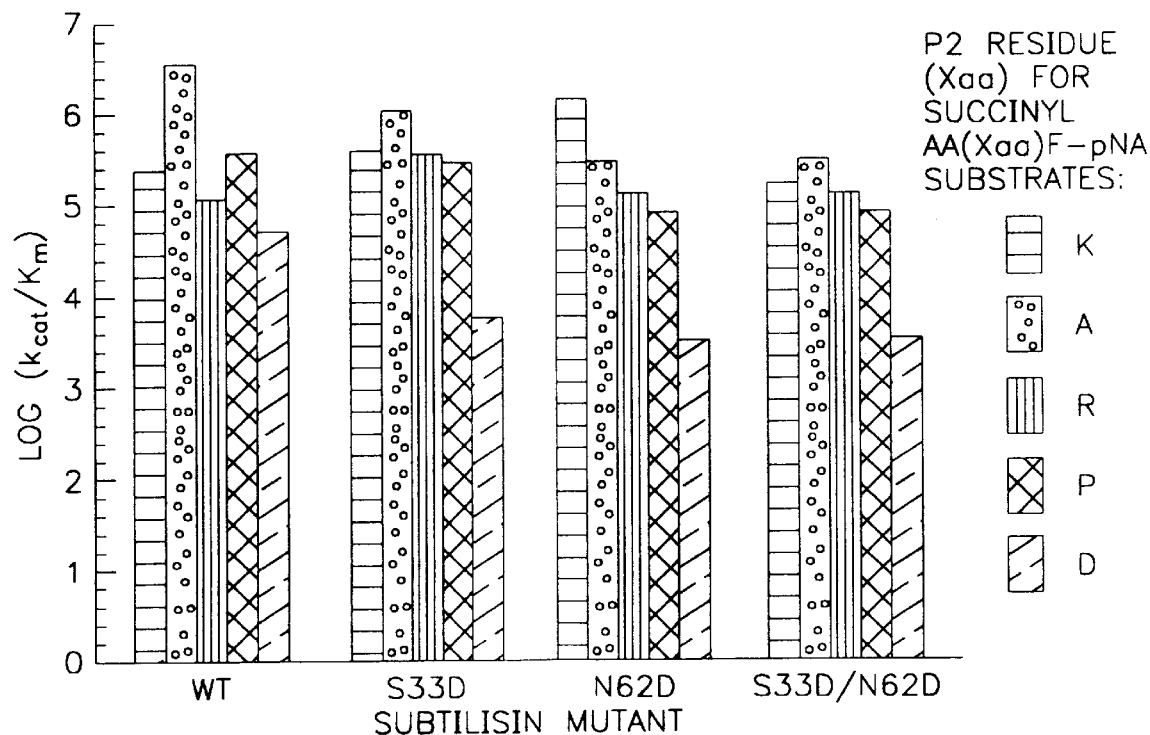
FIG. 3. Kinetic analysis of S2 binding site subtilisin mutants versus substrates having variable P2 residues. The kinetic constant $k_{cat}$/Km was determined from plots of initial rates versus substrate concentration for the tetrapeptide series succinyl-Ala-Ala-Xaa-Phe-pNa (SEQ ID NO: 70), were Xaa was Lys(SEQ ID NO: 62), Arg (SEQ ID NO: 64), Ala (SEQ ID NO: 63), Pro (SEQ ID NO: 56), or Asp (SEQ ID NO: 65) (defined on the right of the plot).

The effects of single and double substitutions in the S2 binding site were analyzed with substrates having the form, suc-Ala-Ala-Xaa-Phe-pna (SEQ ID NO. 70) and are shown in FIG. 3. At the P2 position the wild-type enzyme preferred Ala>Pro>Lys>Arg>Asp. In contrast, the S33D preferred Ala>Lys~Arg~Pro>Asp and the N62D preferred Lys>Ala>Arg>Pro>Asp. Although the effects were more dramatic for the N62D mutant, the S33D variant also showed significant improvement toward basic P2 residues and corresponding reduction in hydrolysis of the Ala and Asp P2 substrates. We then analyzed the double mutant, but found it exhibited the catalytic efficiency of the worse of the two single mutants for each of the substrates tested.

Figure 4:
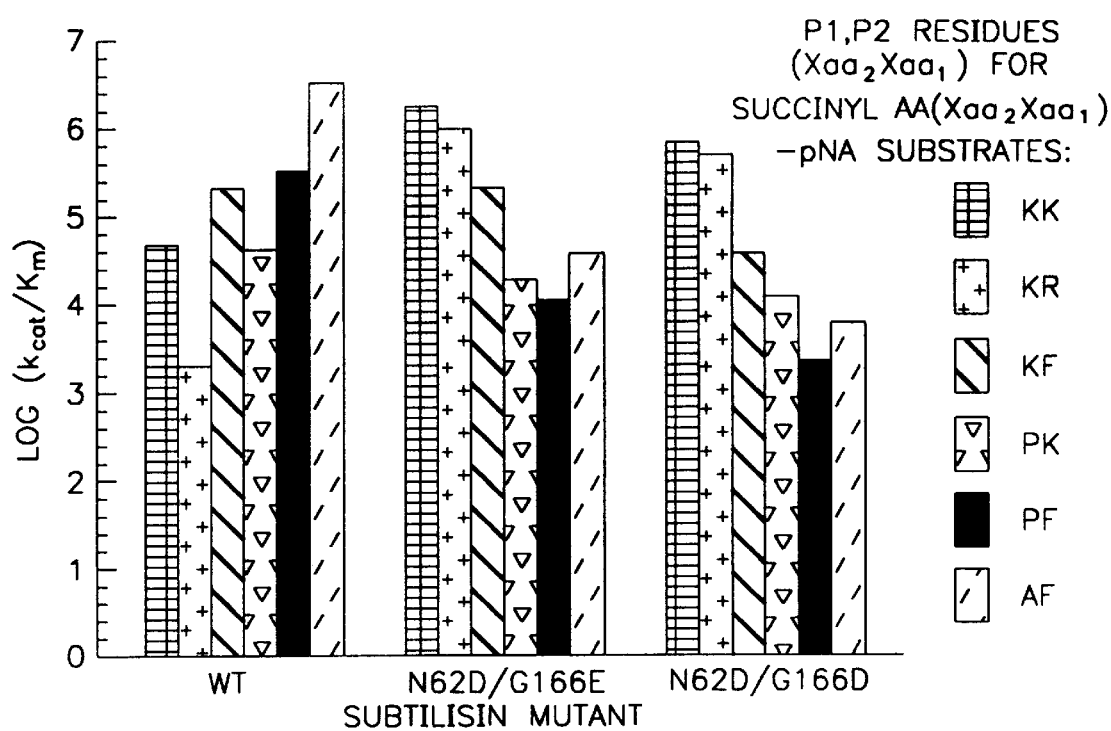
FIG. 4. Kinetic analysis of combined S1 and S2 binding site subtilisin mutants versus substrates having variable P1 and P2 residues. The kinetic constants $k_{cat}$/Km were determined from plots of initial rates versus substrate concentration for the tetrapeptide series succinyl-Ala-Ala-Xaa$_2$-Xaa$_1$-pNa (SEQ ID NO: 71), were Xaa$_2$-Xaa$_1$ was Lys-Lys (SEQ ID NO: 66), Lys-Arg (SEQ ID NO: 67), Lys-Phe(SEQ ID NO: 62), Pro-Lys (SEQ ID NO: 58), Pro-Phe (SEQ ID NO: 56), or Ala-Phe (SEQ ID NO: 63) (defined on the right of the plot).

Despite the less than additive effects seen for the two charged substitutions in the S2 site, we decided to combine the best S2 site variant (N62D) with either of the acidic substitutions in the S1 site. The two double mutants, N62D/G166E and N62D/G166D, were analyzed with substrates having the form, suc-AAXX-pna (SEQ ID NO. 71) where XX was either KK (SEQ ID NO. 66), KR (SEQ ID NO. 67), KF (SEQ ID NO. 62), PK (SEQ ID NO. 58), PF (SEQ ID NO. 56) or AF (SEQ ID NO. 63) (FIG. 4). The wild-type preference was AF>PF~KF>KK~PK>KR, whereas the double mutants had the preference KK>KR>KF>PK~AF>PF. Thus for the double mutants there was a dramatic improvement toward cleavage of dibasic substrates and away from cleaving the hydrophobic substrates.

The greater than additive effect (or synergy) of these mutants can be seen from ratios of the catalytic efficiencies for the single and multiple mutants. For example, the G166E variant cannot distinguish Lys from Phe at the P1 position. Yet the N62D/G166E variant cleaves the Lys-Lys substrate about 8 times faster than the Lys-Phe substrate. Similarly the G166D cleaves the Lys P1 substrate about 3 times faster than the Phe P1 substrate, but the N62D/G166D double mutant cleaves a Lys-Lys substrate 18 times faster than a Lys-Phe substrate. Thus, as opposed to the reduction in specificity seen for the double mutant in the S2 site, the S1–S2 double mutants enhance specificity for basic residues. It is possible that these two sites bind the dibasic substrates in a cooperative manner analogous to a chelate effect.

Therefore, according to the present invention, subtilisin mutants having a preference for dibasic residues are preferred. According to this aspect of the present invention substitution of amino acids corresponding to amino acids N62 and G166 of subtilisin BPN' produced from *Bacillus amyloliquefaciens* are prepared. In particular, amino acids 62 and 166, or their equivalents, in the precursor subtilisin are substituted with amino acid residues Asp or Glu. Preferred subtilisin variants according to this aspect of the invention include N62D/G166D, N62E/G166E, N62E/G166D, and N62D/G166E variants of subtilisin BPN' and their equivalents.

B. Subtilisin Variants Capable of Cleaving Substrates Having Tribasic Residues

Figure 7:
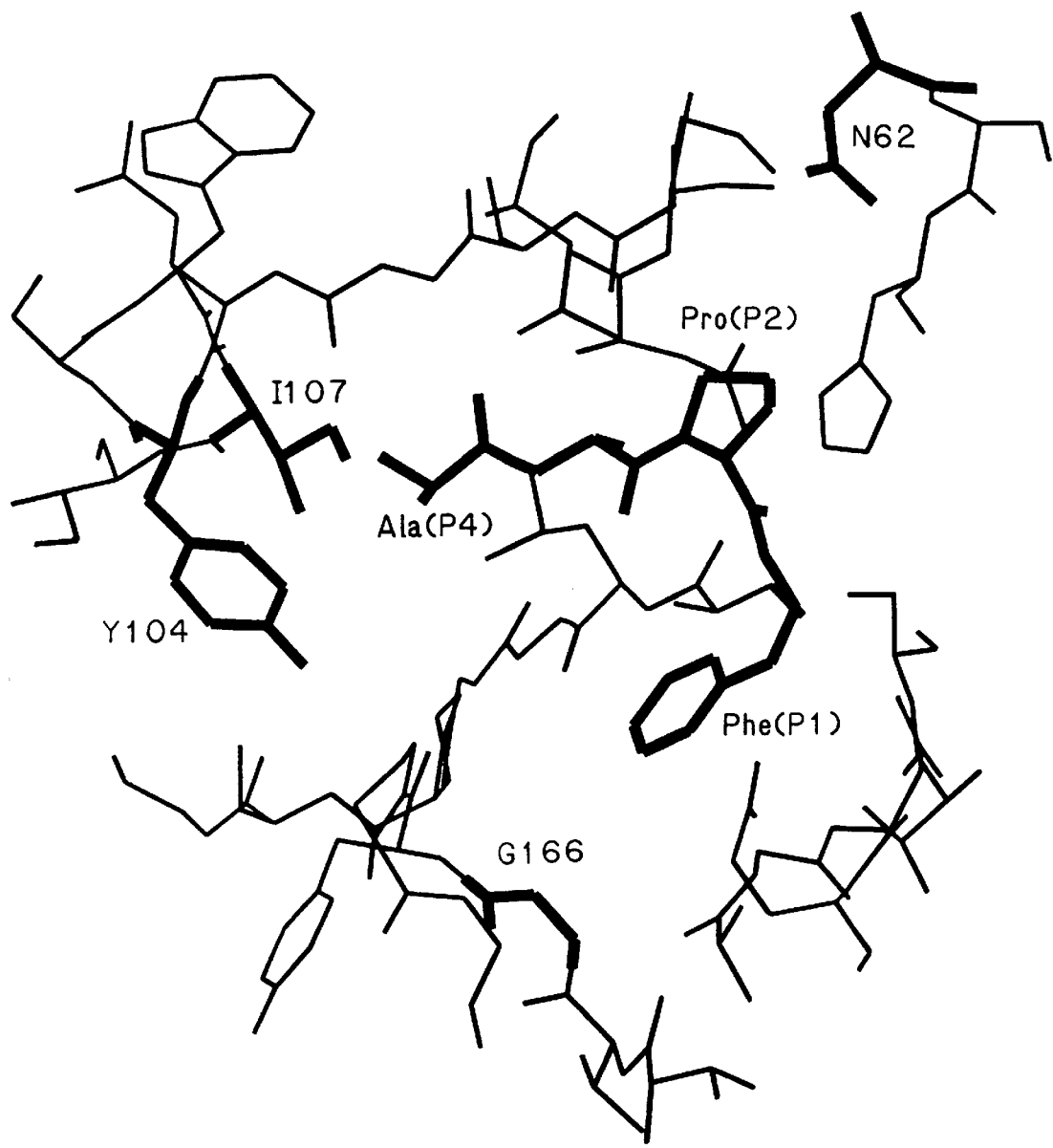
FIG. 7. Structure of a succinyl-Ala-Ala-Pro-BoroPhe (SEQ ID NO: 69) inhibitor bound to the active site of subtilisin BPN' showing the S1, S2, and S4 binding pocket residues subjected to mutagenesis.

For the preparation of subtilisin variants specific for substrates containing a third basic residue at substrate position P4 we used the crystal structure of subtilisin BPN' complexed with Ala-Ala-Pro-Phe-Boronate(SEQ ID NO: 56) (FIG. 7) in combination with sequence alignments of subtilisin BPN', KEX2, Furin, PC2, and P (Table 3) in designing basic specificity into the S1 and S2 and S4 subsites. The two subtilisin BPN' residues that most promi- nently display their side chains into the S4 pocket are Y104 and I107 (FIG. 7).

Sequence alignments of subtilisin BPN' and the mammalian prohormone-processing proteases (Siezen, R. J., de Vos, W. M., Leunissen, A. M., and Dijkstra, B. W. (1991) *Prot. Eng.* 4:719–737) (Table 3) reveal that position 104 is conserved as Asp, and 107 as Glu in the prohormone converting (Arg-P4 specific) enzymes. Therefore these two mutations were introduced either individually or in combination into the dibasic-specific N62D/G166D subtilisin BPN' background (Table 4).

TABLE 3

Sequence alignments for the S4 site of subtilisins S4 Site

100–110

| Subtilisin | GSGQYSWIING (SEQ ID NO: 77) |
| KEX2 | GDITTEDEAAS (SEQ ID NO: 78) |
| Furin | GEVTDAVEARS (SEQ ID NO: 79) |
| PC2 | PFMTDIIEASS (SEQ ID NO: 80) |
| P | GIVTDAIEASS (SEQ ID NO: 81) |

Table 4 describes oligonucleotides used for site-directed mutagenesis, protein regions affected by the mutations, and relative expression of protein for N62D/G166D subtilisin BPN' variants. Bold type indicates base changes from the pSS5 (N62D/G166D) template. For "Protein Expressed," "+" indicates a high level of expression of mature enzyme in crude culture medium, and "−" indicates no enzyme detectable.

TABLE 4

| Mutant | Oligonucleotide | Protein Region | Protein Expressed |
|---|---|---|---|
| Y104D | 5'- GGTTCCGGCCAA.GATAGCTGGATCATT -3' (SEQ ID NO: 82) | S4 pocket | − |
| I107E | 5'- CCAATACAGCTGGGAAATTAACGGAATCG -3' (SEQ ID NO: 83) | S4 pocket | − |
| Y104D/I107E | 5'- GGTTCCGGCCAAGATAGCTGGGAAATTAACG GAATCGA -3' (SEQ ID NO: 84) | S4 pocket | − |
| A(−4)R/A(−2)K/Y(−1)R | 5'- AAGAAGATCACGTAAGACATAAGCGCGCGC AGTCCGTGC -3' (SEQ ID NO: 85) | Processing site | − |
| Y104D/ A(−4)R/A(−2)K/Y(−1)R | See individual mutations | S4 pocket + Processing site | + |
| I107E/ A(−4)R/A(−2)K/Y(−1)R | See individual mutations | S4 pocket + Processing site | − |
| Y104D/I107E/ A(−4)R/A(−2)K/Y(−1)R | See individual mutations | S4 pocket + Processing site | − |

Initial attempts to express the triple mutants in Bacillus were unsuccessful, as indicated by SDS-PAGE of crude supernatants. We reasoned that the source of the expression problem could lie in the fact that correct folding and maturation of subtilisin requires autolytic cleavage of its propeptide (Power, S. D., Adams, R. M., and Wells, J. A.

(1986) *Proc. Natl. Acad. Sci. USA* 83, 3096–3100). The processing site in the wild-type enzyme has a sequence that is optimized for the natural substrate preference, AHAY↓A (↓ denotes the site of cleavage). Although the N62D/G166D subtilisin can still autolyze itself with the wild-type processing site, the additional S4 pocket mutations could reduce the cleavage to the point where expression was lowered to a minute level.

To test whether the mutants were expressed poorly due to an inability to autolytically process itself, mutations in the processing site were simultaneously incorporated to accommodate the changes in substrate specificity. Thus the sequence from positions −4 to −1 was changed from AHAY to RHKR in combination with the S4 site mutations. For N62D/Y104D/G166D, high levels of expression could then be achieved providing an indication that the additional Y104D mutation induced an especially strong preference for P4 Arg over Ala. Variants containing the I107E mutation, however, could not be expressed even with the change in the processing site.

Kinetic Analysis of Variant Subtilisins

The mature N62D/Y104D/G166D variant was purified and analyzed for its ability to hydrolyze several tetrapeptide-pNA substrates. Table 5 displays the results along with data for the N62D/G166D mutant and wild-type subtilisin.

(SEQ ID NO: 56) is hydrolyzed $6 \times 10^4$-fold less efficiently than succinyl-RAKR-pNA (SEQ ID NO: 86). Clearly, the S4 site mutation greatly improves upon the discriminatory power of the parent dibasic-specific N62D/G166D subtilisin, where the ratio of catalytic efficiency for succinyl-AAKR-pNA versus succinyl-AAPF-pNA is $1.9 \times 10^2$. The improvement in discrimination (310-fold) is also higher than would be predicted from the data for hydrolysis of succinyl-RAKR-pNA (SEQ ID NO: 86) versus succinyl-AAKR-pNA (SEQ ID NO: 67) by the triple mutant (a 60-fold effect).

Therefore in order to produce subtilisin variants capable of cleaving substrates containing basic residues at positions P4, P2, and P1, additional site specific substitutions are made in the dibasic specific subtilisin variants. According to this aspect of the invention, substitution of the amino acid corresponding to Y104 of subtilisin BPN' produced by *Bacillus Amyloliquefaciens*, i.e., amino acid 104 of subtilisin BPN' or its equivalent, produces a variant having substantially altered substrate specificity. In a preferred embodiment of the present invention amino acids corresponding to N62, Y104, and G166 of subtilisin BPN' are substituted with acidic amino acids, preferably Asp and Glu and most preferably Asp. Subtilisin BPN' variants N62D/Y104D/G166D, N62D/Y104E/G166D, N62E/Y104D/G166E, N62E/Y104E/G166E, N62E/Y104D/G166D, N62E/Y104E/G166D, N62D/Y104E/G166E, and N62D/Y104D/G166E, and there equivalents are preferred. Most preferred among

TABLE 5

Kinetic analysis of WT, N62D/G166D, and N62D/Y104D/G166D subtilisin BPN' mutants versus succinyl-tetrapeptide-pNA substrates. Kinetic constants were determined from plots of initial rates versus substrate concentration. Units are as follows: $k_{cat}$, $s^{-1}$; Km, $\mu$M; and $k_{cat}$/Km, $M^{-1}s^{-1}$. Standard errors were less than 15%.
Tetrapeptide Sequence, P4-P3-P2-P1

| Mutant | AAPF | | | AAKR | | | RAKR | | | KAKR | | |
|---|---|---|---|---|---|---|---|---|---|---|---|---|
| | $k_{cat}$ | Km | $k_{cat}$/Km | $k_{cat}$ | Km | $k_{cat}$/Km | $k_{cat}$ | Km | $k_{cat}$/Km | $k_{cat}$ | Km | $k_{cat}$/Km |
| WT | 29 | 110 | $2.6 \times 10^5$ | 2.8 | 1700 | $1.7 \times 10^{3a}$ | N.D. | N.D. | N.D. | N.D. | N.D. | N.D. |
| N62D/G166D | 3.4 | 1800 | $1.9 \times 10^3$ | 15 | 41 | $3.7 \times 10^5$ | N.D.$^b$ | N.D.$^b$ | N.D.$^b$ | N.D. | N.D. | N.D. |
| N62D/Y104D/G166D | — | — | $8.0 \times 10^{0c}$ | 0.27 | 34 | $8.1 \times 10^3$ | 11 | 23 | $4.9 \times 10^5$ | 9.8 | 29 | $3.4 \times 10^5$ |

$^a$Artificially low $k_{cat}$/Km presumably due to completing cleavage between Lys and Arg
$^b$Biphasic reaction progress curves presumably due to multiple cleavages in the substrate
$^c$Unable to saturate the enzyme, apparent $k_{cat}$/Km calculated from rates at low substrate concentrations assuming v = ($k_{cat}$/Km)(E)(S)

The tribasic substrates succinyl-RAKR-pNA (SEQ ID NO: 86) and succinyl-KAKR-pNA (SEQ ID NO: 87) were hydrolyzed with high catalytic efficiency ($k_{cat}$/Km) by the triple mutant, at a level similar to wild-type subtilisin versus one of its best substrates, succinyl-AAPF-pNA (SEQ ID NO: 56). In contrast, the dibasic substrate succinyl-AAKR-pNA (SEQ ID NO: 67) was hydrolyzed 60-fold less efficiently, mostly due to diminution of $k_{cat}$. This indicates a dramatic specificity change from the wild-type preference at P4, at which hydrophobic residues are strongly favored over charged side chains (Grøn, H. and Breddam, K. (1992) *Biochemistry* 31, 8967–8971). In fact N62D/G166D subtilisin appears to cleave at an alternate site in the succinyl-RAKR-pNA (SEQ ID NO: 86) substrate, indicating that Arg was not accepted in its wild-type S4 site.

The large magnitude of the combined specificity changes in the N62D/Y104D/G166D variant is evidenced by its strong discrimination against substrates that are preferred by the wild-type enzyme. For example, succinyl-AAPF-pNA this group of subtilisin variants are the N62D/Y104D/G166D subtilisin BPN' variants and their equivalents.

Mutagenesis and Synthetic Techniques

Various techniques are available which may be employed to produce mutant DNA, which can encode the subtilisin variants of the present invention. For instance, it is possible to derive mutant DNA based on naturally occurring DNA sequences that encode for changes in an amino acid sequence of the resultant protein relative to a precursor subtilisin. These mutant DNA can be used to obtain the variants of the present invention.

According to the invention, specific residues of *B. amyloliquefaciens* subtilisin are identified for substitution. These amino acid residue position numbers refer to those assigned to the *B. amyloliquefaciens* subtilisin sequence (see the mature sequence in FIG. 1. of U.S. Pat. No. 4,760,025). The invention, however, is not limited to the mutation of this particular subtilisin but extends to precursor subtilisins containing amino acid residues which are equivalent, as defined herein, to the particular identified residues in *B. amyloliquefaciens* subtilisin. Equivalent amino acids can be found in, for instance, subtilisn Carlesberg from *Bacillus licheniformis,* Bode et al., (1986) EMBO J., 5:813–818; thermitase from *Thermoactinomyces vulgaris,* Gros et al., (1989)J. Mol. Biol. 210:347–367; and proteinase K from *Tritirachium album,* Betzel, et al., (1988) Acto Crysollogr., B, 44:163–172) as described by Siezen et al., (1991) Prof. Eng., 4: 719–737).

By way of illustration, with expression vectors encoding the precursor subtilisin in hand (see for example U.S. Pat. No. 4,760,025) site specific mutagenesis (Kunkel et al., (1991) Methods Enzymol. 204:125–139; Carter, P., et al., (1986) Nucl. Acids. Res. 13:4331; Zoller, M. J. et al., (1982) Nucl. Acids Res. 10:6487), cassette mutagenesis (Wells, J. A., et al., (1985) Gene 34:315), restriction selection mutagenesis (Wells, J. A., et al., (1986) Philos. Trans, R. Soc. London Ser A 317, 415) or other known techniques may be performed on the DNA. The mutant DNA can then be used in place of the parent DNA by insertion into the appropriate expression vectors. Growth of host bacteria containing the expression vectors with the mutant DNA allows the production of variants which can be isolated as described herein.

Oligonucleotide-mediated mutagenesis is a preferred method for preparing the variants of the present invention. This technique is well known in the art as described by Adelman et al., (1983) *DNA,* 2:183. Briefly, the native or unaltered DNA of a precursor subtilisin, for instance subtilisin BPN', is altered by hybridizing an oligonucleotide encoding the desired mutation to a DNA template, where the template is the single-stranded form of a plasmid or bacteriophage containing the unaltered or native DNA sequence of the precursor.

After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as those described by Crea et al. (1987) Proc. Natl. Acad. Sci. USA, 75:5765. Exemplary oligonucleotide sequences for introducing amino acid changes into precursor subtilisin BPN' are provided in Tables 2 and 4.

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the variant form of the subtilisin, and the other strand (the original template) encodes the native, unaltered sequence of the precursor subtilisin. This heteroduplex molecule is then transformed into a suitable host cell. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-($\alpha$S) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell as described above.

DNA encoding variants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cleavage of a Fusion Proteins With Subtilisin Variants

A fusion protein is any polypeptide that contains within it an affinity domain (AD) that usually aids in protein purification, a protease cleavage sequence or substrate linker (SL), which is cleaved by a protease and a protein product of interest (PP). Such fusion proteins are generally expressed by recombinant DNA technology. The genes for fusion proteins are designed so that the SL is between the AD and PP. These usually take the form AD-SL-PP such that the domain closest to the N-terminus is AD and PP is closest to the C-terminus.

Examples of AD would include, glutathione-S-transferase which binds to glutathione, protein A (or derivatives or fragments thereof) which binds IgG molecules, polyhistidine sequences, particularly (His)$_6$ (SEQ ID NO: 51) that bind metal affinity columns, maltose binding protein that binds maltose, human growth hormone that binds the human growth hormone receptor or any of a variety of other proteins or protein domains that can bind to an immobilized affinity support with an association constant (Ka) of >$10^5$ $M^{-1}$.

The SL can be any sequence which is cleaved by the subtilisin variants of the present invention. In preparations where the variant N62D/Y104D/G166D or its equivalent are used the SL can be any sequence, preferably at least 4 amino acids, in which the P4, P2, and P1 residues are basic residues. Therefore a SL linker is employed of the general formula P4-P3-P2-P1 wherein P4, P2, and P1 are basic amino acid residues. Preferred SLs according to this aspect of the invention include Lys-Ala-Lys-Arg (SEQ ID NO: 87) and Arg-Ala-Lys-Arg (SEQ ID NO: 86).

Likewise, where the N62D/G166D subtilisin variant is contemplated the SL preferably contains di-basic residues. For the variants capable of cleaving substrates containing dibasic residues the SL should be at least four residues and preferably contain a large hydrophobic residue at P4 (such as Leu or Met) and dibasic residues at P2 and P1 (such as Arg and Lys). A particularly good substrate is Leu-Met-Arg-Lys- (SEQ ID NO: 52), but a variety of other sequences may work including Ala-Ser-Arg-Arg (SEQ ID NO: 50) and even Leu-Thr-Ala-Arg (SEQ ID NO 53).

It is often useful that the SL contain a flexible segment on its N-terminus to better separate it from the AD and PP. Such sequences include Gly-Pro-Gly-Gly (SEQ ID NO: 54) but can be as simple as Gly-Gly or Pro-Gly. Thus, an example of a particularly good SL would have the sequence Gly-Pro-Gly-Gly-Leu-Met-Arg-Lys (SEQ ID NO: 88) in the case of subtilisin variants capable of cleaving substrates containing dibasic amino acids, or Gly-Pro-Gly-Gly-Lys-Ala-Lys-Arg (SEQ ID NO: 89). This sequence would be inserted between the AD and PP domains.

The PP can be virtually any protein or peptide of interest but preferably should not have a Pro, Ile, Thr, Val, Asp or Glu as its first residue (P1'), or Pro or Gly at the second residue (P2') or Pro at the third residue (P3'). Such residues are poor substrates for the enzyme and may impair the ability of the subtilisins variant to cleave the SL sequence.

The conditions for cleaving the fusion protein are best done in aqueous solution, although it should be possible to immobilize the enzyme and cleave the soluble fusion protein. It may also be possible to cleave the fusion protein as it remains immobilized on a solid support (e.g. bound to the solid support through AD) with the soluble subtilisin variant. It is preferable to add the enzyme to the fusion protein so that the enzyme is less than one part in 100 (1:100) by weight. A good buffer is 10–50 mM Tris (pH 8.2) in 10 mM NaCl. A preferable temperature is about 25° C. although the enzyme is active up to 65° C. The extent of cleavage can be assayed by applying samples to SDS-PAGE. Generally suitable conditions for using the subtilisin variants of this invention do not depart substantially from those known in the art for the use of other subtilisins.

EXAMPLES

In the examples below and elsewhere, the following abbreviations are employed: subtilisin BPN', subtilisin from *Bacillus amyloliquefaciens;* Boc-RVRR-MCA (SEQ ID NO. 73), N-t-butoxy carbonyl-arginine-valine-arginine-arginine-7-amido-4-methyl coumarin; suc-Ala-Ala-Pro-Phe-pna (SEQ ID NO. 56), N-succinyl-alanine-alanine-proline-phenylalanyl-p-nitroanalide (SEQ ID NO. 56); hGH, human growth hormone; hGHbp, extracellular domain of the hGH receptor; PBS, phosphate buffered saline; AP, alkaline phosphatase;

Example 1
Construction and Purification of Subtilisin Mutants

Site-directed mutations were introduced into the subtilisin BPN' gene cloned into the phagemid pSS5 (Wells, J. A., Ferrari, E., Henner, D. J., Estell, D. A. and Chen, E. Y. (1983) *Nucl. Acids Res.* 11:7911–7929). Single-stranded uracil-containing pSS5 template was prepared and mutagenesis performed using the method of Kunkel (Kunkel, T. A., Bebenek, K and McClary, J. (1991) *Methods Enzymol.* 204:125–139). For example, the synthetic oligonucleotide N62D, (5'-CCAAGACAACG*ACTCTCACGGAA-3')
(SEQ ID NO. 25)

in which the asterisk denotes a mismatch to the wild-type sequence, was used to construct the N62D mutant. The oligonucleotide was first phosphorylated at the 5' end using T4 polynucleotide kinase according to a described procedure (Sambrook, J., Fritsch, E. F., and Maniatis, T. (1989) in "Molecular Cloning: A Laboratory Manual," Second Edition, Cold Spring Harbor, N.Y.). The phosphorylated oligonucleotide was annealed to single-stranded uracil-containing pSS5 template, the complementary DNA strand was filled in with deoxynucleotides using T7 polynucleotide kinase, and the resulting nicks ligated using T4 DNA ligase according to a previously described procedure (Sambrook, J., Fritsch, E. F., and Maniatis, T. (1989) in "Molecular Cloning: A Laboratory Manual," Second Edition, Cold Spring Harbor, N.Y.). Heteroduplex DNA was transformed into the *E. coli* host JM101(Yanish-Perron, C., Viera, J., and Messing, J. (1985) Gene 33: 103–199), and putative mutants were confirmed by preparation and dideoxy nucleotide sequencing of single stranded DNA (Sanger, F., Nicklen, S. and Coulson, A. R. (1977) *Proc. Natl. Acad. Sci. USA* 74:5463–5467) according to the SEQUENASE® protocol (USB Biochemicals). Mutant single-stranded DNA was then retransformed into JM101 cells and double stranded DNA prepared according to a previously described procedure (Sambrook, J., Fritsch, E. F., and Maniatis, T. (1989) in "Molecular Cloning: A Laboratory Manual," Second Edition, Cold Spring Harbor, N.Y.). For other mutations also requiring the use of one primer, the oligonucleotides used are listed in Table 2. For several of these oligonucleotides, additional silent mutations emplacing new restriction sites were simultaneously introduced to provide an alternative verification of mutagenesis.

To construct the double mutants N62D/G166D, and N62D/G166E, pSS5 DNA containing the N62D mutation was produced in single-stranded uracil-containing form using the Kunkel procedure (Kunkel, T. A., Bebenek, K and McClary, J. (1991) *Methods Enzymol.* 204, 125–139). This mutant DNA was used as template for the further introduction of the G166D or G166E mutations, using the appropriate oligonucleotide primers (see sequences in Table 2), following the procedures described above.

To construct the triple mutants, such as N62D/Y104D/G166D, pSS5 DNA containing the N62D/G166D mutation or other appropriate double mutation, was produced in single-stranded uracil-containing form using the Kunkel procedure (Kunkel, T. A., Bebenek, K and McClary, J. (1991) *Methods Enzymol.* 204, 125–139). This mutant DNA was used as template for the further introduction of the Y104D mutations, using the appropriate oligonucleotide primers (see sequences in Table 4), following the procedures described above.

For expression of the subtilisin BPN' mutants, double stranded mutant DNA was transformed into a protease-deficient strain (BG2036) of Bacillus Subtilis (Yang, M. Y., Ferrari, E. and Henner, D. J. (1984) *Journal of Bacteriology* 160:15–21) according to a previous method (Anagnostopolouus, C. and Spizizen, J. (1961) *Journal of Bacteriology* 81:741–746) in which transformation mixtures were plated out on LB plus skim milk plates containing 12.5 μg/mL chloramphenicol. The clear halos indicative of skim milk digestion surrounding transformed colonies were noted to roughly estimate secreted protease activity.

The transformed BG2036 strains were cultured by inoculating 5 mL of 2×YT media (Miller, J. H., (1972) in "Experiments in Molecular Genetics," Cold Spring Harbor, N.Y.) containing 12.5 μg/mL chloramphenicol and 2 mM $CaCl_2$ at 37° C. for 18–20 h, followed by 1:100 dilution in the same medium and growth in shake flasks at 37° C. for 18–22 h with vigorous aeration. The cells were harvested by centrifugation (6000 g, 15 min, 4° C.), and to the supernatant 20 mM (final) $CaCl_2$ and one volume of ethanol (−20° C.) were added. After 30 min at 4° C., the solution was centrifuged (12,000 g, 15 min, 4° C.), and one volume of ethanol (−20° C.) added to the supernatant. After 2 h at −20° C., the solution was centrifuged (12,000 g, 15 min, 4° C.) and the pellet resuspended in and dialyzed against MC (25 mM 2-(N-Morpholino)ethanesulfonic acid (MES), 5 mM $CaCl_2$ at pH 5.5) overnight at 4° C. The dialysate was passed through a 0.22 μm syringe filter and loaded onto a mono-S cation exchange column run by an FPLC system (Pharmacia Biotechnology). The column was washed with 20 volumes of MC and mutant subtilisin eluted over a linear gradient of zero to 0.15M NaCl in MC, all at a flow rate of 1 mL/min. Peak fractions were recovered and the subtilisin mutant quantitated by measuring the absorbance at 280 nm ($E_{280}$ 0.1%=1.17) (Matsubara, H.; Kasper, C B.; Brown, D. M.; and Smith, E. L. (1965)*J. Biol. Chem.*, 240:1125–1130.)

Example 2

Kinetic Characterizations

Subtilisins were assayed by measuring the initial rates of hydrolysis of p-nitroanilide tetrapeptide substrates in 0.4 mL 20 mM Tris-Cl pH 8.2, 4% (v/v) dimethyl sulfoxide at (25±0.2)° C. as described previously (Estell, D. A., Graycar, T. P., Miller, J. V., Powers, D. B., Burnier, J. P., Ng, P. G. and Wells, J. A. (1986)*Science* 233:659–663). Enzyme concentrations $(E)_0$ were determined spectrophotometrically using $E_{280\ nm}$ 0.1%=1.17 (Matsubara, H.; Kasper, C B.; Brown, D. M.; and Smith, E. L. (1965)J. Biol. Chem.,240:1125–1130.), and were typically 5–50 nM in reactions. Initial rates were determined for nine to twelve different substrate concentrations over the range of 0.001–2.0 mM. Plots of initial rates (v) versus substrate concentration (S) were fitted to the Michaelis-Menton equation, $$v = \frac{k_{cat}(E)_0((S))}{Km + (S)}$$

to determine the kinetic constants $k_{cat}$ and Km (Fersht, A. in "Enzyme Structure and Mechanism", Second edition, Freeman and Co., N.Y.) using the program Kaleidagraph (Synergy Software, Reading, Pa.).

Example 3

Substrate Phage

Substrate phage selections were performed as described by Matthews and Wells (Matthews, D. J. and Wells, J. A. (1993)*Science* 260:1113–1117), with minor modifications. Phage sorting was carried out using a library in which the linker sequence between the gene III coat protein and a tight-binding variant of hGH was $GPGGX_5GGPG$ (SEQ ID NO. 52). The library contained $2 \times 10^6$ independent transformants. Phage particles were prepared by infecting 1 mL of log phase 27C7 ($F'/tet^R/Ompt^-degP^-$) *Escherichia coli* with approximately $10^8$ library phage for 1 h at 37° C., followed by 18–24 h of growth in 25 mL 2YT medium containing $10^{10}$ M13K07 helper phage and 50 μg/mL carbenicillin at 37° C. Wells of a 96-well Nunc Maxisorb microtiter plate were coated with 2 μg/mL of hGHbp in 50 mM $NaHCO_3$ at pH 9.6 overnight at 4° C. and blocked with PBS (10 nM sodium phosphate at pH 7.4 nd 150 mM NaCl) containing 2.5% (w/v) skim milk for 1 h at room temperature. Between $10^{11}$ and $10^{12}$ phage in 0.1 mL 10 mM tris-Cl (pH 7.6), 1 mM EDTA, and 100 mM NaCl were incubated in the wells at room temperature for 2 h with gentle agitation. The plate was washed first with 20 rinses of PBS plus 0.05% Tween 20 and then twice with 20 mM tris-Cl at pH 8.2. The N62D/G166D subtilisin was added in 0.1 mL of 20 mM tris-Cl at pH 8.2 and protease sensitive phage were eluted after a variable reaction time. The concentration of protease and incubation times for elution of sensitive phage were decreased gradually over the course of sorting procedure to increase selectivity, with protease concentrations of 0.2 nM (rounds 1–3) and 0.1 nM (rounds 4–9), and reaction times of 5 min (rounds 1–6), 2.5 min (round 7), 40 s (round 8) and 20 s (round 9). Control wells in which no protease was added were also included in each round. For the resistant phage pool, the incubation time with protease remained constant at 5 min. The wells were then washed ten times with PBS plus 0.05% Tween 20 and resistant phage eluted by treatment with 0.1 mL of 0.2M glycine at pH 2.0 in PBS plus 0.05% Tween 20 for 1 min at room temperature. Protease sensitive and resistant phage pools were titered and used to infect log phase 27C7 cells for 1 h at 37° C., followed by centrifugation at 4000 rpm, removal of supernatant, and resuspension in 1 mL 2YT medium. The infected cells were then grown 18–24 h in the presence of helper phage as described above and the process repeated 9 times. Selected substrates were introduced into AP fusion proteins and assayed for relative rates of cleavage as described by Matthews and Wells (Matthews, D. J., Goodman, L. J., Gorman, C. M., and Wells, J. A. (1994)Protein Science 3:1197–1205 and Matthews, D. J. and Wells, J. A. (1993)*Science* 260:1113–1117), except that the cleavage reactions were performed in 20 mM Tris-Cl at pH 8.2.

Example 4

Substrate phage selection and cleavage of a fusion protein

Subtilisin has the capability to bind substrates from the P4 to P3' positions (McPhalen, C. A. and James, N. G. (1988)

Biochemistry 27:6582–6598 and Bode, W., Papamokos, E., Musil, D., Seemueller, U. and Fritz, M. (1986) *EMBO J.* 5:813–818). Given this extensive binding site and the apparent cooperative nature in the way the substrate can bind the enzyme we wished to explore more broadly the substrate preferences for the enzyme. To do this we utilized the substrate phage selection (Matthews, D. J., Goodman, L. J., Gorman, C. M., and Wells, J. A. (1994)Protein Science 3:1197–1205 and Matthews, D. J. and Wells, J. A. (1993) *Science* 260:1113–1117) described in Example 3. In this method a five-residue substrate linker that was flanked by di-glycine residues is inserted between an affinity domain (in this case a high affinity variant of hGH) and the carboxy-terminal domain of gene III, a minor coat protein displayed on the surface of the filamentous phage, M13. The five residue substrate linker is fully randomized to generate a library of $20^5$ different protein sequence variants. These are displayed on the phage particles which are allowed to bind to the hGHbp. The protease of interest was added and if it cleaved the phage particle at the substrate linker it released that particle. The particles released by protease treatment can be propagated and subjected to another round of selection to further enrich for good protease substrates. Sequences that are retained can also be propagated to enrich for poor protease substrates. By sequencing the isolated phage genes at the end of either selection one can identify good and poor substrates for further analysis.

We chose to focus on the subtilisin BPN' variant N62D/G166D as it was slightly better at discriminating the synthetic dibasic substrates from the others. We subjected the substrate phage library to nine rounds of selection with the subtilisin variant and isolated clones that were either increasingly sensitive or resistant to cleavage. Of twenty-one clones sequenced from the sensitive pool eighteen contained dibasic residues, eleven of which had the substrate linker sequence Asn-Leu-Met-Arg-Lys (SEQ ID NO: 35) (Table 6).

TABLE 6

Substrate phage sequences sensitive or resistant to N62D/G166D subtilisin from a GG-xxxxx-GG library after 9 rounds of selection[a].

| Protease Sensitive Pool | | |
|---|---|---|
| No Basic Sites (0) | Monobasic Sites (3) | Dibasic Sites (18) |
| | N L T A R (3) (SEQ ID NO: 34) | N L M R K (11) (SEQ ID NO: 35) T A S R R (4) (SEQ ID NO: 36) L T R R S (SEQ ID NO: 37) A L S R K (SEQ ID NO: 38) L M L R K (SEQ ID NO: 39) |

| Protease Resistant Pool | | |
|---|---|---|
| No Basic Sites (7) | Monobasic Sites (2) | Dibasic Sites (1) |
| A S T H F (SEQ ID NO: 40) I Q Q Q Y (SEQ ID NO: 43) Q G E L P (SEQ ID NO: 47) A P D P T | Q K P N F (SEQ ID NO: 41) R P G A M (SEQ ID NO: 44) | R K P T H (SEQ ID NO: 42) |

TABLE 6-continued

Substrate phage sequences sensitive or resistant to N62D/G166D subtilisin from a GG-xxxxx-GG library after 9 rounds of selection[a].

(SEQ ID NO: 46)
Q L L E H
(SEQ ID NO: 47)
V N N N H
(SEQ ID NO: 48)
A Q S N L
(SEQ ID NO: 49)

[a]Numbers in parentheses indicate the number of times a particular DNA sequence was isolated.

Three (3) of the sensitive sequences were monobasic, Asn-Leu-Thr-Ala-Arg (SEQ ID NO: 34). It is known that subtilisin has a preference for hydrophobic residues at the P4 position. If these and the other selected substrates were indeed cleaved after the last basic residue they all would have a Leu, Met or Ala at the P4 position. Almost no basic residues were isolated in the protease resistant pool and those that were had a Pro following the mono- or dibasic residue. It is known that subtilisin does not cleave substrates containing Pro at the P1' position (Carter, P., Nilsson, B., Burnier, J., Burdick, D. and Wells, J. A. (1989) *Proteins: Struct., Funct., Genet.* 6:240–248). Thus, di-basic substrates where highly selected and these had the additional feature of Leu, Met or Ala at the P4 position.

Example 5

Cleavage of Substrate Linkers

We wished to analyze how efficiently the most frequently selected sequences were cleaved in the context of a fusion protein. For this we applied an alkaline phosphatase-fusion protein assay (Matthews, D. J., Goodman, L. J., Gorman, C. M., and Wells, J. A. (1994)*Protein Science* 3:1197–1205 and Matthews, D. J. and Wells, J. A. (1993)*Science* 260:1113–1117). The hGH substrate linker domains were excised from the phage vector by PCR and fused in front of the gene for *E. coli* AP. The fusion protein was expressed and purified on an hGH receptor affinity column. The fusion protein was bound to the hGH receptor on a plate and treated with the subtilisin variant. The rate of cleavage of the fusion protein from the plate was monitored by collecting soluble fractions as a function of time and assaying for AP activity (FIG. 5). The most frequently isolated substrate sequence, Asn-Leu-Met-Arg-Lys (SEQ ID NO: 35) was cleaved about ten times faster than the next most frequently isolated clones (Thr-Ala-Ser-Arg-Arg (SEQ ID NO: 36) and Asn-Leu-Thr-Ala-Arg (SEQ ID NO: 34). The cleaved AP products were also recovered and subjected to N-terminal sequencing to determine the sites of cleavage (FIG. 5), cleavage site denoted by ↓). In all three fusion proteins, this site was immediately following the dibasic or monobasic site according to the mutant subtilisin design. We also tested the dibasic sequence isolated from the resistant pool, namely Arg-Lys-Pro-Thr-His (SEQ ID NO: 42). We observed no detectable cleavage above background for this substrate during the assay.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

All references cited herein are expressly incorporated by reference.

SEQUENCE LISTING ( 1 ) GENERAL INFORMATION:

( i i i ) NUMBER OF SEQUENCES: 90

( 2 ) INFORMATION FOR SEQ ID NO:1:

( i ) SEQUENCE CHARACTERISTICS:
    ( A ) LENGTH: 8119 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:1:

```
GAATTCNGGT  CTACTAAAAT  ATTATTCCAT  ACTATACAAT  TAATACACAG                  50

AATAATCTGT  CTATTGGTTA  TTCTGCAAAT  GAAAAAAAGG  AGAGGATAAA                 100

GA   GTG  AGA  GGC  AAA  AAA  GTA  TGG  ATC  AGT  TTG  CTG  TTT            138
     Val  Arg  Gly  Lys  Lys  Val  Trp  Ile  Ser  Leu  Leu  Phe
     -107      -105                -100

GCT  TTA  GCG  TTA  ATC  TTT  ACG  ATG  GCG  TTC  GGC  AGC  ACA            177
Ala  Leu  Ala  Leu  Ile  Phe  Thr  Met  Ala  Phe  Gly  Ser  Thr
-95                      -90                      -85

TCC  TCT  GCC  CAG  GCG  GCA  GGG  AAA  TCA  AAC  GGG  GAA  AAG            216
Ser  Ser  Ala  Gln  Ala  Ala  Gly  Lys  Ser  Asn  Gly  Glu  Lys
          -80                      -75                      -70

AAA  TAT  ATT  GTC  GGG  TTT  AAA  CAG  ACA  ATG  AGC  ACG  ATG            255
Lys  Tyr  Ile  Val  Gly  Phe  Lys  Gln  Thr  Met  Ser  Thr  Met
               -65                      -60

AGC  GCC  GCT  AAG  AAG  AAA  GAT  GTC  ATT  TCT  GAA  AAA  GGC            294
Ser  Ala  Ala  Lys  Lys  Lys  Asp  Val  Ile  Ser  Glu  Lys  Gly
-55                      -50                           -45

GGG  AAA  GTG  CAA  AAG  CAA  TTC  AAA  TAT  GTA  GAC  GCA  GCT            333
Gly  Lys  Val  Gln  Lys  Gln  Phe  Lys  Tyr  Val  Asp  Ala  Ala
          -40                      -35

TCA  GCT  ACA  TTA  AAC  GAA  AAA  GCT  GTA  AAA  GAA  TTG  AAA            372
Ser  Ala  Thr  Leu  Asn  Glu  Lys  Ala  Val  Lys  Glu  Leu  Lys
-30                      -25                      -20

AAA  GAC  CCG  AGC  GTC  GCT  TAC  GTT  GAA  GAA  GAT  CAC  GTA            411
Lys  Asp  Pro  Ser  Val  Ala  Tyr  Val  Glu  Glu  Asp  His  Val
          -15                      -10                      -5

GCA  CAT  GCG  TAC  GCG  CAG  TCC  GTG  CCT  TAC  GGC  GTA  TCA            450
Ala  His  Ala  Tyr  Ala  Gln  Ser  Val  Pro  Tyr  Gly  Val  Ser
                         1                    5

CAA  ATT  AAA  GCC  CCT  GCT  CTG  CAC  TCT  CAA  GGC  TAC  ACT            489
Gln  Ile  Lys  Ala  Pro  Ala  Leu  His  Ser  Gln  Gly  Tyr  Thr
10                       15                       20

GGA  TCA  AAT  GTT  AAA  GTA  GCG  GTT  ATC  GAC  AGC  GGT  ATC            528
Gly  Ser  Asn  Val  Lys  Val  Ala  Val  Ile  Asp  Ser  Gly  Ile
          25                       30                       35

GAT  TCT  TCT  CAT  CCT  GAT  TTA  AAG  GTA  GCA  GGC  GGA  GCC            567
Asp  Ser  Ser  His  Pro  Asp  Leu  Lys  Val  Ala  Gly  Gly  Ala
               40                       45

AGC  ATG  GTT  CCT  TCT  GAA  ACA  AAT  CCT  TTC  CAA  GAC  AAC            606
Ser  Met  Val  Pro  Ser  Glu  Thr  Asn  Pro  Phe  Gln  Asp  Asn
     50                       55                       60

GAC  TCT  CAC  GGA  ACT  CAC  GTT  GCC  GGC  ACA  GTT  GCG  GCT            645
Asp  Ser  His  Gly  Thr  His  Val  Ala  Gly  Thr  Val  Ala  Ala
               65                       70

CTT  AAT  AAC  TCA  ATC  GGT  GTA  TTA  GGC  GTT  GCG  CCA  AGC            684
Leu  Asn  Asn  Ser  Ile  Gly  Val  Leu  Gly  Val  Ala  Pro  Ser
```

```
                 75                        80                         85
GCA  TCA  CTT  TAC  GCT  GTA  AAA  GTT  CTC  GGT  GCT  GAC  GGT                 723
Ala  Ser  Leu  Tyr  Ala  Val  Lys  Val  Leu  Gly  Ala  Asp  Gly
          90                      95                      100

TCC  GGC  CAA  TAC  AGC  TGG  ATC  ATT  AAC  GGA  ATC  GAG  TGG                 762
Ser  Gly  Gln  Tyr  Ser  Trp  Ile  Ile  Asn  Gly  Ile  Glu  Trp
                    105                     110

GCG  ATC  GCA  AAC  AAT  ATG  GAC  GTT  ATT  AAC  ATG  AGC  CTC                 801
Ala  Ile  Ala  Asn  Asn  Met  Asp  Val  Ile  Asn  Met  Ser  Leu
     115                     120                     125

GGC  GGA  CCT  TCT  GGT  TCT  GCT  GCT  TTA  AAA  GCG  GCA  GTT                 840
Gly  Gly  Pro  Ser  Gly  Ser  Ala  Ala  Leu  Lys  Ala  Ala  Val
               130                     135

GAT  AAA  GCC  GTT  GCA  TCC  GGC  GTC  GTA  GTC  GTT  GCG  GCA                 879
Asp  Lys  Ala  Val  Ala  Ser  Gly  Val  Val  Val  Val  Ala  Ala
140                     145                     150

GCC  GGT  AAC  GAA  GGC  ACT  TCC  GGC  AGC  TCG  TCG  ACA  GTG                 918
Ala  Gly  Asn  Glu  Gly  Thr  Ser  Gly  Ser  Ser  Ser  Thr  Val
               155                     160                     165

GAC  TAC  CCT  GGC  AAA  TAC  CCT  TCT  GTC  ATT  GCA  GTA  GGC                 957
Asp  Tyr  Pro  Gly  Lys  Tyr  Pro  Ser  Val  Ile  Ala  Val  Gly
                    170                     175

GCT  GTT  GAC  AGC  AGC  AAC  CAA  AGA  GCA  TCT  TTC  TCA  AGC                 996
Ala  Val  Asp  Ser  Ser  Asn  Gln  Arg  Ala  Ser  Phe  Ser  Ser
     180                     185                     190

GTA  GGA  CCT  GAG  CTT  GAT  GTC  ATG  GCA  CCT  GGC  GTA  TCT                1035
Val  Gly  Pro  Glu  Leu  Asp  Val  Met  Ala  Pro  Gly  Val  Ser
               195                     200

ATC  CAA  AGC  ACG  CTT  CCT  GGA  AAC  AAA  TAC  GGG  GCG  TAC                1074
Ile  Gln  Ser  Thr  Leu  Pro  Gly  Asn  Lys  Tyr  Gly  Ala  Tyr
205                     210                     215

AAC  GGT  ACC  TCA  ATG  GCA  TCT  CCG  CAC  GTT  GCC  GGA  GCG                1113
Asn  Gly  Thr  Ser  Met  Ala  Ser  Pro  His  Val  Ala  Gly  Ala
          220                     225                     230

GCT  GCT  TTG  ATT  CTT  TCT  AAG  CAC  CCG  AAC  TGG  ACA  AAC                1152
Ala  Ala  Leu  Ile  Leu  Ser  Lys  His  Pro  Asn  Trp  Thr  Asn
                    235                     240

ACT  CAA  GTC  CGC  AGC  AGT  TTA  GAA  AAC  ACC  ACT  ACA  AAA                1191
Thr  Gln  Val  Arg  Ser  Ser  Leu  Glu  Asn  Thr  Thr  Thr  Lys
     245                     250                     255

CTT  GGT  GAT  TCT  TTC  TAC  TAT  GGA  AAA  GGG  CTG  ATC  AAC                1230
Leu  Gly  Asp  Ser  Phe  Tyr  Tyr  Gly  Lys  Gly  Leu  Ile  Asn
               260                     265

GTA  CAG  GCG  GCA  GCT  CAG  TA  AAACATAAAA  AACCGGCCTT                        1270
Val  Gln  Ala  Ala  Ala  Gln
270                     275

GGCCCCGCCG  GTTTTTTATT  ATTTTTCTTC  CTCCGCATGT  TCAATCCGCT                      1320

CCATAATCGA  CGGATGGCTC  CCTCTGAAAA  TTTTAACGAG  AAACGGCGGG                      1370

TTGACCCGGC  TCAGTCCCGT  AACGGCCAAG  TCCTGAAACG  TCTCAATCGC                      1420

CGCTTCCCGG  TTTCCGGTCA  GCTCAATGCC  GTAACGGTCG  GCGGCGTTTT                      1470

CCTGATACCG  GGAGACGGCA  TTCGTAATCG  GATCCGGAAA  TTGTAAACGT                      1520

TAATATTTTG  TTAAAATTCG  CGTTAAATTT  TTGTTAAATC  AGCTCATTTT                      1570

TTAACCAATA  GGCCGAAATC  GGCAAAATCC  CTTATAAATC  AAAAGAATAG                      1620

ACCGAGATAG  GGTTGAGTGT  TGTTCCAGTT  TGGAACAAGA  GTCCACTATT                      1670

AAAGAACGTG  GACTCCAACG  TCAAAGGGCG  AAAAACCGTC  TATCAGGGCT                      1720
```

```
ATGGCCCACT ACGTGAACCA TCACCCTAAT CAAGTTTTTT GGGGTCGAGG        1770
TGCCGTAAAG CACTAAATCG GAACCCTAAA GGGAGCCCCC GATTTAGAGC        1820
TTGACGGGGA AAGCCGGCGA ACGTGGCGAG AAAGGAAGGG AAGAAAGCGA        1870
AAGGAGCGGG CGCTAGGGCG CTGGCAAGTG TAGCGGTCAC GCTGCGCGTA        1920
ACCACCACAC CCGCCGCGCT TAATGCGCCG CTACAGGGCG CGTCCGGATC        1970
NGATCCGACG CGAGGCTGGA TGGCCTTCCC CATTATGATT CTTCTCGCTT        2020
CCGGCGGCAT CGGGATGCCC GCGTTGCAGG CCATGCTGTC CAGGCAGGTA        2070
GATGACGACC ATCAGGGACA GCTTCAAGGA TCGCTCGCGG CTCTTACCAG        2120
CCTAACTTCG ATCACTGGAC CGCTGATCGT CACGGCGATT TATGCCGCCT        2170
CGGCGAGCAC ATGGAACGGG TTGGCATGGA TTGTAGGCGC CGCCCTATAC        2220
CTTGTCTGCC TCCCCGCGTT GCGTCGCGGT GCATGGAGCC GGGCCACCTC        2270
GACCTGAATG GAAGCCGGCG GCACCTCGCT AACGGATTCA CCACTCCAAG        2320
AATTGGAGCC AATCAATTCT TGCGGAGAAC TGTGAATGCG CAAACCAACC        2370
CTTGGCAGAA CATATCCATC GCGTCCGCCA TCTCCAGCAG CCGCACGCGG        2420
CGCATCTCGG GCCGCGTTGC TGGCGTTTTT CCATAGGCTC CGCCCCCCTG        2470
ACGAGCATCA CAAAAATCGA CGCTCAAGTC AGAGGTGGCG AAACCCGACA        2520
GGACTATAAA GATACCAGGC GTTTCCCCCT GGAAGCTCCC TCGTGCGCTC        2570
TCCTGTTCCG ACCCTGCCGC TTACCGGATA CCTGTCCGCC TTTCTCCCTT        2620
CGGGAAGCGT GGCGCTTTCT CAATGCTCAC GCTGTAGGTA TCTCAGTTCG        2670
GTGTAGGTCG TTCGCTCCAA GCTGGGCTGT GTGCACGAAC CCCCCGTTCA        2720
GCCCGACCGC TGCGCCTTAT CCGGTAACTA TCGTCTTGAG TCCAACCCGG        2770
TAAGACACGA CTTATCGCCA CTGGCAGCAG CCACTGGTAA CAGGATTAGC        2820
AGAGCGAGGT ATGTAGGCGG TGCTACAGAG TTCTTGAAGT GGTGGCCTAA        2870
CTACGGCTAC ACTAGAAGGA CAGTATTTGG TATCTGCGCT CTGCTGAAGC        2920
CAGTTACCTT CGGAAAAAGA GTTGGTAGCT CTTGATCCGG CAAACAAACC        2970
ACCGCTGGTA GCGGTGGTTT TTTTGTTTGC AAGCAGCAGA TTACGCGCAG        3020
AAAAAAAGGA TCTCAAGAAG ATCCTTTGAT CTTTTCTACG GGGTCTGACG        3070
CTCAGTGGAA CGAAAACTCA CGTTAAGGGA TTTTGGTCAT GAGATTATCA        3120
AAAAGGATCT TCACCTAGAT CCTTTTAAAT TAAAAATGAA GTTTTAAATC        3170
AATCTAAAGT ATATATGAGT AAACTTGGTC TGACAGTTAC CAATGCTTAA        3220
TCAGTGAGGC ACCTATCTCA GCGATCTGTC TATTTCGTTC ATCCATAGTT        3270
GCCTGACTCC CCGTCGTGTA GATAACTACG ATACGGGAGG GCTTACCATC        3320
TGGCCCCAGT GCTGCAATGA TACCGCGAGA CCCACGCTCA CCGGCTCCAG        3370
ATTTATCAGC AATAAACCAG CCAGCCGGAA GGGCCGAGCG CAGAAGTGGT        3420
CCTGCAACTT TATCCGCCTC CATCCAGTCT ATTAATTGTT GCCGGGAAGC        3470
TAGAGTAAGT AGTTCGCCAG TTAATAGTTT GCGCAACGTT GTTGCCATTG        3520
CTGCAGGCAT CGTGGTGTCA CGCTCGTCGT TTGGTATGGC TTCATTCAGC        3570
TCCGGTTCCC AACGATCAAG GCGAGTTACA TGATCCCCCA TGTTGTGCAA        3620
AAAAGCGGTT AGCTCCTTCG GTCCTCCGAT CGTTGTCAGA AGTAAGTTGG        3670
CCGCAGTGTT ATCACTCATG GTTATGGCAG CACTGCATAA TTCTCTTACT        3720
```

```
GTCATGCCAT CCGTAAGATG CTTTTCTGTG ACTGGTGAGT ACTCAACCAA      3770
GTCATTCTGA GAATAGTGTA TGCGGCGACC GAGTTGCTCT TGCCCGGCGT      3820
CAACACGGGA TAATACCGCG CCACATAGCA GAACTTTAAA AGTGCTCATC      3870
ATTGGAAAAC GTTCTTCGGG GCGAAAACTC TCAAGGATCT TACCGCTGTT      3920
GAGATCCAGT TCGATGTAAC CCACTCGTGC ACCCAACTGA TCTTCAGCAT      3970
CTTTTACTTT CACCAGCGTT TCTGGGTGAG CAAAACAGG  AAGGCAAAAT      4020
GCCGCAAAAA AGGGAATAAG GGCGACACGG AAATGTTGAA TACTCATACT      4070
CTTCCTTTTT CAATATTATT GAAGCATTTA TCAGGGTTAT TGTCTCATGA      4120
GCGGATACAT ATTTGAATGT ATTTAGAAAA ATAAACAAAT AGGGGTTCCG      4170
CGCACATTTC CCCGAAAAGT GCCACCTGAC GTCTAAGAAA CCATTATTAT      4220
CATGACATTA ACCTATAAAA ATAGGCGTAT CACGAGGCCC TTTCGTCTTC      4270
AAGAATTAAT TCCTTAAGGA ACGTACAGAC GGCTTAAAAG CCTTTAAAAA      4320
CGTTTTTAAG GGGTTTGTAG ACAAGGTAAA GGATAAAACA GCACAATTCC      4370
AAGAAAAACA CGATTAGAA  CCTAAAAAGA ACGAATTTGA ACTAACTCAT      4420
AACCGAGAGG TAAAAAAGA  ACGAAGTCGA GATCAGGGAA TGAGTTTATA      4470
AAATAAAAAA AGCACCTGAA AAGGTGTCTT TTTTTGATGG TTTTGAACTT      4520
GTTCTTTCTT ATCTTGATAC ATATAGAAAT AACGTCATTT TTATTTTAGT      4570
TGCTGAAAGG TGCGTTGAAG TGTTGGTATG TATGTGTTTT AAAGTATTGA      4620
AAACCCTTAA AATTGGTTGC ACAGAAAAAC CCCATCTGTT AAAGTTATAA      4670
GTGACTAAAC AAATAACTAA ATAGATGGGG GTTTCTTTTA ATATTATGTG      4720
TCCTAATAGT AGCATTTATT CAGATGAAAA ATCAAGGGTT TTAGTGGACA      4770
AGACAAAAG  TGGAAAAGTG AGACCATGGA GAGAAAAGAA AATCGCTAAT      4820
GTTGATTACT TTGAACTTCT GCATATTCTT GAATTTAAAA AGGCTGAAAG      4870
AGTAAAAGAT TGTGCTGAAA TATTAGAGTA TAAACAAAAT CGTGAAACAG      4920
GCGAAAGAAA GTTGTATCGA GTGTGGTTTT GTAAATCCAG GCTTTGTCCA      4970
ATGTGCAACT GGAGGAGAGC AATGAAACAT GGCATTCAGT CACAAAAGGT      5020
TGTTGCTGAA GTTATTAAAC AAAAGCCAAC AGTTCGTTGG TTGTTTCTCA      5070
CATTAACAGT TAAAAATGTT TATGATGGCG AAGAATTAAA TAAGAGTTTG      5120
TCAGATATGG CTCAAGGATT TCGCCGAATG ATGCAATATA AAAAAATTAA      5170
TAAAAATCTT GTTGGTTTTA TGCGTGCAAC GGAAGTGACA ATAAATAATA      5220
AAGATAATTC TTATAATCAG CACATGCATG TATTGGTATG TGTGGAACCA      5270
ACTTATTTTA AGAATACAGA AAACTACGTG AATCAAAAC  AATGGATTCA      5320
ATTTTGGAAA AAGGCAATGA AATTAGACTA TGATCCAAAT GTAAAGTTC      5370
AAATGATTCG ACCGAAAAAT AAATATAAAT CGGATATACA ATCGGCAATT      5420
GACGAAACTG CAAAATATCC TGTAAAGGAT ACGGATTTTA TGACCGATGA      5470
TGAAGAAAAG AATTTGAAAC GTTTGTCTGA TTTGGAGGAA GGTTTACACC      5520
GTAAAGGTT  AATCTCCTAT GGTGGTTTGT TAAAGAAAT  ACATAAAAAA      5570
TTAAACCTTG ATGACACAGA AGAAGGCGAT TTGATTCATA CAGATGATGA      5620
CGAAAAAGCC GATGAAGATG GATTTTCTAT TATTGCAATG TGGAATTGGG      5670
AACGGAAAAA TTATTTTATT AAAGAGTAGT TCAACAAACG GGCCAGTTTG      5720
```

```
TTGAAGATTA GATGCTATAA TTGTTATTAA AAGGATTGAA GGATGCTTAG       5770

GAAGACGAGT TATTAATAGC TGAATAAGAA CGGTGCTCTC CAAATATTCT       5820

TATTTAGAAA AGCAAATCTA AAATTATCTG AAAAGGGAAT GAGAATAGTG       5870

AATGGACCAA TAATAATGAC TAGAGAAGAA AGAATGAAGA TTGTTCATGA       5920

AATTAAGGAA CGAATATTGG ATAAATATGG GGATGATGTT AAGGCTATTG       5970

GTGTTTATGG CTCTCTTGGT CGTCAGACTG ATGGGCCCTA TTCGGATATT       6020

GAGATGATGT GTGTCATGTC AACAGAGGAA GCAGAGTTCA GCCATGAATG       6070

GACAACCGGT GAGTGGAAGG TGGAAGTGAA TTTTGATAGC GAAGAGATTC       6120

TACTAGATTA TGCATCTCAG GTGGAATCAG ATTGGCCGCT TACACATGGT       6170

CAATTTTTCT CTATTTTGCC GATTTATGAT TCAGGTGGAT ACTTAGAGAA       6220

AGTGTATCAA ACTGCTAAAT CGGTAGAAGC CCAAACGTTC CACGATGCGA       6270

TTTGTGCCCT TATCGTAGAA GAGCTGTTTG AATATGCAGG CAAATGGCGT       6320

AATATTCGTG TGCAAGGACC GACAACATTT CTACCATCCT TGACTGTACA       6370

GGTAGCAATG GCAGGTGCCA TGTTGATTGG TCTGCATCAT CGCATCTGTT       6420

ATACGACGAG CGCTTCGGTC TTAACTGAAG CAGTTAAGCA ATCAGATCTT       6470

CCTTCAGGTT ATGACCATCT GTGCCAGTTC GTAATGTCTG GTCAACTTTC       6520

CGACTCTGAG AAACTTCTGG AATCGCTAGA GAATTTCTGG AATGGGATTC       6570

AGGAGTGGAC AGAACGACAC GGATATATAG TGGATGTGTC AAAACGCATA       6620

CCATTTTGAA CGATGACCTC TAATAATTGT TAATCATGTT GGTTACGTAT       6670

TTATTAACTT CTCCTAGTAT TAGTAATTAT CATGGCTGTC ATGGCGCATT       6720

AACGGAATAA AGGGTGTGCT TAAATCGGGC CATTTTGCGT AATAAGAAAA       6770

AGGATTAATT ATGAGCGAAT TGAATTAATA ATAAGGTAAT AGATTTACAT       6820

TAGAAAATGA AAGGGGATTT TATGCGTGAG AATGTTACAG TCTATCCCGG       6870

CAATAGTTAC CCTTATTATC AAGATAAGAA AGAAAAGGAT TTTTCGCTAC       6920

GCTCAAATCC TTTAAAAAAA CACAAAAGAC CACATTTTTT AATGTGGTCT       6970

TTATTCTTCA ACTAAAGCAC CCATTAGTTC AACAAACGAA AATTGGATAA       7020

AGTGGGATAT TTTTAAAATA TATATTTATG TTACAGTAAT ATTGACTTTT       7070

AAAAAAGGAT TGATTCTAAT GAAGAAAGCA GACAAGTAAG CCTCCTAAAT       7120

TCACTTTAGA TAAAAATTTA GGAGGCATAT CAAATGAACT TTAATAAAAT       7170

TGATTTAGAC AATTGGAAGA GAAAAGAGAT ATTTAATCAT TATTTGAACC       7220

AACAAACGAC TTTTAGTATA ACCACAGAAA TTGATATTAG TGTTTTATAC       7270

CGAAACATAA AACAAGAAGG ATATAAATTT TACCCTGCAT TTATTTTCTT       7320

AGTGACAAGG GTGATAAACT CAAATACAGC TTTTAGAACT GGTTACAATA       7370

GCGACGGAGA GTTAGGTTAT TGGGATAAGT TAGAGCCACT TTATACAATT       7420

TTTGATGGTG TATCTAAAAC ATTCTCTGGT ATTTGGACTC CTGTAAAGAA       7470

TGACTTCAAA GAGTTTTATG ATTTATACCT TTCTGATGTA GAGAAATATA       7520

ATGGTTCGGG GAAATTGTTT CCCAAAACAC CTATACCTGA AAATGCTTTT       7570

TCTCTTTCTA TTATTCCATG GACTTCATTT ACTGGGTTTA ACTTAAATAT       7620

CAATAATAAT AGTAATTACC TTCTACCCAT TATTACAGCA GGAAAATTCA       7670

TTAATAAAGG TAATTCAATA TATTTACCGC TATCTTTACA GGTACATCAT       7720
```

| | | | | |
|---|---|---|---|---|
| TCTGTTTGTG | ATGGTTATCA | TGCAGGATTG | TTTATGAACT | CTATTCAGGA | 7770
| ATTGTCAGAT | AGGCCTAATG | ACTGGCTTTT | ATAATATGAG | ATAATGCCGA | 7820
| CTGTACTTTT | TACAGTCGGT | TTTCTAATGT | CACTAACCTG | CCCCGTTAGT | 7870
| TGAAGAAGGT | TTTTATATTA | CAGCTCCAGA | TCCATATCCT | TCTTTTTCTG | 7920
| AACCGACTTC | TCCTTTTTCG | CTTCTTTATT | CCAATTGCTT | TATTGACGTT | 7970
| GAGCCTCGGA | ACCCNTATAG | TGTGTTATAC | TTTACTTGGA | AGTGGTTGCC | 8020
| GGAAAGAGCG | AAAATGCCTC | ACATTTGTGC | CACCTAAAAA | GGAGCGATTT | 8070
| ACATATGAGT | TATGCAGTTT | GTAGAATGCA | AAAAGTGAAA | TCAGGATCN | 8119

( 2 ) INFORMATION FOR SEQ ID NO:2:

( i ) SEQUENCE CHARACTERISTICS:
        ( A ) LENGTH: 382 amino acids
        ( B ) TYPE: Amino Acid
        ( D ) TOPOLOGY: Linear ( x i ) SEQUENCE DESCRIPTION: SEQ ID NO:2:

```
Val  Arg  Gly  Lys  Lys  Val  Trp  Ile  Ser  Leu  Leu  Phe  Ala  Leu  Ala
-107      -105                -100                          -95

Leu  Ile  Phe  Thr  Met  Ala  Phe  Gly  Ser  Thr  Ser  Ser  Ala  Gln  Ala
          -90                 -85                          -80

Ala  Gly  Lys  Ser  Asn  Gly  Glu  Lys  Lys  Tyr  Ile  Val  Gly  Phe  Lys
          -75                 -70                          -65

Gln  Thr  Met  Ser  Thr  Met  Ser  Ala  Ala  Lys  Lys  Lys  Asp  Val  Ile
          -60                 -55                          -50

Ser  Glu  Lys  Gly  Gly  Lys  Val  Gln  Lys  Gln  Phe  Lys  Tyr  Val  Asp
          -45                 -40                          -35

Ala  Ala  Ser  Ala  Thr  Leu  Asn  Glu  Lys  Ala  Val  Lys  Glu  Leu  Lys
          -30                 -25                          -20

Lys  Asp  Pro  Ser  Val  Ala  Tyr  Val  Glu  Glu  Asp  His  Val  Ala  His
          -15                 -10                           -5

Ala  Tyr  Ala  Gln  Ser  Val  Pro  Tyr  Gly  Val  Ser  Gln  Ile  Lys  Ala
           1                   5                           10

Pro  Ala  Leu  His  Ser  Gln  Gly  Tyr  Thr  Gly  Ser  Asn  Val  Lys  Val
           15                  20                          25

Ala  Val  Ile  Asp  Ser  Gly  Ile  Asp  Ser  Ser  His  Pro  Asp  Leu  Lys
           30                  35                          40

Val  Ala  Gly  Gly  Ala  Ser  Met  Val  Pro  Ser  Glu  Thr  Asn  Pro  Phe
           45                  50                          55

Gln  Asp  Asn  Asp  Ser  His  Gly  Thr  His  Val  Ala  Gly  Thr  Val  Ala
           60                  65                          70

Ala  Leu  Asn  Asn  Ser  Ile  Gly  Val  Leu  Gly  Val  Ala  Pro  Ser  Ala
           75                  80                          85

Ser  Leu  Tyr  Ala  Val  Lys  Val  Leu  Gly  Ala  Asp  Gly  Ser  Gly  Gln
           90                  95                          100

Tyr  Ser  Trp  Ile  Ile  Asn  Gly  Ile  Glu  Trp  Ala  Ile  Ala  Asn  Asn
           105                 110                         115

Met  Asp  Val  Ile  Asn  Met  Ser  Leu  Gly  Gly  Pro  Ser  Gly  Ser  Ala
           120                 125                         130

Ala  Leu  Lys  Ala  Ala  Val  Asp  Lys  Ala  Val  Ala  Ser  Gly  Val  Val
           135                 140                         145

Val  Val  Ala  Ala  Ala  Gly  Asn  Glu  Gly  Thr  Ser  Gly  Ser  Ser  Ser
           150                 155                         160
```

| Thr | Val | Asp | Tyr | Pro | Gly | Lys | Tyr | Pro | Ser | Val | Ile | Ala | Val | Gly |
|---|---|---|---|---|---|---|---|---|---|---|---|---|---|---|
| 165 | | | | | 170 | | | | | | 175 | | | |
| Ala | Val | Asp | Ser | Ser | Asn | Gln | Arg | Ala | Ser | Phe | Ser | Ser | Val | Gly |
| 180 | | | | | 185 | | | | | | 190 | | | |
| Pro | Glu | Leu | Asp | Val | Met | Ala | Pro | Gly | Val | Ser | Ile | Gln | Ser | Thr |
| 195 | | | | | 200 | | | | | | 205 | | | |
| Leu | Pro | Gly | Asn | Lys | Tyr | Gly | Ala | Tyr | Asn | Gly | Thr | Ser | Met | Ala |
| 210 | | | | | 215 | | | | | | 220 | | | |
| Ser | Pro | His | Val | Ala | Gly | Ala | Ala | Leu | Ile | Leu | Ser | Lys | His |
| 225 | | | | | 230 | | | | | | 235 | | |
| Pro | Asn | Trp | Thr | Asn | Thr | Gln | Val | Arg | Ser | Ser | Leu | Glu | Asn | Thr |
| 240 | | | | | 245 | | | | | | 250 | | | |
| Thr | Thr | Lys | Leu | Gly | Asp | Ser | Phe | Tyr | Tyr | Gly | Lys | Gly | Leu | Ile |
| 255 | | | | | 260 | | | | | | 265 | | | |
| Asn | Val | Gln | Ala | Ala | Ala | Gln |
| 270 | | | | | 275 | |

( 2 ) INFORMATION FOR SEQ ID NO:3:

( i ) SEQUENCE CHARACTERISTICS:
        ( A ) LENGTH: 7 amino acids
        ( B ) TYPE: Amino Acid
        ( D ) TOPOLOGY: Linear ( x i ) SEQUENCE DESCRIPTION: SEQ ID NO:3:

| Ser | Leu | Gly | Gly | Pro | Ser | Gly |
|---|---|---|---|---|---|---|
| 1 | | | | 5 | | 7 |

( 2 ) INFORMATION FOR SEQ ID NO:4:

( i ) SEQUENCE CHARACTERISTICS:
        ( A ) LENGTH: 7 amino acids
        ( B ) TYPE: Amino Acid
        ( D ) TOPOLOGY: Linear ( x i ) SEQUENCE DESCRIPTION: SEQ ID NO:4:

| Ala | Ala | Ala | Gly | Asn | Glu | Gly |
|---|---|---|---|---|---|---|
| 1 | | | | 5 | | 7 |

( 2 ) INFORMATION FOR SEQ ID NO:5:

( i ) SEQUENCE CHARACTERISTICS:
        ( A ) LENGTH: 6 amino acids
        ( B ) TYPE: Amino Acid
        ( D ) TOPOLOGY: Linear ( x i ) SEQUENCE DESCRIPTION: SEQ ID NO:5:

| Ser | Thr | Val | Gly | Tyr | Pro |
|---|---|---|---|---|---|
| 1 | | | | 5 | 6 |

( 2 ) INFORMATION FOR SEQ ID NO:6:

( i ) SEQUENCE CHARACTERISTICS:
        ( A ) LENGTH: 7 amino acids
        ( B ) TYPE: Amino Acid
        ( D ) TOPOLOGY: Linear ( x i ) SEQUENCE DESCRIPTION: SEQ ID NO:6:

| Ser | Trp | Gly | Pro | Ala | Asp | Asp |
|---|---|---|---|---|---|---|
| 1 | | | | 5 | | 7 |

( 2 ) INFORMATION FOR SEQ ID NO:7:

( i ) SEQUENCE CHARACTERISTICS:

(A) LENGTH: 7 amino acids
        (B) TYPE: Amino Acid
        (D) TOPOLOGY: Linear (xi) SEQUENCE DESCRIPTION: SEQ ID NO:7:

Phe Ala Ser Gly Asn Gly Gly
1               5       7

(2) INFORMATION FOR SEQ ID NO:8:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:8:

Cys Asn Tyr Asp Gly Tyr Thr
1               5       7

(2) INFORMATION FOR SEQ ID NO:9:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:9:

Ser Trp Gly Pro Glu Asp Asp
1               5       7

(2) INFORMATION FOR SEQ ID NO:10:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:10:

Trp Ala Ser Gly Asn Gly Gly
1               5       7

(2) INFORMATION FOR SEQ ID NO:11:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:11:

Cys Asn Cys Asp Gly Tyr Thr
1               5       7

(2) INFORMATION FOR SEQ ID NO:12:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:12:

Trp Ala Ser Gly Asp Gly Gly
1               5       7

(2) INFORMATION FOR SEQ ID NO:13:

(i) SEQUENCE CHARACTERISTICS:
        (A) LENGTH: 7 amino acids
        (B) TYPE: Amino Acid (D) TOPOLOGY: Linear (x i) SEQUENCE DESCRIPTION: SEQ ID NO:13:

Cys Asn Cys Asp Gly Tyr Ala
 1           5           7

(2) INFORMATION FOR SEQ ID NO:14:

(i) SEQUENCE CHARACTERISTICS:
        (A) LENGTH: 6 amino acids
        (B) TYPE: Amino Acid
        (D) TOPOLOGY: Linear (x i) SEQUENCE DESCRIPTION: SEQ ID NO:14:

Val Ile Asp Ser Gly Ile
 1           5   6

(2) INFORMATION FOR SEQ ID NO:15:

(i) SEQUENCE CHARACTERISTICS:
        (A) LENGTH: 5 amino acids
        (B) TYPE: Amino Acid
        (D) TOPOLOGY: Linear (x i) SEQUENCE DESCRIPTION: SEQ ID NO:15:

Asp Asn Asn Ser His
 1           5

(2) INFORMATION FOR SEQ ID NO:16:

(i) SEQUENCE CHARACTERISTICS:
        (A) LENGTH: 6 amino acids
        (B) TYPE: Amino Acid
        (D) TOPOLOGY: Linear (x i) SEQUENCE DESCRIPTION: SEQ ID NO:16:

Ile Val Asp Asp Gly Leu
 1           5   6

(2) INFORMATION FOR SEQ ID NO:17:

(i) SEQUENCE CHARACTERISTICS:
        (A) LENGTH: 5 amino acids
        (B) TYPE: Amino Acid
        (D) TOPOLOGY: Linear (x i) SEQUENCE DESCRIPTION: SEQ ID NO:17:

Ser Asp Asp Tyr His
 1           5

(2) INFORMATION FOR SEQ ID NO:18:

(i) SEQUENCE CHARACTERISTICS:
        (A) LENGTH: 6 amino acids
        (B) TYPE: Amino Acid
        (D) TOPOLOGY: Linear (x i) SEQUENCE DESCRIPTION: SEQ ID NO:18:

Ile Leu Asp Asp Gly Ile
 1           5   6

(2) INFORMATION FOR SEQ ID NO:19:

(i) SEQUENCE CHARACTERISTICS:
        (A) LENGTH: 5 amino acids
        (B) TYPE: Amino Acid
        (D) TOPOLOGY: Linear ( x i ) SEQUENCE DESCRIPTION: SEQ ID NO:19:

Asn Asp Asn Arg His
1                 5

( 2 ) INFORMATION FOR SEQ ID NO:20:

( i ) SEQUENCE CHARACTERISTICS:
        ( A ) LENGTH: 6 amino acids
        ( B ) TYPE: Amino Acid
        ( D ) TOPOLOGY: Linear ( x i ) SEQUENCE DESCRIPTION: SEQ ID NO:20:

Ile Met Asp Asp Gly Ile
1               5   6

( 2 ) INFORMATION FOR SEQ ID NO:21:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:21:

Trp Phe Asn Ser His
1                 5

( 2 ) INFORMATION FOR SEQ ID NO:22:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:22:

GCGGTTATCG ACGACGGTAT CGATTCT                                                 27

( 2 ) INFORMATION FOR SEQ ID NO:23:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:23:

GCGGTTATCG ACAAAGGTAT CGATTCT                                                 27

( 2 ) INFORMATION FOR SEQ ID NO:24:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:24:

GCGGTTATCG ACGAAGGTAT CGATTCT                                                 27

( 2 ) INFORMATION FOR SEQ ID NO:25:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:25:

CCAAGACAAC GACTCTCACG GAA                                                                             23

( 2 ) INFORMATION FOR SEQ ID NO:26:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:26:

CCAAGACAAC AGCTCTCACG GAA                                                                             23

( 2 ) INFORMATION FOR SEQ ID NO:27:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:27:

CCAAGACAAC AAATCTCACG GAA                                                                             23

( 2 ) INFORMATION FOR SEQ ID NO:28:

( i ) SEQUENCE CHARACTERISTICS:
        ( A ) LENGTH: 42 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:28:

CACTTCCGGC AGCTCGTCGA CAGTGGACTA CCCTGGCAAA TA                                                         42

( 2 ) INFORMATION FOR SEQ ID NO:29:

( i ) SEQUENCE CHARACTERISTICS:
        ( A ) LENGTH: 42 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:29:

CACTTCCGGC AGCTCGTCGA CAGTGGAGTA CCCTGGCAAA TA                                                         42

( 2 ) INFORMATION FOR SEQ ID NO:30:

( i ) SEQUENCE CHARACTERISTICS:
        ( A ) LENGTH: 41 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:30:

TTAACATGAG CCTCGGCCCA GCTAGCGGTT CTGCTGCTTT A                                                          41

( 2 ) INFORMATION FOR SEQ ID NO:31:

( i ) SEQUENCE CHARACTERISTICS:
        ( A ) LENGTH: 43 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:31:

TTAACATGAG CCTCGGCCCC GCGGATGATT CTGCTGCTTT AAA                                                        43

( 2 ) INFORMATION FOR SEQ ID NO:32:

( i ) SEQUENCE CHARACTERISTICS:
        ( A ) LENGTH: 47 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:32:

CGGCAGCTCA AGCAACGATG GCTATCCTGG CAAATACCCT TCTGTCA     47

( 2 ) INFORMATION FOR SEQ ID NO:33:

( i ) SEQUENCE CHARACTERISTICS:
        ( A ) LENGTH: 44 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:33:

ACTTCCGGCA GCTCTTCGAA CTACGACGGG TACCCTGGCA AATA     44

( 2 ) INFORMATION FOR SEQ ID NO:34:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:34:

Asn Leu Thr Ala Arg
1                   5

( 2 ) INFORMATION FOR SEQ ID NO:35:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:35:

Asn Leu Met Arg Lys
1                   5

( 2 ) INFORMATION FOR SEQ ID NO:36:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:36:

Thr Ala Ser Arg Arg
1                   5

( 2 ) INFORMATION FOR SEQ ID NO:37:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:37:

Leu Thr Arg Arg Ser
1                   5

( 2 ) INFORMATION FOR SEQ ID NO:38:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:38:

Ala Leu Ser Arg Lys
1                  5

( 2 ) INFORMATION FOR SEQ ID NO:39:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:39:

Leu Met Leu Arg Lys
1                  5

( 2 ) INFORMATION FOR SEQ ID NO:40:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:40:

Ala Ser Thr His Phe
1                  5

( 2 ) INFORMATION FOR SEQ ID NO:41:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:41:

Gln Lys Pro Asn Phe
1                  5

( 2 ) INFORMATION FOR SEQ ID NO:42:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:42:

Arg Lys Pro Thr His
1                  5

( 2 ) INFORMATION FOR SEQ ID NO:43:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:43:

Ile Gln Gln Gln Tyr
1                  5

( 2 ) INFORMATION FOR SEQ ID NO:44:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:44:

Arg Pro Gly Ala Met
1                  5

( 2 ) INFORMATION FOR SEQ ID NO:45:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:45:

Gln Gly Glu Leu Pro
1                  5

( 2 ) INFORMATION FOR SEQ ID NO:46:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:46:

Ala Pro Asp Pro Thr
1                  5

( 2 ) INFORMATION FOR SEQ ID NO:47:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:47:

Gln Leu Leu Glu His
1                  5

( 2 ) INFORMATION FOR SEQ ID NO:48:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:48:

Val Asn Asn Asn His
1                  5

( 2 ) INFORMATION FOR SEQ ID NO:49:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:49:

Ala Gln Ser Asn Leu
1                  5

( 2 ) INFORMATION FOR SEQ ID NO:50:

( i ) SEQUENCE CHARACTERISTICS:
    ( A ) LENGTH: 5 amino acids ( B ) TYPE: Amino Acid
( D ) TOPOLOGY: Linear ( x i ) SEQUENCE DESCRIPTION: SEQ ID NO:50:

Thr Ala Ser Arg Arg
1               5

( 2 ) INFORMATION FOR SEQ ID NO:51:

( i ) SEQUENCE CHARACTERISTICS:
( A ) LENGTH: 6 amino acids
( B ) TYPE: Amino Acid
( D ) TOPOLOGY: Linear ( x i ) SEQUENCE DESCRIPTION: SEQ ID NO:51:

His His His His His His
1               5   6

( 2 ) INFORMATION FOR SEQ ID NO:52:

( i ) SEQUENCE CHARACTERISTICS:
( A ) LENGTH: 4 amino acids
( B ) TYPE: Amino Acid
( D ) TOPOLOGY: Linear ( x i ) SEQUENCE DESCRIPTION: SEQ ID NO:52:

Leu Met Arg Lys
1           4

( 2 ) INFORMATION FOR SEQ ID NO:53:

( i ) SEQUENCE CHARACTERISTICS:
( A ) LENGTH: 4 amino acids
( B ) TYPE: Amino Acid
( D ) TOPOLOGY: Linear ( x i ) SEQUENCE DESCRIPTION: SEQ ID NO:53:

Leu Thr Ala Arg
1           4

( 2 ) INFORMATION FOR SEQ ID NO:54:

( i ) SEQUENCE CHARACTERISTICS:
( A ) LENGTH: 4 amino acids
( B ) TYPE: Amino Acid
( D ) TOPOLOGY: Linear ( x i ) SEQUENCE DESCRIPTION: SEQ ID NO:54:

Gly Pro Gly Gly
1           4

( 2 ) INFORMATION FOR SEQ ID NO:55:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:55:

Gly Leu Met Arg Lys
1               5

( 2 ) INFORMATION FOR SEQ ID NO:56:

( i ) SEQUENCE CHARACTERISTICS:
( A ) LENGTH: 4 amino acids
( B ) TYPE: Amino Acid
( D ) TOPOLOGY: Linear (x i) SEQUENCE DESCRIPTION: SEQ ID NO:56:

Ala Ala Pro Phe
 1           4

(2) INFORMATION FOR SEQ ID NO:57:

(i) SEQUENCE CHARACTERISTICS:
        (A) LENGTH: 13 amino acids
        (B) TYPE: Amino Acid
        (D) TOPOLOGY: Linear (x i) SEQUENCE DESCRIPTION: SEQ ID NO:57:

Gly Pro Gly Gly Xaa Xaa Xaa Xaa Xaa Gly Gly Pro Gly
 1           5                    10          13

(2) INFORMATION FOR SEQ ID NO:58:

(i) SEQUENCE CHARACTERISTICS:
        (A) LENGTH: 4 amino acids
        (B) TYPE: Amino Acid
        (D) TOPOLOGY: Linear (x i) SEQUENCE DESCRIPTION: SEQ ID NO:58:

Ala Ala Pro Lys
 1           4

(2) INFORMATION FOR SEQ ID NO:59:

(i) SEQUENCE CHARACTERISTICS:
        (A) LENGTH: 4 amino acids
        (B) TYPE: Amino Acid
        (D) TOPOLOGY: Linear (x i) SEQUENCE DESCRIPTION: SEQ ID NO:59:

Ala Ala Pro Arg
 1           4

(2) INFORMATION FOR SEQ ID NO:60:

(i) SEQUENCE CHARACTERISTICS:
        (A) LENGTH: 4 amino acids
        (B) TYPE: Amino Acid
        (D) TOPOLOGY: Linear (x i) SEQUENCE DESCRIPTION: SEQ ID NO:60:

Ala Ala Pro Met
 1           4

(2) INFORMATION FOR SEQ ID NO:61:

(i) SEQUENCE CHARACTERISTICS:
        (A) LENGTH: 4 amino acids
        (B) TYPE: Amino Acid
        (D) TOPOLOGY: Linear (x i) SEQUENCE DESCRIPTION: SEQ ID NO:61:

Ala Ala Pro Gln
 1           4

(2) INFORMATION FOR SEQ ID NO:62:

(i) SEQUENCE CHARACTERISTICS:
        (A) LENGTH: 4 amino acids
        (B) TYPE: Amino Acid
        (D) TOPOLOGY: Linear (x i) SEQUENCE DESCRIPTION: SEQ ID NO:62:

```
Ala  Ala  Lys  Phe
 1              4
```

(2) INFORMATION FOR SEQ ID NO:63:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:63:

```
Ala  Ala  Ala  Phe
 1              4
```

(2) INFORMATION FOR SEQ ID NO:64:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:64:

```
Ala  Ala  Arg  Phe
 1              4
```

(2) INFORMATION FOR SEQ ID NO:65:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:65:

```
Ala  Ala  Asp  Phe
 1              4
```

(2) INFORMATION FOR SEQ ID NO:66:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:66:

```
Ala  Ala  Lys  Lys
 1              4
```

(2) INFORMATION FOR SEQ ID NO:67:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:67:

```
Ala  Ala  Lys  Arg
 1              4
```

(2) INFORMATION FOR SEQ ID NO:68:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:68:

```
Ala  Ala  Lys  Phe
```

```
        1                   4
```

( 2 ) INFORMATION FOR SEQ ID NO:69:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:69:

```
Ala  Ala  Pro  Xaa
 1               4
```

( 2 ) INFORMATION FOR SEQ ID NO:70:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:70:

```
Ala  Ala  Xaa  Phe
 1               4
```

( 2 ) INFORMATION FOR SEQ ID NO:71:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:71:

```
Ala  Ala  Xaa  Xaa  Xaa
 1                    5
```

( 2 ) INFORMATION FOR SEQ ID NO:72:

( i ) SEQUENCE CHARACTERISTICS:
        ( A ) LENGTH: 275 amino acids
        ( B ) TYPE: Amino Acid
        ( D ) TOPOLOGY: Linear ( x i ) SEQUENCE DESCRIPTION: SEQ ID NO:72:

```
Ala  Gln  Ser  Val  Pro  Tyr  Gly  Val  Ser  Gln  Ile  Lys  Ala  Pro  Ala
 1                    5                         10                          15

Leu  His  Ser  Gln  Gly  Tyr  Thr  Gly  Ser  Asn  Val  Lys  Val  Ala  Val
                     20                         25                          30

Ile  Asp  Ser  Gly  Ile  Asp  Ser  Ser  His  Pro  Asp  Leu  Lys  Val  Ala
                     35                         40                          45

Gly  Gly  Ala  Ser  Met  Val  Pro  Ser  Glu  Thr  Asn  Pro  Phe  Gln  Asp
                     50                         55                          60

Asn  Asp  Ser  His  Gly  Thr  His  Val  Ala  Gly  Thr  Val  Ala  Ala  Leu
                     65                         70                          75

Asn  Asn  Ser  Ile  Gly  Val  Leu  Gly  Val  Ala  Pro  Ser  Ala  Ser  Leu
                     80                         85                          90

Tyr  Ala  Val  Lys  Val  Leu  Gly  Ala  Asp  Gly  Ser  Gly  Gln  Tyr  Ser
                     95                        100                         105

Trp  Ile  Ile  Asn  Gly  Ile  Glu  Trp  Ala  Ile  Ala  Asn  Asn  Met  Asp
                    110                        115                         120

Val  Ile  Asn  Met  Ser  Leu  Gly  Gly  Pro  Ser  Gly  Ser  Ala  Ala  Leu
                    125                        130                         135

Lys  Ala  Ala  Val  Asp  Lys  Ala  Val  Ala  Ser  Gly  Val  Val  Val  Val
                    140                        145                         150
```

| | | | | | | | | | | | | | |
|---|---|---|---|---|---|---|---|---|---|---|---|---|---|
| Ala | Ala | Ala | Gly | Asn<br>155 | Glu | Gly | Thr | Ser | Gly<br>160 | Ser | Ser | Ser | Thr | Val<br>165 |
| Asp | Tyr | Pro | Gly | Lys<br>170 | Tyr | Pro | Ser | Val | Ile<br>175 | Ala | Val | Gly | Ala | Val<br>180 |
| Asp | Ser | Ser | Asn | Gln<br>185 | Arg | Ala | Ser | Phe | Ser<br>190 | Ser | Val | Gly | Pro | Glu<br>195 |
| Leu | Asp | Val | Met | Ala<br>200 | Pro | Gly | Val | Ser | Ile<br>205 | Gln | Ser | Thr | Leu | Pro<br>210 |
| Gly | Asn | Lys | Tyr | Gly<br>215 | Ala | Tyr | Asn | Gly | Thr<br>220 | Ser | Met | Ala | Ser | Pro<br>225 |
| His | Val | Ala | Gly | Ala<br>230 | Ala | Ala | Leu | Ile | Leu<br>235 | Ser | Lys | His | Pro | Asn<br>240 |
| Trp | Thr | Asn | Thr | Gln<br>245 | Val | Arg | Ser | Ser | Leu<br>250 | Glu | Asn | Thr | Thr | Thr<br>255 |
| Lys | Leu | Gly | Asp | Ser<br>260 | Phe | Tyr | Tyr | Gly | Lys<br>265 | Gly | Leu | Ile | Asn | Val<br>270 |
| Gln | Ala | Ala | Ala | Gln<br>275 | | | | | | | | | | |

(2) INFORMATION FOR SEQ ID NO:73:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:73:

Arg Val Arg Arg
 1            4

(2) INFORMATION FOR SEQ ID NO:74:

(i) SEQUENCE CHARACTERISTICS:
        (A) LENGTH: 1146 base pairs
        (B) TYPE: Nucleic Acid
        (C) STRANDEDNESS: Single
        (D) TOPOLOGY: Linear (xi) SEQUENCE DESCRIPTION: SEQ ID NO:74:

| | | | | | | | | | | | | |
|---|---|---|---|---|---|---|---|---|---|---|---|---|
| | GTG<br>Val<br>-107 | AGA<br>Arg | GGC<br>Gly<br>-105 | AAA<br>Lys | AAA<br>Lys | GTA<br>Val | TGG<br>Trp | ATC<br>Ile<br>-100 | AGT<br>Ser | TTG<br>Leu | CTG<br>Leu | TTT<br>Phe | 36 |
| GCT<br>Ala<br>-95 | TTA<br>Leu | GCG<br>Ala | TTA<br>Leu | ATC<br>Ile | TTT<br>Phe<br>-90 | ACG<br>Thr | ATG<br>Met | GCG<br>Ala | TTC<br>Phe | GGC<br>Gly<br>-85 | AGC<br>Ser | ACA<br>Thr | 75 |
| TCC<br>Ser | TCT<br>Ser | GCC<br>Ala<br>-80 | CAG<br>Gln | GCG<br>Ala | GCA<br>Ala | GGG<br>Gly | AAA<br>Lys<br>-75 | TCA<br>Ser | AAC<br>Asn | GGG<br>Gly | GAA<br>Glu | AAG<br>Lys<br>-70 | 114 |
| AAA<br>Lys | TAT<br>Tyr | ATT<br>Ile | GTC<br>Val | GGG<br>Gly<br>-65 | TTT<br>Phe | AAA<br>Lys | CAG<br>Gln | ACA<br>Thr | ATG<br>Met<br>-60 | AGC<br>Ser | ACG<br>Thr | ATG<br>Met | 153 |
| AGC<br>Ser<br>-55 | GCC<br>Ala | GCT<br>Ala | AAG<br>Lys | AAG<br>Lys | AAA<br>Lys | GAT<br>Asp<br>-50 | GTC<br>Val | ATT<br>Ile | TCT<br>Ser | GAA<br>Glu | AAA<br>Lys<br>-45 | GGC<br>Gly | 192 |
| GGG<br>Gly | AAA<br>Lys | GTG<br>Val | CAA<br>Gln<br>-40 | AAG<br>Lys | CAA<br>Gln | TTC<br>Phe | AAA<br>Lys | TAT<br>Tyr<br>-35 | GTA<br>Val | GAC<br>Asp | GCA<br>Ala | GCT<br>Ala | 231 |
| TCA<br>Ser<br>-30 | GCT<br>Ala | ACA<br>Thr | TTA<br>Leu | AAC<br>Asn | GAA<br>Glu<br>-25 | AAA<br>Lys | GCT<br>Ala | GTA<br>Val | AAA<br>Lys | GAA<br>Glu<br>-20 | TTG<br>Leu | AAA<br>Lys | 270 |

| | | | | | | | | | | | | |
|---|---|---|---|---|---|---|---|---|---|---|---|---|
| AAA | GAC | CCG | AGC | GTC | GCT | TAC | GTT | GAA | GAA | GAT | CAC | GTA | 309 |
| Lys | Asp | Pro | Ser | Val | Ala | Tyr | Val | Glu | Glu | Asp | His | Val | |
| | -15 | | | -10 | | | | | | | | -5 | |
| AGA | CAT | AAG | CGC | GCG | CAG | TCC | GTG | CCT | TAC | GGC | GTA | TCA | 348 |
| Arg | His | Lys | Arg | Ala | Gln | Ser | Val | Pro | Tyr | Gly | Val | Ser | |
| | | | 1 | | | | | 5 | | | | | |
| CAA | ATT | AAA | GCC | CCT | GCT | CTG | CAC | TCT | CAA | GGC | TAC | ACT | 387 |
| Gln | Ile | Lys | Ala | Pro | Ala | Leu | His | Ser | Gln | Gly | Tyr | Thr | |
| 10 | | | | 15 | | | | | 20 | | | | |
| GGA | TCA | AAT | GTT | AAA | GTA | GCG | GTT | ATC | GAC | AGC | GGT | ATC | 426 |
| Gly | Ser | Asn | Val | Lys | Val | Ala | Val | Ile | Asp | Ser | Gly | Ile | |
| | | 25 | | | | 30 | | | | | | 35 | |
| GAT | TCT | TCT | CAT | CCT | GAT | TTA | AAG | GTA | GCA | GGC | GGA | GCC | 465 |
| Asp | Ser | Ser | His | Pro | Asp | Leu | Lys | Val | Ala | Gly | Gly | Ala | |
| | | | | 40 | | | | | 45 | | | | |
| AGC | ATG | GTT | CCT | TCT | GAA | ACA | AAT | CCT | TTC | CAA | GAC | AAC | 504 |
| Ser | Met | Val | Pro | Ser | Glu | Thr | Asn | Pro | Phe | Gln | Asp | Asn | |
| | 50 | | | | | 55 | | | | | 60 | | |
| GAC | TCT | CAC | GGA | ACT | CAC | GTT | GCC | GGC | ACA | GTT | GCG | GCT | 543 |
| Asp | Ser | His | Gly | Thr | His | Val | Ala | Gly | Thr | Val | Ala | Ala | |
| | | | 65 | | | | | 70 | | | | | |
| CTT | AAT | AAC | TCA | ATC | GGT | GTA | TTA | GGC | GTT | GCG | CCA | AGC | 582 |
| Leu | Asn | Asn | Ser | Ile | Gly | Val | Leu | Gly | Val | Ala | Pro | Ser | |
| 75 | | | | | 80 | | | | | 85 | | | |
| GCA | TCA | CTT | TAC | GCT | GTA | AAA | GTT | CTC | GGT | GCT | GAC | GGT | 621 |
| Ala | Ser | Leu | Tyr | Ala | Val | Lys | Val | Leu | Gly | Ala | Asp | Gly | |
| | | 90 | | | | | 95 | | | | | 100 | |
| TCC | GGC | CAA | GAT | AGC | TGG | ATC | ATT | AAC | GGA | ATC | GAG | TGG | 660 |
| Ser | Gly | Gln | Asp | Ser | Trp | Ile | Ile | Asn | Gly | Ile | Glu | Trp | |
| | | | | 105 | | | | | 110 | | | | |
| GCG | ATC | GCA | AAC | AAT | ATG | GAC | GTT | ATT | AAC | ATG | AGC | CTC | 699 |
| Ala | Ile | Ala | Asn | Asn | Met | Asp | Val | Ile | Asn | Met | Ser | Leu | |
| | 115 | | | | | 120 | | | | | 125 | | |
| GGC | GGA | CCT | TCT | GGT | TCT | GCT | GCT | TTA | AAA | GCG | GCA | GTT | 738 |
| Gly | Gly | Pro | Ser | Gly | Ser | Ala | Ala | Leu | Lys | Ala | Ala | Val | |
| | | | 130 | | | | | 135 | | | | | |
| GAT | AAA | GCC | GTT | GCA | TCC | GGC | GTC | GTA | GTC | GTT | GCG | GCA | 777 |
| Asp | Lys | Ala | Val | Ala | Ser | Gly | Val | Val | Val | Val | Ala | Ala | |
| 140 | | | | | 145 | | | | | 150 | | | |
| GCC | GGT | AAC | GAA | GGC | ACT | TCC | GGC | AGC | TCG | TCG | ACA | GTG | 816 |
| Ala | Gly | Asn | Glu | Gly | Thr | Ser | Gly | Ser | Ser | Ser | Thr | Val | |
| | | 155 | | | | | 160 | | | | | 165 | |
| GAC | TAC | CCT | GGC | AAA | TAC | CCT | TCT | GTC | ATT | GCA | GTA | GGC | 855 |
| Asp | Tyr | Pro | Gly | Lys | Tyr | Pro | Ser | Val | Ile | Ala | Val | Gly | |
| | | | | 170 | | | | 175 | | | | | |
| GCT | GTT | GAC | AGC | AGC | AAC | CAA | AGA | GCA | TCT | TTC | TCA | AGC | 894 |
| Ala | Val | Asp | Ser | Ser | Asn | Gln | Arg | Ala | Ser | Phe | Ser | Ser | |
| | 180 | | | | | 185 | | | | 190 | | | |
| GTA | GGA | CCT | GAG | CTT | GAT | GTC | ATG | GCA | CCT | GGC | GTA | TCT | 933 |
| Val | Gly | Pro | Glu | Leu | Asp | Val | Met | Ala | Pro | Gly | Val | Ser | |
| | | | 195 | | | | | 200 | | | | | |
| ATC | CAA | AGC | ACG | CTT | CCT | GGA | AAC | AAA | TAC | GGG | GCG | TAC | 972 |
| Ile | Gln | Ser | Thr | Leu | Pro | Gly | Asn | Lys | Tyr | Gly | Ala | Tyr | |
| 205 | | | | | 210 | | | | | 215 | | | |
| AAC | GGT | ACC | TCA | ATG | GCA | TCT | CCG | CAC | GTT | GCC | GGA | GCG | 1011 |
| Asn | Gly | Thr | Ser | Met | Ala | Ser | Pro | His | Val | Ala | Gly | Ala | |
| | | 220 | | | | | 225 | | | | | 230 | |
| GCT | GCT | TTG | ATT | CTT | TCT | AAG | CAC | CCG | AAC | TGG | ACA | AAC | 1050 |
| Ala | Ala | Leu | Ile | Leu | Ser | Lys | His | Pro | Asn | Trp | Thr | Asn | |
| | | | | 235 | | | | | 240 | | | | |

| | | | | | | | | | | | | |
|---|---|---|---|---|---|---|---|---|---|---|---|---|
| ACT | CAA | GTC | CGC | AGC | AGT | TTA | GAA | AAC | ACC | ACT | ACA | AAA | 1089 |
| Thr | Gln | Val | Arg | Ser | Ser | Leu | Glu | Asn | Thr | Thr | Thr | Lys | |
| 245 | | | | | 250 | | | | | | 255 | | |
| | | | | | | | | | | | | |
| CTT | GGT | GAT | TCT | TTC | TAC | TAT | GGA | AAA | GGG | CTG | ATC | AAC | 1128 |
| Leu | Gly | Asp | Ser | Phe | Tyr | Tyr | Gly | Lys | Gly | Leu | Ile | Asn | |
| | | | 260 | | | | | 265 | | | | | |
| | | | | | | | | | | | | |
| GTA | CAG | GCG | GCA | GCT | CAG | | | | | | | | 1146 |
| Val | Gln | Ala | Ala | Ala | Gln | | | | | | | | |
| 270 | | | | | 275 | | | | | | | | |

( 2 ) INFORMATION FOR SEQ ID NO:75:

( i ) SEQUENCE CHARACTERISTICS:
        ( A ) LENGTH: 382 amino acids
        ( B ) TYPE: Amino Acid
        ( D ) TOPOLOGY: Linear ( x i ) SEQUENCE DESCRIPTION: SEQ ID NO:75:

| | | | | | | | | | | | | |
|---|---|---|---|---|---|---|---|---|---|---|---|---|
| Val | Arg | Gly | Lys | Lys | Val | Trp | Ile | Ser | Leu | Leu | Phe | Ala | Leu | Ala |
| -107 | | -105 | | | | -100 | | | | | -95 | | | |
| Leu | Ile | Phe | Thr | Met | Ala | Phe | Gly | Ser | Thr | Ser | Ser | Ala | Gln | Ala |
| | | -90 | | | | -85 | | | | | -80 | | | |
| Ala | Gly | Lys | Ser | Asn | Gly | Glu | Lys | Lys | Tyr | Ile | Val | Gly | Phe | Lys |
| | | -75 | | | | -70 | | | | | -65 | | | |
| Gln | Thr | Met | Ser | Thr | Met | Ser | Ala | Ala | Lys | Lys | Lys | Asp | Val | Ile |
| | | -60 | | | | -55 | | | | | -50 | | | |
| Ser | Glu | Lys | Gly | Gly | Lys | Val | Gln | Lys | Gln | Phe | Lys | Tyr | Val | Asp |
| | | -45 | | | | -40 | | | | | -35 | | | |
| Ala | Ala | Ser | Ala | Thr | Leu | Asn | Glu | Lys | Ala | Val | Lys | Glu | Leu | Lys |
| | | -30 | | | | -25 | | | | | -20 | | | |
| Lys | Asp | Pro | Ser | Val | Ala | Tyr | Val | Glu | Glu | Asp | His | Val | Arg | His |
| | | -15 | | | | -10 | | | | | -5 | | | |
| Lys | Arg | Ala | Gln | Ser | Val | Pro | Tyr | Gly | Val | Ser | Gln | Ile | Lys | Ala |
| | | | 1 | | | 5 | | | | | 10 | | | |
| Pro | Ala | Leu | His | Ser | Gln | Gly | Tyr | Thr | Gly | Ser | Asn | Val | Lys | Val |
| | | 15 | | | | 20 | | | | | 25 | | | |
| Ala | Val | Ile | Asp | Ser | Gly | Ile | Asp | Ser | Ser | His | Pro | Asp | Leu | Lys |
| | | 30 | | | | 35 | | | | | 40 | | | |
| Val | Ala | Gly | Gly | Ala | Ser | Met | Val | Pro | Ser | Glu | Thr | Asn | Pro | Phe |
| | | 45 | | | | 50 | | | | | 55 | | | |
| Gln | Asp | Asn | Asp | Ser | His | Gly | Thr | His | Val | Ala | Gly | Thr | Val | Ala |
| | | 60 | | | | 65 | | | | | 70 | | | |
| Ala | Leu | Asn | Asn | Ser | Ile | Gly | Val | Leu | Gly | Val | Ala | Pro | Ser | Ala |
| | | 75 | | | | 80 | | | | | 85 | | | |
| Ser | Leu | Tyr | Ala | Val | Lys | Val | Leu | Gly | Ala | Asp | Gly | Ser | Gly | Gln |
| | | 90 | | | | 95 | | | | | 100 | | | |
| Asp | Ser | Trp | Ile | Ile | Asn | Gly | Ile | Glu | Trp | Ala | Ile | Ala | Asn | Asn |
| | | 105 | | | | 110 | | | | | 115 | | | |
| Met | Asp | Val | Ile | Asn | Met | Ser | Leu | Gly | Gly | Pro | Ser | Gly | Ser | Ala |
| | | 120 | | | | 125 | | | | | 130 | | | |
| Ala | Leu | Lys | Ala | Ala | Val | Asp | Lys | Ala | Val | Ala | Ser | Gly | Val | Val |
| | | 135 | | | | 140 | | | | | 145 | | | |
| Val | Val | Ala | Ala | Ala | Gly | Asn | Glu | Gly | Thr | Ser | Gly | Ser | Ser | Ser |
| | | 150 | | | | 155 | | | | | 160 | | | |
| Thr | Val | Asp | Tyr | Pro | Gly | Lys | Tyr | Pro | Ser | Val | Ile | Ala | Val | Gly |
| | | 165 | | | | 170 | | | | | 175 | | | |
| Ala | Val | Asp | Ser | Ser | Asn | Gln | Arg | Ala | Ser | Phe | Ser | Ser | Val | Gly |

```
                180                     185                       190

Pro  Glu  Leu  Asp  Val  Met  Ala  Pro  Gly  Val  Ser  Ile  Gln  Ser  Thr
         195                      200                      205

Leu  Pro  Gly  Asn  Lys  Tyr  Gly  Ala  Tyr  Asn  Gly  Thr  Ser  Met  Ala
         210                      215                      220

Ser  Pro  His  Val  Ala  Gly  Ala  Ala  Leu  Ile  Leu  Ser  Lys  His
         225                      230                      235

Pro  Asn  Trp  Thr  Asn  Thr  Gln  Val  Arg  Ser  Ser  Leu  Glu  Asn  Thr
         240                      245                      250

Thr  Thr  Lys  Leu  Gly  Asp  Ser  Phe  Tyr  Tyr  Gly  Lys  Gly  Leu  Ile
         255                      260                      265

Asn  Val  Gln  Ala  Ala  Ala  Gln
         270                      275
```

( 2 ) INFORMATION FOR SEQ ID NO:76:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:76:

```
    Asn  Arg  Met  Arg  Lys
     1                    5
```

( 2 ) INFORMATION FOR SEQ ID NO:77:

( i ) SEQUENCE CHARACTERISTICS:
        ( A ) LENGTH: 11 amino acids
        ( B ) TYPE: Amino Acid
        ( D ) TOPOLOGY: Linear ( x i ) SEQUENCE DESCRIPTION: SEQ ID NO:77:

```
    Gly  Ser  Gly  Gln  Tyr  Ser  Trp  Ile  Ile  Asn  Gly
     1                    5                    10   11
```

( 2 ) INFORMATION FOR SEQ ID NO:78:

( i ) SEQUENCE CHARACTERISTICS:
        ( A ) LENGTH: 11 amino acids
        ( B ) TYPE: Amino Acid
        ( D ) TOPOLOGY: Linear ( x i ) SEQUENCE DESCRIPTION: SEQ ID NO:78:

```
    Gly  Asp  Ile  Thr  Thr  Glu  Asp  Glu  Ala  Ala  Ser
     1                    5                    10   11
```

( 2 ) INFORMATION FOR SEQ ID NO:79:

( i ) SEQUENCE CHARACTERISTICS:
        ( A ) LENGTH: 11 amino acids
        ( B ) TYPE: Amino Acid
        ( D ) TOPOLOGY: Linear ( x i ) SEQUENCE DESCRIPTION: SEQ ID NO:79:

```
    Gly  Glu  Val  Thr  Asp  Ala  Val  Glu  Ala  Arg  Ser
     1                    5                    10   11
```

( 2 ) INFORMATION FOR SEQ ID NO:80:

( i ) SEQUENCE CHARACTERISTICS:
        ( A ) LENGTH: 11 amino acids
        ( B ) TYPE: Amino Acid
        ( D ) TOPOLOGY: Linear ( x i ) SEQUENCE DESCRIPTION: SEQ ID NO:80:

Pro Phe Met Thr Asp Ile Ile Glu Ala Ser Ser
 1               5                   10  11

( 2 ) INFORMATION FOR SEQ ID NO:81:

( i ) SEQUENCE CHARACTERISTICS:
        ( A ) LENGTH: 11 amino acids
        ( B ) TYPE: Amino Acid
        ( D ) TOPOLOGY: Linear ( x i ) SEQUENCE DESCRIPTION: SEQ ID NO:81:

Gly Ile Val Thr Asp Ala Ile Glu Ala Ser Ser
 1               5                   10  11

( 2 ) INFORMATION FOR SEQ ID NO:82:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:82:

GGTTCCGGCC AAGATAGCTG GATCATT        27

( 2 ) INFORMATION FOR SEQ ID NO:83:

( i ) SEQUENCE CHARACTERISTICS:
        ( A ) LENGTH: 29 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:83:

CCAATACAGC TGGGAAATTA ACGGAATCG        29

( 2 ) INFORMATION FOR SEQ ID NO:84:

( i ) SEQUENCE CHARACTERISTICS:
        ( A ) LENGTH: 31 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:84:

GGTTCCGGCC AAGATAGCTG GGAAATTAAC G        31

( 2 ) INFORMATION FOR SEQ ID NO:85:

( i ) SEQUENCE CHARACTERISTICS:
        ( A ) LENGTH: 30 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:85:

AAGAAGATCA CGTAAGACAT AAGCGCGCGC        30

( 2 ) INFORMATION FOR SEQ ID NO:86:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:86:

Arg Ala Lys Arg
1                4

( 2 ) INFORMATION FOR SEQ ID NO:87:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:87:

Lys Ala Lys Arg
1                4

( 2 ) INFORMATION FOR SEQ ID NO:88:

( i ) SEQUENCE CHARACTERISTICS:
        ( A ) LENGTH: 8 amino acids
        ( B ) TYPE: Amino Acid
        ( D ) TOPOLOGY: Linear ( x i ) SEQUENCE DESCRIPTION: SEQ ID NO:88:

Gly Pro Gly Gly Leu Met Arg Lys
1                5                   8

( 2 ) INFORMATION FOR SEQ ID NO:89:

( i ) SEQUENCE CHARACTERISTICS:
        ( A ) LENGTH: 8 amino acids
        ( B ) TYPE: Amino Acid
        ( D ) TOPOLOGY: Linear ( x i ) SEQUENCE DESCRIPTION: SEQ ID NO:89:

Gly Pro Gly Gly Lys Ala Lys Arg
1                5                   8

( 2 ) INFORMATION FOR SEQ ID NO:90:

( i ) SEQUENCE CHARACTERISTICS:
        ( A ) LENGTH: 275 amino acids
        ( B ) TYPE: Amino Acid
        ( D ) TOPOLOGY: Linear ( x i ) SEQUENCE DESCRIPTION: SEQ ID NO:90:

Ala Gln Ser Val Pro Tyr Gly Val Ser Gln Ile Lys Ala Pro Ala
1                5                              10                            15

Leu His Ser Gln Gly Tyr Thr Gly Ser Asn Val Lys Val Ala Val
                    20                             25                            30

Ile Asp Ser Gly Ile Asp Ser Ser His Pro Asp Leu Lys Val Ala
                    35                             40                            45

Gly Gly Ala Ser Met Val Pro Ser Glu Thr Asn Pro Phe Gln Asp
                    50                             55                            60

Asn Asn Ser His Gly Thr His Val Ala Gly Thr Val Ala Ala Leu
                    65                             70                            75

Asn Asn Ser Ile Gly Val Leu Gly Val Ala Pro Ser Ala Ser Leu
                    80                             85                            90

Tyr Ala Val Lys Val Leu Gly Ala Asp Gly Ser Gly Gln Tyr Ser
                    95                             100                           105

Trp Ile Ile Asn Gly Ile Glu Trp Ala Ile Ala Asn Asn Met Asp
                    110                            115                           120

Val Ile Asn Met Ser Leu Gly Gly Pro Ser Gly Ser Ala Ala Leu
                    125                            130                           135

Lys Ala Ala Val Asp Lys Ala Val Ala Ser Gly Val Val Val Val

-continued

|   |   |   |   | 140 |   |   |   |   | 145 |   |   |   |   | 150 |
|---|---|---|---|---|---|---|---|---|---|---|---|---|---|---|
| Ala | Ala | Ala | Gly | Asn<br>155 | Glu | Gly | Thr | Ser | Gly<br>160 | Ser | Ser | Ser | Thr | Val<br>165 |
| Gly | Tyr | Pro | Gly | Lys<br>170 | Tyr | Pro | Ser | Val | Ile<br>175 | Ala | Val | Gly | Ala | Val<br>180 |
| Asp | Ser | Ser | Asn | Gln<br>185 | Arg | Ala | Ser | Phe | Ser<br>190 | Ser | Val | Gly | Pro | Glu<br>195 |
| Leu | Asp | Val | Met | Ala<br>200 | Pro | Gly | Val | Ser | Ile<br>205 | Gln | Ser | Thr | Leu | Pro<br>210 |
| Gly | Asn | Lys | Tyr | Gly<br>215 | Ala | Tyr | Asn | Gly | Thr<br>220 | Ser | Met | Ala | Ser | Pro<br>225 |
| His | Val | Ala | Gly | Ala<br>230 | Ala | Ala | Leu | Ile | Leu<br>235 | Ser | Lys | His | Pro | Asn<br>240 |
| Trp | Thr | Asn | Thr | Gln<br>245 | Val | Arg | Ser | Ser | Leu<br>250 | Glu | Asn | Thr | Thr | Thr<br>255 |
| Lys | Leu | Gly | Asp | Ser<br>260 | Phe | Tyr | Tyr | Gly | Lys<br>265 | Gly | Leu | Ile | Asn | Val<br>270 |
| Gln | Ala | Ala | Ala | Gln<br>275 |   |   |   |   |   |   |   |   |   |   |

What is claimed is:

1. A subtilisin modified to have substrate specificity for peptide or polypeptide substrates having basic amino acids at the $P_1$, $P_2$ and $P_4$ positions of the substrate said subtilisin having an Asp or Glu at positions corresponding to amino acid Asn 62, Tyr 104 and Gly 166 in the amino acid sequence of the subtilisin having the amino acid sequence of SEQ ID NO: 90 naturally produced by Bacillus amyloliquefaciens.

2. The subtilisin of claim 1 wherein the amino acid is Asp.

3. The subtilisin of claim 2 having the amino acid sequence of SEQ ID NO: 75.

4. An isolated nucleic acid molecule encoding the subtilisin of claim 1.

5. The nucleic acid molecule of claim 4 further comprising a promoter operably linked to the nucleic acid molecule.

6. An expression vector comprising the nucleic acid molecule of claim 5 operably linked to control sequences recognized by a host cell transformed with the vector.

7. A host cell transformed with the vector of claim 6.

8. A process of using the nucleic acid molecule of claim 4 to effect production of the subtilisin comprising culturing the host cell of claim 7 under conditions suitable for expression of the subtilisin.

9. The process of claim 8 further comprising recovering the subtilisin from the host cell culture medium.

10. A method of using the subtilisin of claim 1 comprising contacting a fusion protein comprising a substrate amino acid sequence having basic amino acids at the $P_1$ $P_2$ and $P_4$ position of the substrate sequence with the subtilisin.

11. A process for cleaving a polypeptide, said polypeptide comprising an amino acid sequence represented by the formula:

P4-P3-P2-P1-P1' wherein,

P4 is a basic amino acid;

P3 is an amino acid selected from the naturally occurring amino acids;

P2 is a basic amino acid;

P1 is a basic amino acid; and

P1' is not Pro;

comprising the step of:

subjecting said polypeptide to the subtilisin of claim 1 in a reaction mixture under conditions such that the subtilisin cleaves the polypeptide.

* * * * *